United States Patent
Arad

(10) Patent No.: US 11,879,893 B2
(45) Date of Patent: Jan. 23, 2024

(54) RAPID DETECTION TEST FOR SARS-COV-2

(71) Applicant: NLC Pharma Ltd, Bnei-Brak (IL)

(72) Inventor: Dorit Arad, Tel Aviv (IL)

(73) Assignee: NLC Pharma Ltd, Bnei-Brak (IL)

( * ) Notice: Subject to any disclaimer, the term of this patent is extended or adjusted under 35 U.S.C. 154(b) by 0 days.

(21) Appl. No.: 17/883,833

(22) Filed: Aug. 9, 2022

(65) Prior Publication Data

US 2023/0090502 A1    Mar. 23, 2023

Related U.S. Application Data

(63) Continuation of application No. PCT/IL2021/050155, filed on Feb. 9, 2021.

(60) Provisional application No. 62/972,005, filed on Feb. 9, 2020.

(51) Int. Cl.
*G01N 33/569* (2006.01)
*B01L 3/00* (2006.01)

(52) U.S. Cl.
CPC ...... *G01N 33/56983* (2013.01); *B01L 3/5027* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 6,243,980 | B1 | 6/2001 | Bronstein et al. |
| 7,635,557 | B2 | 12/2009 | Arad |
| 9,474,759 | B2 | 10/2016 | Chang et al. |
| 10,077,433 | B2 * | 9/2018 | Binkowski ............... C12Q 1/66 |
| 10,502,739 | B2 | 12/2019 | Oved |
| 2005/0048473 | A1 | 3/2005 | Arad |

FOREIGN PATENT DOCUMENTS

| | | | |
|---|---|---|---|
| WO | WO 2007/029262 | 3/2007 | |
| WO | WO-2007029262 A2 * | 3/2007 | ............. A61P 31/12 |
| WO | WO 2021/156878 | 8/2021 | |

OTHER PUBLICATIONS

Perera et al., Antiviral Research vol. 160, pp. 79-86 (Year: 2018).*
NCBI Reference Sequence: YP_009724389.1 (Year: 2020).*
International Search Report and the Written Opinion dated Aug. 6, 2021 From the International Searching Authority Re. Application No. PCT/IL2021/050155. (23 Pages).
International Search Report and the Written Opinion dated Aug. 25, 2021 From the International Searching Authority Re. Application No. PCT/IL2021/050155. (35 Pages).
Invitation to Pay Additional Fees, Communication Relating to the Results of the Partial International Search and the Provisional Opinion dated Jun. 15, 2021 From the International Searching Authority Re. Application No. PCT/IL2021/050155. (13 Pages).
Nguyen et al. "Flavonoid-Mediated Inhibition of SARS Coronavirus 3C-Like Protease Expressed in Pichia Pastoris", Biotechnology Letters, 34(5): 831-838, Published Online Feb. 15, 2012.
Priye et al. "A Smartphone-Based Diagnostic Platform for Rapid Detection of Zika, Chikungunya, and Dengue Viruses", Scientific Reports, XP055488108, 7: 44778-1-44778-11, Mar. 20, 2017.
Zhu et al. "Identification of SARS-CoV-2 3CL Protease Inhibitors by a Quantitative High-Throughput Screening", ACS Pharmacology & Translational Science, 3(5): 1008-1016, Sep. 4, 2020.

* cited by examiner

*Primary Examiner* — Shanon A. Foley
*Assistant Examiner* — Myron G Hill

(57) ABSTRACT

The present invention is directed towards methods, compositions and kits for testing SARS-CO-V2 virus in a sample. The methods determine the presence of a viral 3CL protease by contacting the sample with a peptide compound capable of being cleaved by the protease to form peptide compound fragments. Detection of a peptide compound fragment confirms the presence of the virus.

10 Claims, 28 Drawing Sheets

Specification includes a Sequence Listing.

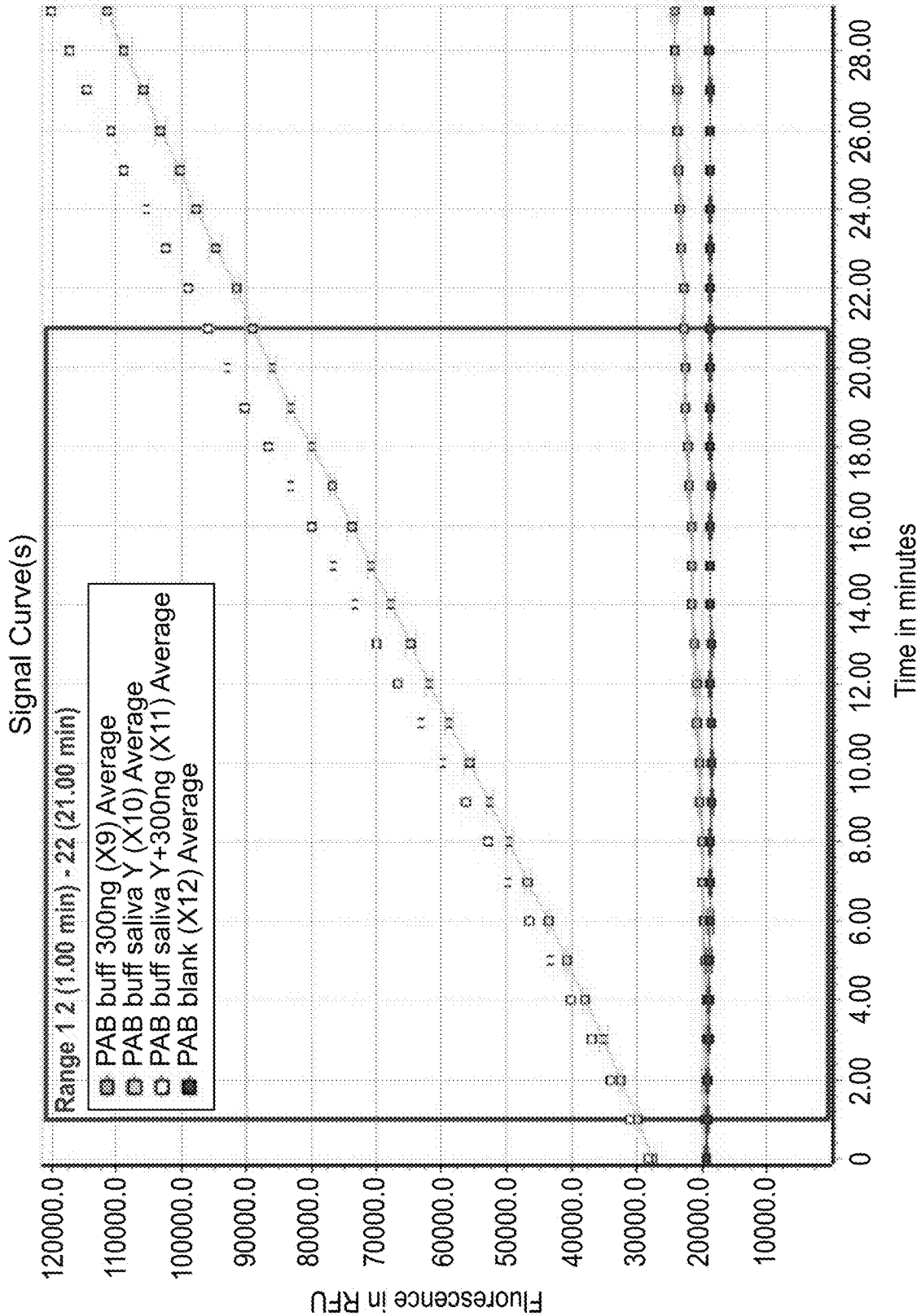

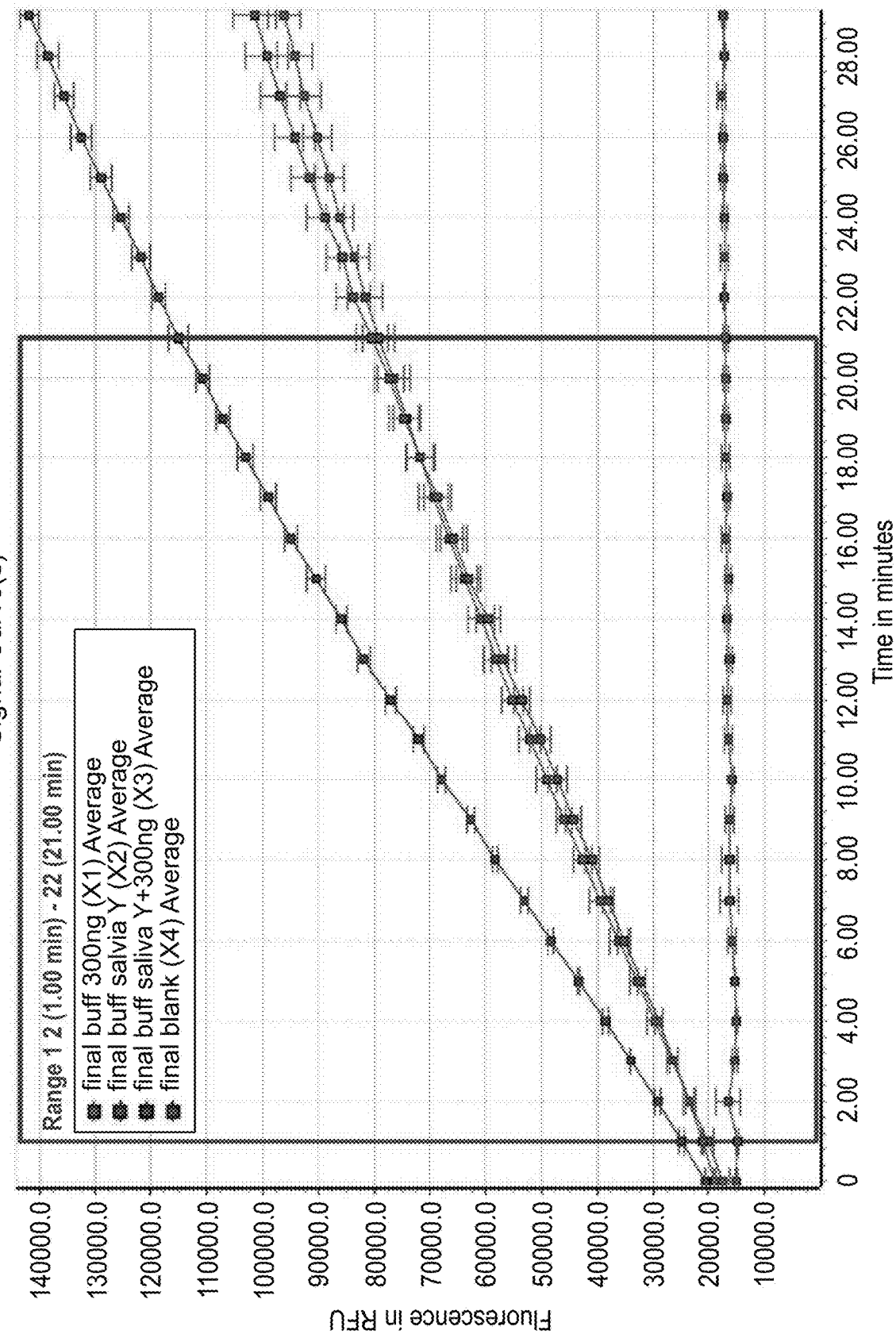

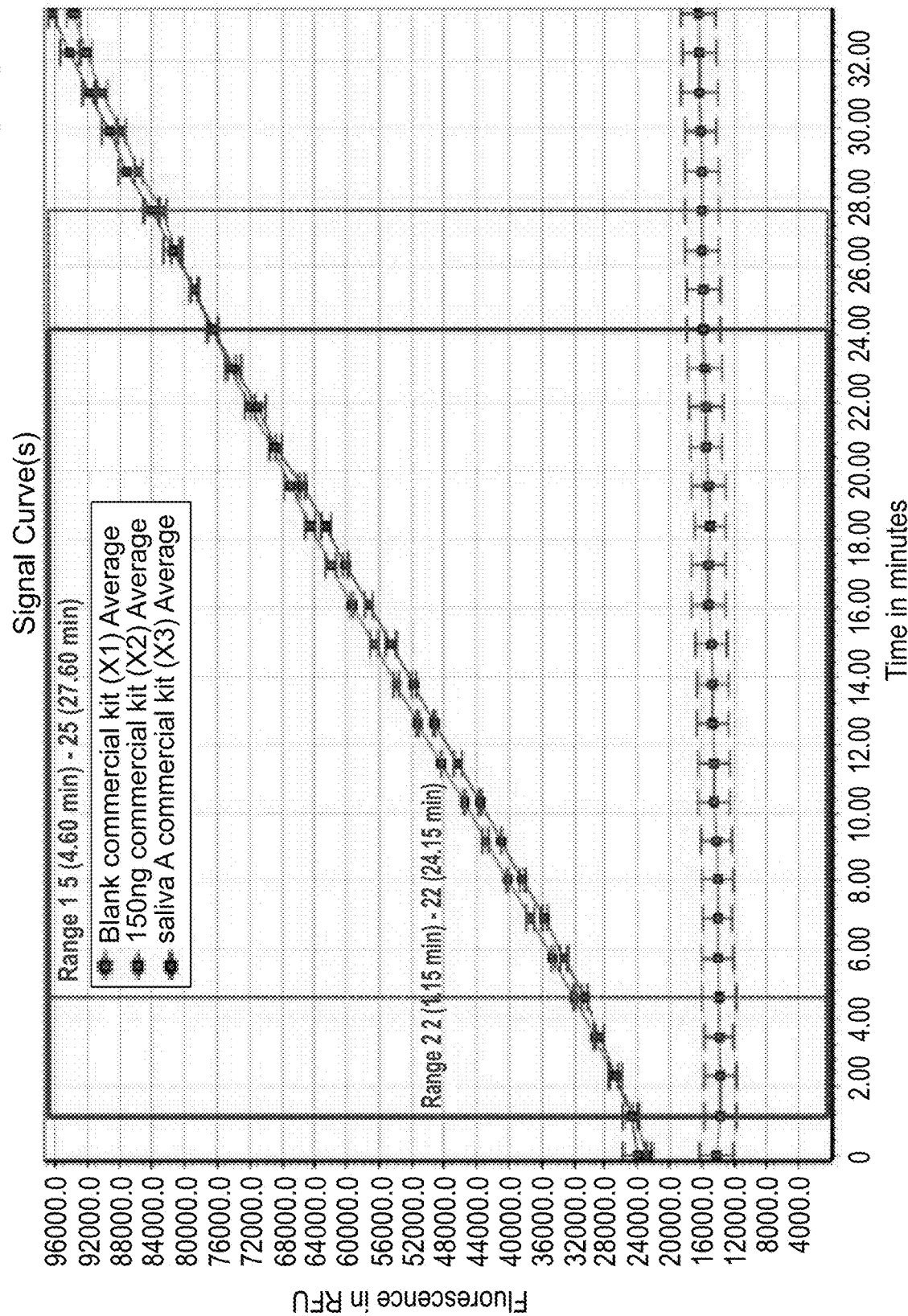

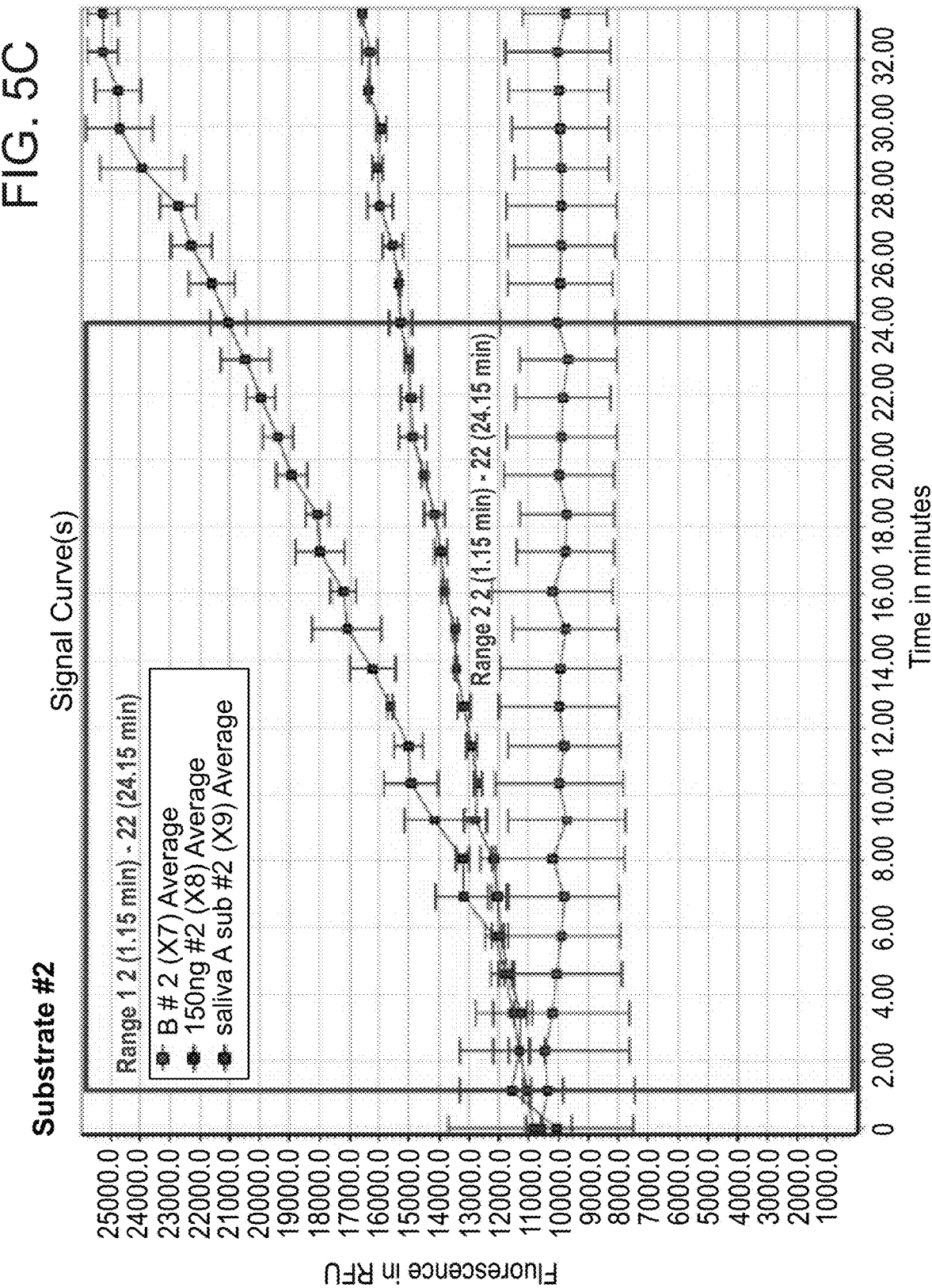

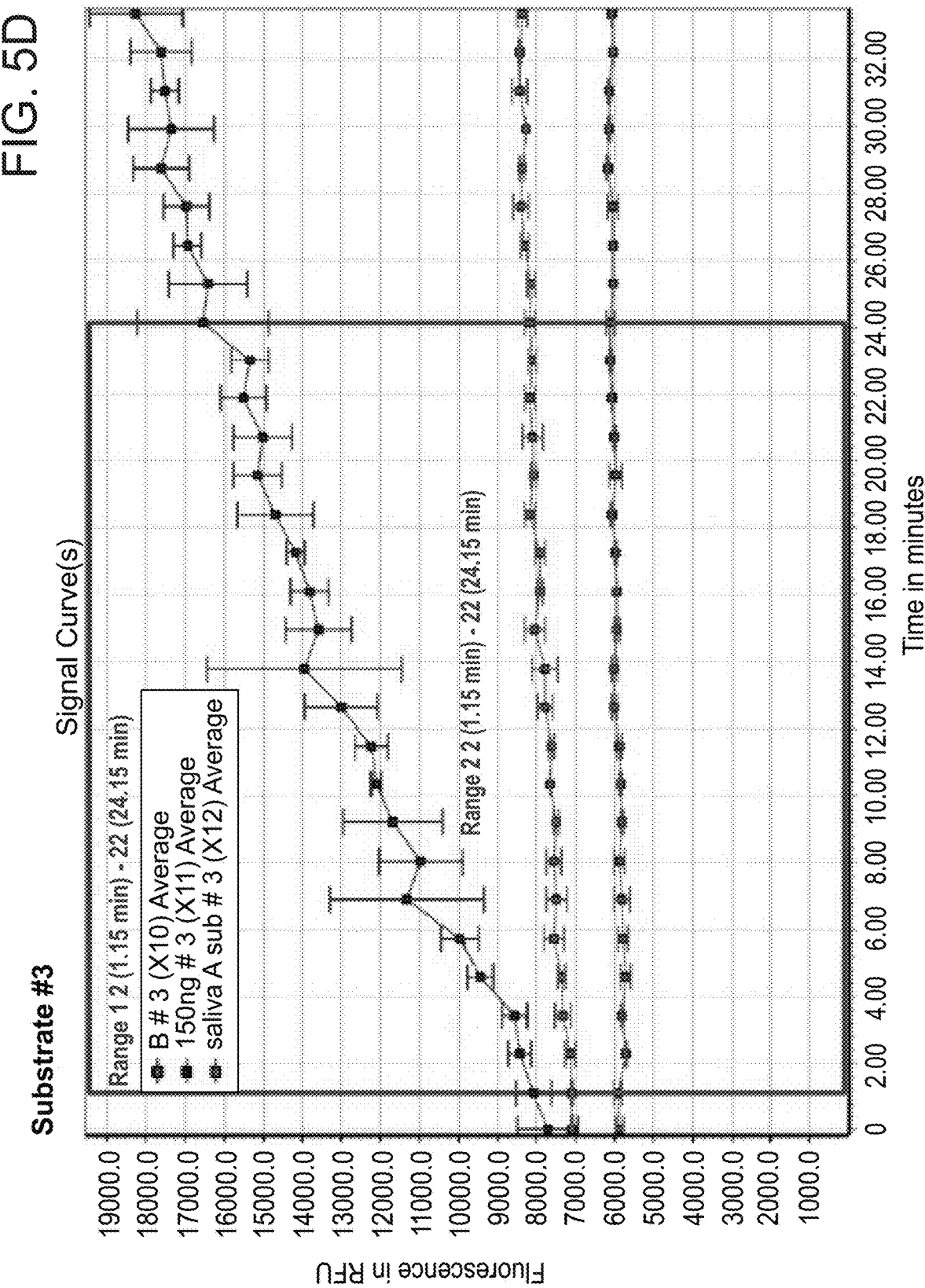

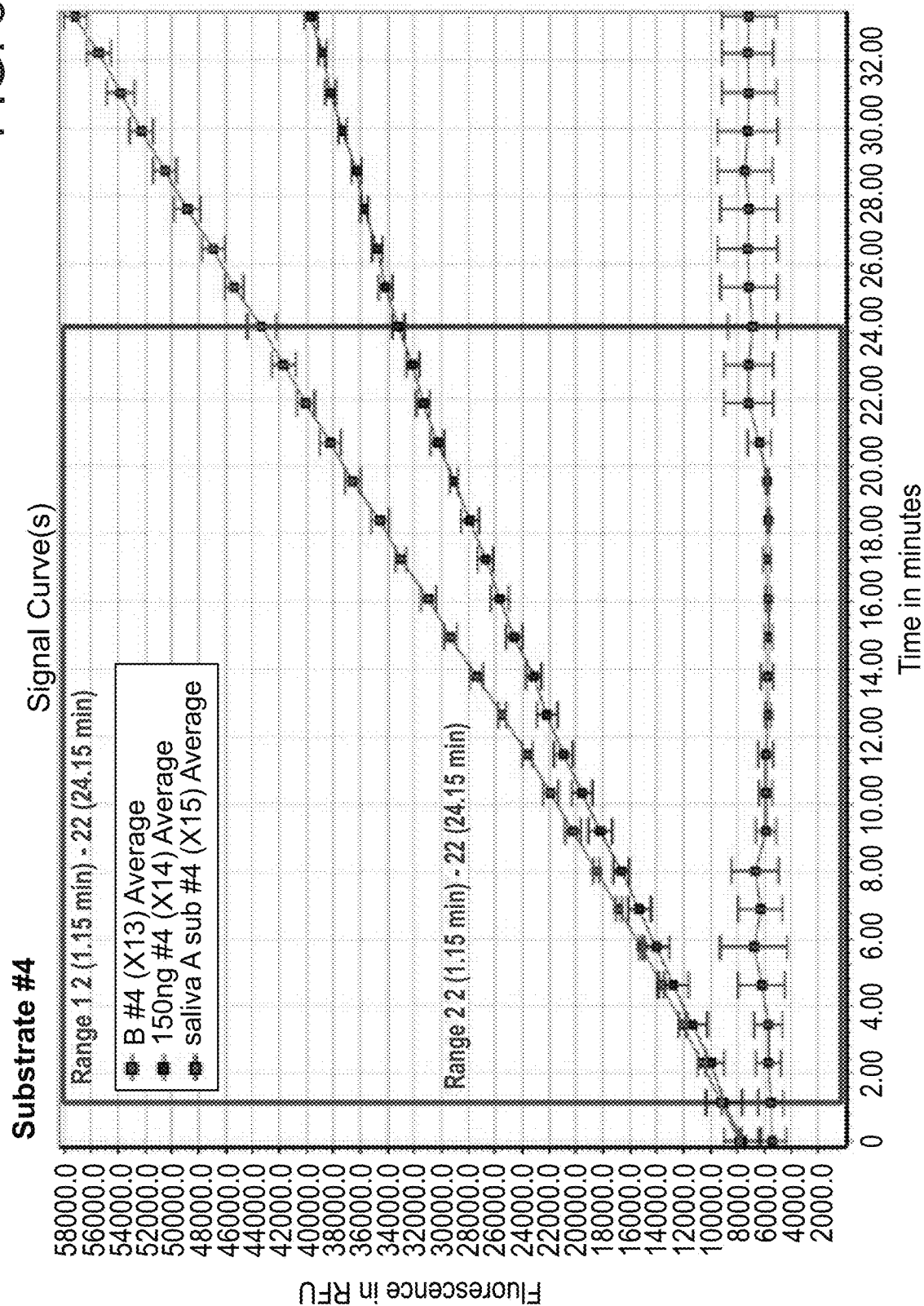

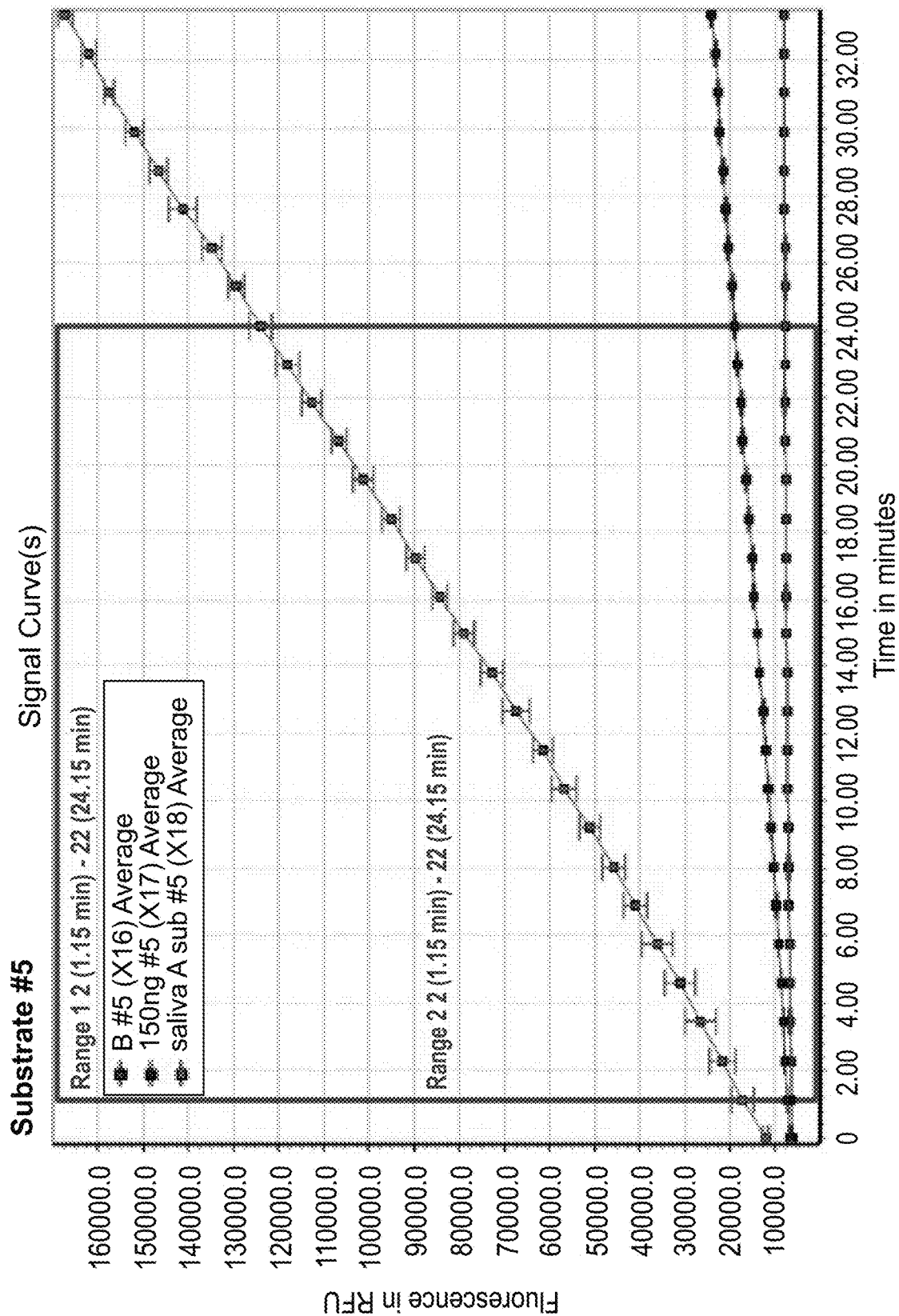

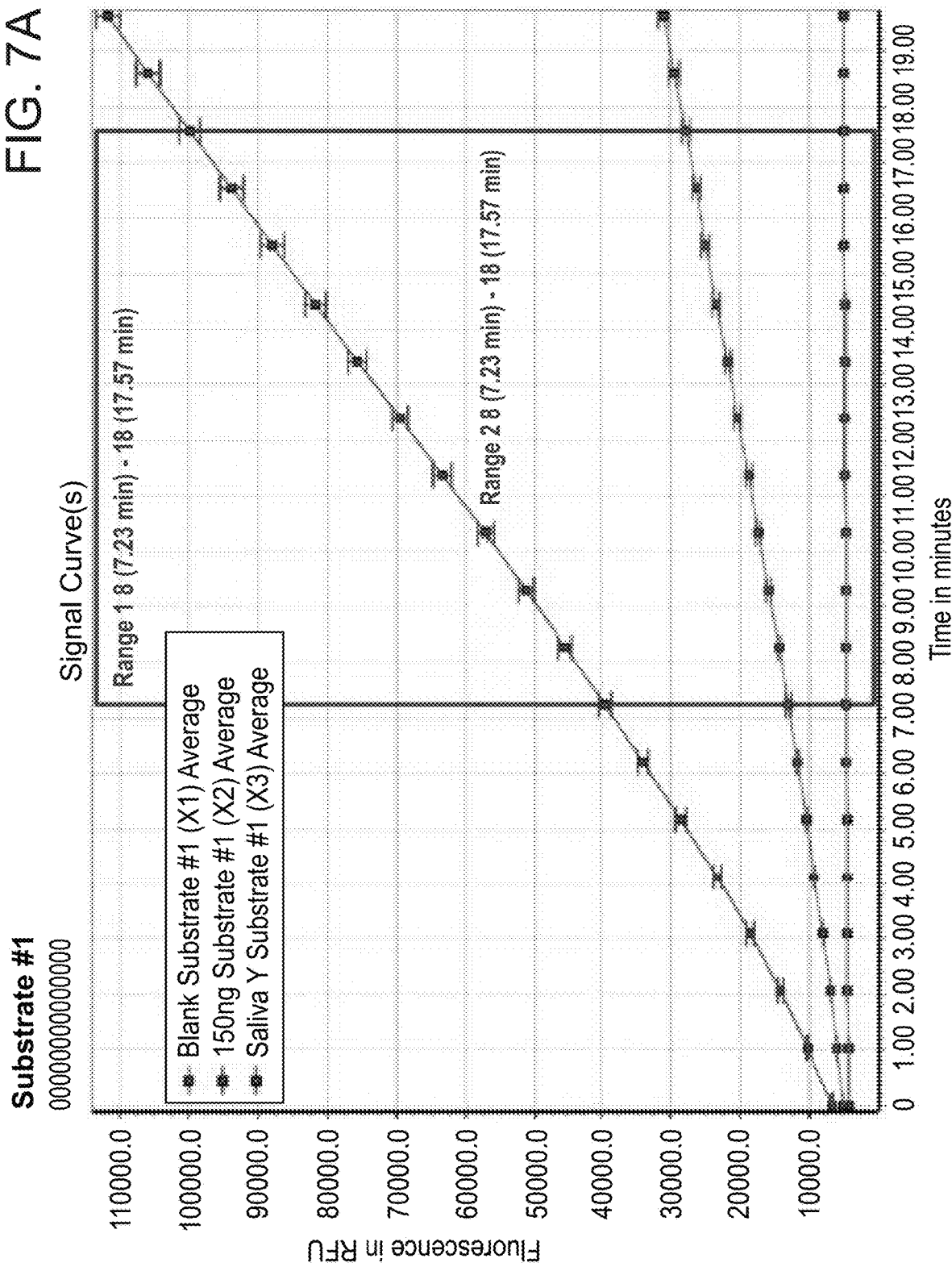

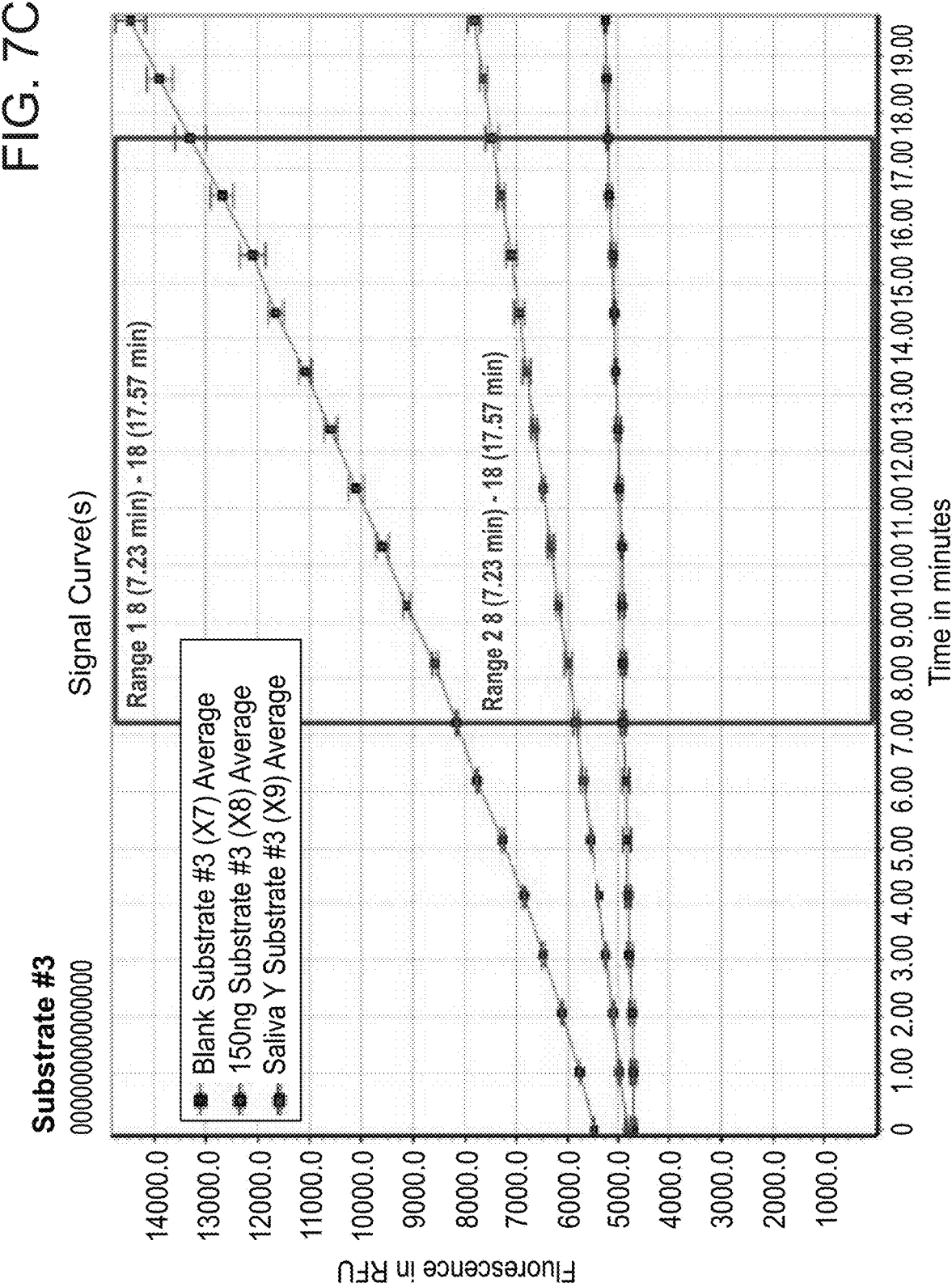

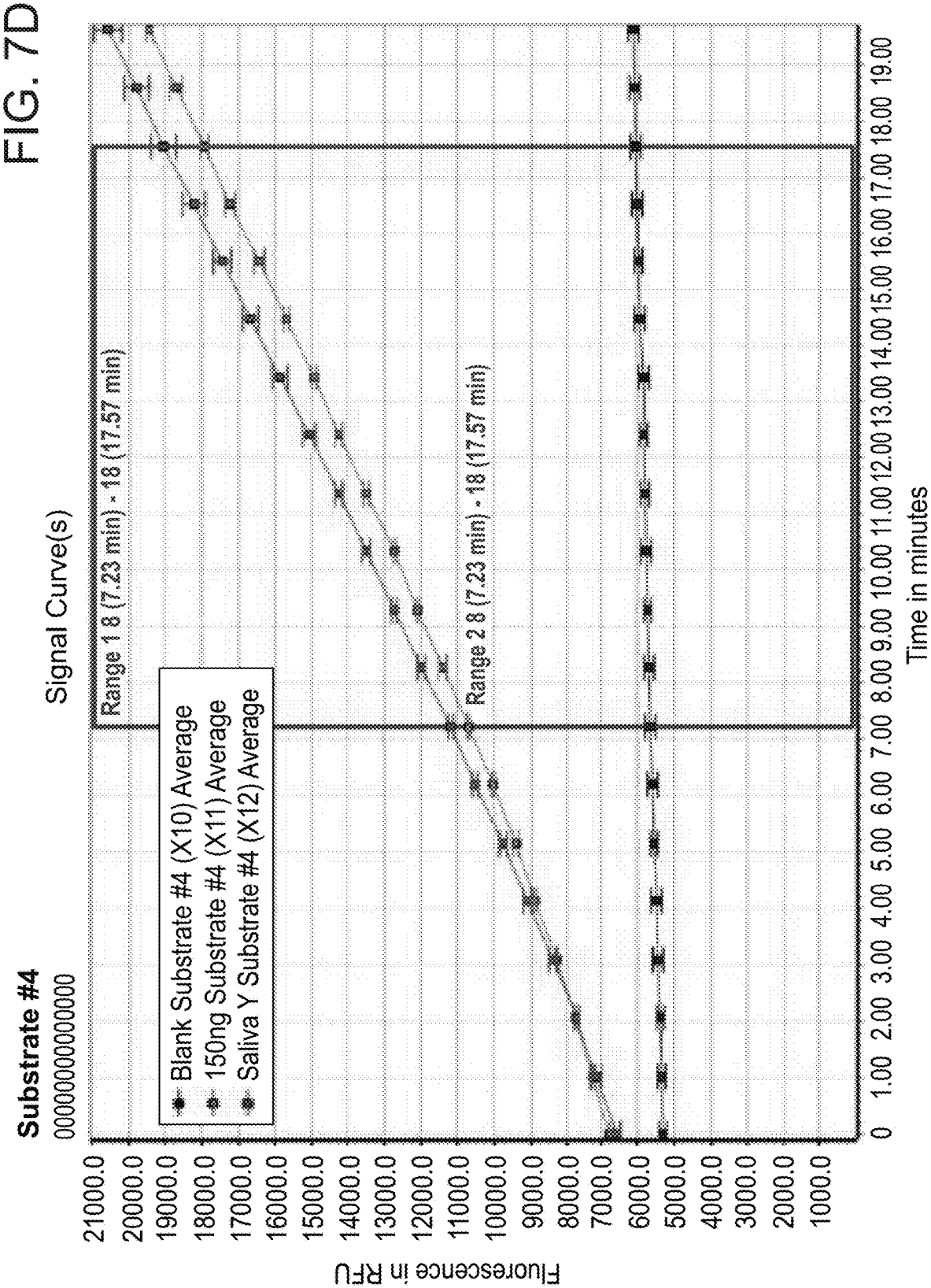

FIG. 15

SEQUENCE LISTING

```
Sequence total quantity: 39
SEQ ID NO: 1           moltype = AA  length = 14
FEATURE                Location/Qualifiers
REGION                 1..14
                       note = synthetic peptide
MOD_RES                1
                       note = Dabcyl 5' conjugated
MOD_RES                14
                       note = EDANS 3' conjugated
```

| | | |
|---|---|---|
| source | 1..14<br>mol_type = protein<br>organism = synthetic construct | |
| SEQUENCE: 1<br>KTSAVLQSGF RKME | | 14 |
| SEQ ID NO: 2<br>FEATURE<br>REGION | moltype = AA   length = 11<br>Location/Qualifiers<br>1..11<br>note = synthetic peptide | |
| MOD_RES | 1<br>note = Dabcyl 5' conjugated | |
| MOD_RES | 11<br>note = EDANS 3' conjugated | |
| source | 1..11<br>mol_type = protein<br>organism = synthetic construct | |
| SEQUENCE: 2<br>TSAVLQSGFR K | | 11 |
| SEQ ID NO: 3<br>FEATURE<br>REGION | moltype = AA   length = 9<br>Location/Qualifiers<br>1..9<br>note = synthetic peptide | |
| MOD_RES | 1<br>note = Dabcyl 5' conjugated | |
| MOD_RES | 9<br>note = EDANS 3' conjugated | |
| source | 1..9<br>mol_type = protein<br>organism = synthetic construct | |
| SEQUENCE: 3<br>TSAVLQSGF | | 9 |
| SEQ ID NO: 4<br>FEATURE<br>REGION | moltype = AA   length = 7<br>Location/Qualifiers<br>1..7<br>note = synthetic peptide | |
| MOD_RES | 1<br>note = Dabcyl 5' conjugated | |
| MOD_RES | 7<br>note = EDANS 3' conjugated | |
| source | 1..7<br>mol_type = protein<br>organism = synthetic construct | |
| SEQUENCE: 4<br>AVLQSGF | | 7 |
| SEQ ID NO: 5<br>FEATURE<br>REGION | moltype = AA   length = 9<br>Location/Qualifiers<br>1..9<br>note = synthetic peptide | |
| MOD_RES | 1<br>note = Dabcyl 5' conjugated | |
| MOD_RES | 9<br>note = EDANS 3' conjugated | |
| source | 1..9<br>mol_type = protein<br>organism = synthetic construct | |
| SEQUENCE: 5<br>AVLQSGFRK | | 9 |
| SEQ ID NO: 6<br>FEATURE<br>REGION | moltype = AA   length = 11<br>Location/Qualifiers<br>1..11<br>note = synthetic peptide | |
| MOD_RES | 1<br>note = Dabcyl 5' conjugated | |
| MOD_RES | 11<br>note = EDANS 3' conjugated | |
| source | 1..11<br>mol_type = protein<br>organism = synthetic construct | |
| SEQUENCE: 6<br>TSAVLQSGFY K | | 11 |
| SEQ ID NO: 7<br>FEATURE<br>REGION | moltype = AA   length = 12<br>Location/Qualifiers<br>1..12 | |

```
                    note = synthetic peptide
MOD_RES             1
                    note = BHQ-1 conjugated
MOD_RES             12
                    note = AF488 conjugated
MOD_RES             12
                    note = AMIDATION
source              1..12
                    mol_type = protein
                    organism = synthetic construct
SEQUENCE: 7
TSAVLQSGFR KC                                                                   12

SEQ ID NO: 8        moltype = AA   length = 12
FEATURE             Location/Qualifiers
REGION              1..12
                    note = synthetic peptide
MOD_RES             1
                    note = BHQ-1 conjugated
MOD_RES             10
                    note = AF488 conjugated
MOD_RES             10
                    note = AMIDATION
source              1..12
                    mol_type = protein
                    organism = synthetic construct
SEQUENCE: 8
TSAVLQSGFC RK                                                                   12

SEQ ID NO: 9        moltype = AA   length = 10
FEATURE             Location/Qualifiers
REGION              1..10
                    note = synthetic peptide
MOD_RES             1
                    note = BHQ-1 conjugated
MOD_RES             8
                    note = AF488 conjugated
MOD_RES             10
                    note = AMIDATION
source              1..10
                    mol_type = protein
                    organism = synthetic construct
SEQUENCE: 9
AVLQSGFCRK                                                                      10

SEQ ID NO: 10       moltype = AA   length = 10
FEATURE             Location/Qualifiers
REGION              1..10
                    note = synthetic peptide
MOD_RES             1
                    note = BHQ-1 conjugated
MOD_RES             10
                    note = AF488 conjugated
MOD_RES             10
                    note = AMIDATION
source              1..10
                    mol_type = protein
                    organism = synthetic construct
SEQUENCE: 10
AVLQSGFRKC                                                                      10

SEQ ID NO: 11       moltype = AA   length = 11
FEATURE             Location/Qualifiers
REGION              1..11
                    note = synthetic peptide
MOD_RES             1
                    note = Dabcylconjugated
MOD_RES             11
                    note = EDANS 3' conjugated
source              1..11
                    mol_type = protein
                    organism = synthetic construct
SEQUENCE: 11
YGSTLQAGLR K                                                                    11

SEQ ID NO: 12       moltype = AA   length = 11
FEATURE             Location/Qualifiers
REGION              1..11
                    note = synthetic peptide
```

```
MOD_RES           1
                  note = Dabcyl 5' conjugated
MOD_RES           9
                  note = EDANSconjugated
MOD_RES           11
                  note = AMIDATION
source            1..11
                  mol_type = protein
                  organism = synthetic construct
SEQUENCE: 12
LEALFQGPDS Q                                                              11

SEQ ID NO: 13     moltype = AA  length = 7
FEATURE           Location/Qualifiers
REGION            1..7
                  note = synthetic peptide
source            1..7
                  mol_type = protein
                  organism = synthetic construct
SEQUENCE: 13
AVLQSGF                                                                   7

SEQ ID NO: 14     moltype = AA  length = 6
FEATURE           Location/Qualifiers
REGION            1..6
                  note = synthetic peptide
source            1..6
                  mol_type = protein
                  organism = synthetic construct
SEQUENCE: 14
TFQSAV                                                                    6

SEQ ID NO: 15     moltype = AA  length = 6
FEATURE           Location/Qualifiers
REGION            1..6
                  note = synthetic peptide
source            1..6
                  mol_type = protein
                  organism = synthetic construct
SEQUENCE: 15
TVQSKM                                                                    6

SEQ ID NO: 16     moltype = AA  length = 7
FEATURE           Location/Qualifiers
REGION            1..7
                  note = synthetic peptide
source            1..7
                  mol_type = protein
                  organism = synthetic construct
SEQUENCE: 16
TLQAIAS                                                                   7

SEQ ID NO: 17     moltype = AA  length = 7
FEATURE           Location/Qualifiers
REGION            1..7
                  note = synthetic peptide
source            1..7
                  mol_type = protein
                  organism = synthetic construct
SEQUENCE: 17
KLQNNEL                                                                   7

SEQ ID NO: 18     moltype = AA  length = 6
FEATURE           Location/Qualifiers
REGION            1..6
                  note = synthetic peptide
source            1..6
                  mol_type = protein
                  organism = synthetic construct
SEQUENCE: 18
RLQAGN                                                                    6

SEQ ID NO: 19     moltype = AA  length = 6
FEATURE           Location/Qualifiers
REGION            1..6
                  note = synthetic peptide
source            1..6
                  mol_type = protein
                  organism = synthetic construct
```

```
SEQUENCE: 19
MLQSAD                                                                    6

SEQ ID NO: 20           moltype = AA  length = 6
FEATURE                 Location/Qualifiers
REGION                  1..6
                        note = synthetic peptide
source                  1..6
                        mol_type = protein
                        organism = synthetic construct
SEQUENCE: 20
VLQAVG                                                                    6

SEQ ID NO: 21           moltype = AA  length = 7
FEATURE                 Location/Qualifiers
REGION                  1..7
                        note = synthetic peptide
source                  1..7
                        mol_type = protein
                        organism = synthetic construct
SEQUENCE: 21
TLQAENV                                                                   7

SEQ ID NO: 22           moltype = AA  length = 7
FEATURE                 Location/Qualifiers
REGION                  1..7
                        note = synthetic peptide
source                  1..7
                        mol_type = protein
                        organism = synthetic construct
SEQUENCE: 22
RLQSLEN                                                                   7

SEQ ID NO: 23           moltype = AA  length = 7
FEATURE                 Location/Qualifiers
REGION                  1..7
                        note = synthetic peptide
source                  1..7
                        mol_type = protein
                        organism = synthetic construct
SEQUENCE: 23
KLQSSQA                                                                   7

SEQ ID NO: 24           moltype = AA  length = 14
FEATURE                 Location/Qualifiers
REGION                  1..14
                        note = synthetic peptide
source                  1..14
                        mol_type = protein
                        organism = synthetic construct
SEQUENCE: 24
KTSAVLQSGF RKME                                                          14

SEQ ID NO: 25           moltype = AA  length = 11
FEATURE                 Location/Qualifiers
REGION                  1..11
                        note = synthetic peptide
source                  1..11
                        mol_type = protein
                        organism = synthetic construct
SEQUENCE: 25
TSAVLQSGFR K                                                             11

SEQ ID NO: 26           moltype = AA  length = 9
FEATURE                 Location/Qualifiers
REGION                  1..9
                        note = synthetic peptide
source                  1..9
                        mol_type = protein
                        organism = synthetic construct
SEQUENCE: 26
TSAVLQSGF                                                                 9

SEQ ID NO: 27           moltype = AA  length = 7
FEATURE                 Location/Qualifiers
REGION                  1..7
                        note = synthetic peptide
source                  1..7
                        mol_type = protein
```

```
                        organism = synthetic construct
SEQUENCE: 27
AVLQSGF                                                                  7

SEQ ID NO: 28           moltype = AA   length = 9
FEATURE                 Location/Qualifiers
REGION                  1..9
                        note = synthetic peptide
source                  1..9
                        mol_type = protein
                        organism = synthetic construct
SEQUENCE: 28
AVLQSGFRK                                                                9

SEQ ID NO: 29           moltype = AA   length = 11
FEATURE                 Location/Qualifiers
REGION                  1..11
                        note = synthetic peptide
source                  1..11
                        mol_type = protein
                        organism = synthetic construct
SEQUENCE: 29
TSAVLQSGFY K                                                            11

SEQ ID NO: 30           moltype = AA   length = 12
FEATURE                 Location/Qualifiers
REGION                  1..12
                        note = synthetic peptide
SITE                    12
                        note = misc_feature - Xaa can be any naturally occurring
                         amino acid
source                  1..12
                        mol_type = protein
                        organism = synthetic construct
SEQUENCE: 30
TSAVLQSGFR KX                                                           12

SEQ ID NO: 31           moltype = AA   length = 12
FEATURE                 Location/Qualifiers
REGION                  1..12
                        note = synthetic peptide
SITE                    10
                        note = misc_feature - Xaa can be any naturally occurring
                         amino acid
source                  1..12
                        mol_type = protein
                        organism = synthetic construct
SEQUENCE: 31
TSAVLQSGFX RK                                                           12

SEQ ID NO: 32           moltype = AA   length = 10
FEATURE                 Location/Qualifiers
REGION                  1..10
                        note = synthetic peptide
SITE                    8
                        note = misc_feature - Xaa can be any naturally occurring
                         amino acid
source                  1..10
                        mol_type = protein
                        organism = synthetic construct
SEQUENCE: 32
AVLQSGFXRK                                                              10

SEQ ID NO: 33           moltype = AA   length = 10
FEATURE                 Location/Qualifiers
REGION                  1..10
                        note = synthetic peptide
SITE                    10
                        note = misc_feature - Xaa can be any naturally occurring
                         amino acid
source                  1..10
                        mol_type = protein
                        organism = synthetic construct
SEQUENCE: 33
AVLQSGFRKX                                                              10

SEQ ID NO: 34           moltype = AA   length = 306
FEATURE                 Location/Qualifiers
REGION                  1..306
```

```
                        note = 3CL protease of the SARS-CoV-2 virus
source                  1..306
                        mol_type = protein
                        organism = synthetic construct
SEQUENCE: 34
SGFRKMAFPS GKVEGCMVQV TCGTTTLNGL WLDDVVYCPR HVICTSEDML NPNYEDLLIR    60
KSNHNFLVQA GNVQLRVIGH SMQNCVLKLK VDTANPKTPK YKFVRIQPGQ TFSVLACYNG   120
SPSGVYQCAM RPNFTIKGSF LNGSCGSVGF NIDYDCVSFC YMHHMELPTG VHAGTDLEGN   180
FYGPFVDRQT AQAAGTDTTI TVNVLAWLYA AVINGDRWFL NRFTTTLNDF NLVAMKYNYE   240
PLTQDHVDIL GPLSAQTGIA VLDMCASLKE LLQNGMNGRT ILGSALLEDE FTPFDVVRQC   300
SGVTFQ                                                              306

SEQ ID NO: 35           moltype = AA  length = 320
FEATURE                 Location/Qualifiers
REGION                  1..320
                        note = 3CL protease of the SARS-CoV-2 virus with the
                         histidine tag andcleavable sequence
source                  1..320
                        mol_type = protein
                        organism = synthetic construct
SEQUENCE: 35
MHHHHHHENL YFQGSGFRKM AFPSGKVEGC MVQVTCGTTT LNGLWLDDVV YCPRHVICTS    60
EDMLNPNYED LLIRKSNHNF LVQAGNVQLR VIGHSMQNCV LKLKVDTANP KTPKYKFVRI   120
QPGQTFSVLA CYNGSPSGVY QCAMRPNFTI KGSFLNGSCG SVGFNIDYDC VSFCYMHHME   180
LPTGVHAGTD LEGNFYGPFV DRQTAQAAGT DTTITVNVLA WLYAAVINGD RWFLNRFTTT   240
LNDFNLVAMK YNYEPLTQDH VDILGPLSAQ TGIAVLDMCA SLKELLQNGM NGRTILGSAL   300
LEDEFTPFDV VRQCSGVTFQ                                               320

SEQ ID NO: 36           moltype = AA  length = 183
FEATURE                 Location/Qualifiers
REGION                  1..183
                        note = sequence of HRV 3C protease
source                  1..183
                        mol_type = protein
                        organism = synthetic construct
SEQUENCE: 36
GPEEEFGMSI IKNNTCVVTT TNGKFTGLGI YDRILILPTH ADPGSEIQVN GIHTKVLDSY    60
DLFNKEGVKL EITVLKLDRN EKFRDIRKYI PESEDDYPEC NLALVANQTE PTIIKVGDVV   120
SYGNILLSGT QTARMLKYNY PTKSGYCGGV LYKIGQILGI HVGGNGRDGF SSMLLRSYFT   180
EQQ                                                                 183

SEQ ID NO: 37           moltype = AA  length = 7
FEATURE                 Location/Qualifiers
REGION                  1..7
                        note = cleavable tag
source                  1..7
                        mol_type = protein
                        organism = synthetic construct
SEQUENCE: 37
ENLYFQG                                                               7

SEQ ID NO: 38           moltype = AA  length = 12
FEATURE                 Location/Qualifiers
REGION                  1..12
                        note = synthetic peptide
source                  1..12
                        mol_type = protein
                        organism = synthetic construct
SEQUENCE: 38
TSAVLQSGFC RK                                                        12

SEQ ID NO: 39           moltype = AA  length = 12
FEATURE                 Location/Qualifiers
REGION                  1..12
                        note = synthetic peptide
source                  1..12
                        mol_type = protein
                        organism = synthetic construct
SEQUENCE: 39
TSAVLQSGFR KC                                                        12
```

RAPID DETECTION TEST FOR SARS-COV-2

RELATED APPLICATIONS

This application is a Continuation of PCT Patent Application No. PCT/IL2021/050155 having International filing date of Feb. 9, 2021, which claims the benefit of priority under 35 USC § 119(e) of U.S. Provisional Patent Application No. 62/972,005 filed on Feb. 9, 2020. The contents of the above applications are all incorporated by reference as if fully set forth herein in their entirety.

SEQUENCE LISTING STATEMENT

The ASCII file, entitled 93621SequenceListing.txt, created on Aug. 9, 2022, comprising 16,961 bytes, submitted concurrently with the filing of this application is incorporated herein by reference. The sequence listing submitted herewith is identical to the sequence listing forming part of the international application.

TECHNICAL FIELD

The present invention relates to the field of viral sensing and rapid diagnostics, in general, and to a method, reagents and a kit for the detection of SARS-CoV-2 in a test sample, in particular. The method involves the detection of the 3C-L protease.

BACKGROUND

Timely and accurate COVID-19 testing is an essential part of the management of the current pandemic. The etiologic agent of COVID-19 is the Severe Acute Respiratory Syndrome Coronavirus 2 (SARS-CoV-2), which is a newly emerged member of the family Coronaviridae, subfamily Coronavirinae, genus β coronaviridae that includes the SARS-CoV and MERS-CoV viruses. These viruses are involved in Severe Acute Respiratory Syndrome (SARS) outbreaks in the past two decades. U.S. Pat. No. 10,130,701 B2 describes an attenuated coronavirus SARS-CoV comprising a variant replicase gene, which causes the virus to have reduced pathogenicity.

The SARS-CoV-2 viral genome is a single-strand, positive-sense RNA with a size of ~30 kb, which contains numerous open-reading frames. Two-thirds of the viral genome encodes 16 non-structural proteins (nsp1-16), while the remaining genome encodes four structural and nine accessory proteins (Orf3a, Orf3b, Orf6, Orf7a, Orf7b, Orf8, Orf9b, Orf9c, and Orf10). Several non-structural proteins harbour enzymatic activities, such as protease activity and RNA-directed RNA polymerase activities.

SARS-CoV-2 replicates at much higher levels in the nose and mouth than SARS-CoV and MERS, and this leads to much higher levels of virus shedding in the environment by people who are either pre-symptomatic or asymptomatic. Thus, a large percentage of infected people can transmit the virus without realizing that they are even infected. Due to these reasons, rapid, low cost and accurate methods of SARS-CoV-2 detection are critical for significantly slowing the spread of the virus and for population surveillance well into the future.

Currently, the molecular technique of quantitative real time polymerase chain reaction (qRT PCR) is the gold standard for SARS-CoV-2 detection using samples from respiratory secretions. Cycle threshold (CT) values of the PCR tests indicate the CT used in the PCR for exponential amplification of the target specimen and are inversely related to the viral load in the sample. CT40 is the accepted minimum viral load that can be detected by high-end PCR techniques. However, as noted above, the cost and organizational complexity of performing a large number of PCR reactions for downstream applications render this option feasible but unattractive. Furthermore, the SARS-CoV-2 virus is mutating over time, resulting in genetic variation in the population of circulating viral strains, which become indistinguishable by the routine PCR tests. Thus, false negative results frequently occur with any molecular test for the detection of SARS-CoV-2 if some particular mutation occurs in the part of the virus' genome assessed by that test. Lastly, PCR-based assays can produce false positive results because they cannot distinguish between nucleic acid fragments from live vs dead, decaying or inactive virus.

Several other molecular assays have been recently developed to detect the present SARS-CoV-2 virus, based on enzyme-linked immunosorbent assay (ELISA), and rapid tests that aim to detect either antibodies against the virus or the viral antigen themselves. Nevertheless, most of these immunochemical assays have recently failed due to the large number of false negative or false positive results. These assays also suffer from the same issue of not being able to distinguish between active or inactive viral products.

Moreover, antibodies against specific proteins of a new virus may not be instantly and constantly available (e.g., monoclonals). The production of antibodies uses biological systems. To produce antibodies, the induction of an immune response is necessary. However, this procedure might discriminate target proteins that has similar structure to endogenous protein or toxic compounds that would kill the animal. Another complication for in-vivo production of antibodies is that the antibodies can only work under physiological conditions. This restricts the range of application and function of antibodies. It is worthwhile to mention here that the last, but not the least problem of ELISA is that the same antibodies produced by different animals may significantly differ in their structure and functionality. As a result, any ELISA-based bioassay or biosensing system for detection of a certain analyte would differ in sensitivity and specificity, and might be difficult to calibrate and universalize.

Thus, while antibody recognition has been the gold standard for decades, numerous problems mentioned above abound towards new designs, limited protein shelf lives, time-consuming washing procedures and manufacturing scale-up. These problems can be surmounted, but only through laborious research programs at great cost. Although the aforementioned PCR methods and immunoassays have recently been developed to detect the presence of, or exposure to SARS-CoV-2 virus, but they do not distinguish between active vs. degraded virus remnants. Because of the deficiencies of the presently available testing methods, there is a need for an improved test enabling the presence of viruses, such as the SARS-CoV-2 virus, to be accurately and rapidly detected at an early stage of infection. Such a test will benefit those showing symptoms of COVID-19 by allowing for the monitoring of the course of their infection and subsequent recovery. In addition, a rapid, sensitive and selective test will benefit persons suspected of having the disease by allowing uninfected persons to be released from quarantine. There is also the need for an automated test avoiding the need for manual intervention. Such a test will prevent spread of the disease due to infection during the testing process.

During the replication of many viruses, the viral genetic material is transcribed and translated to form a polyprotein, which is ultimately cleaved into biologically active proteins by an essential virally encoded cysteine protease. The 3C-like protease (3CLpro), formally known as C30 Endopeptidase, is the main protease found in coronaviruses. It cleaves the coronavirus polyprotein at 11 conserved sites, and it is the main protease found in SARS-CoV-1 and SARS-CoV-2, which is responsible for the viral replication. Both viruses have this 3C-Like cysteine protease that exhibits similar, but not identical cleavage-site specificity to that of picornavirus 3C protease, and are therefore termed "3C-Like protease" (3CL protease). U.S. Pat. No. 7,635,557 by the present inventors describes methods, compositions and kits for testing for SARS-CoV-1 virus in a sample. The methods determine the presence of the 3CL protease by contacting the sample with a peptide compound capable of being cleaved by the 3CL protease to form peptide compound fragments. Detection of a peptide compound fragment confirms the presence of the virus. Quantitation of the 3CL protease activity presents a unique approach to viral diagnosis. The premise for a diagnostic test is that clinical samples, such as nasopharyngeal swab, saliva, buccal swab others, are collected and incubated in the presence of a peptide substrate containing the unique viral cleavage sequence linked to particular analytical probes, for examples donor and quencher fluorophores at the amino and carboxyl terminals. Presence of active SARS CoV-2 3CL protease can then be detected by peptide cleavage, which results in a visual signal that can be easily quantified with any suitable analytical technical, for example fluorescence or luminescence spectroscopy, terahertz spectroscopy, lateral flow etc.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or apparatus of embodiments of the invention can involve performing or completing selected tasks manually, automatically, or a combination thereof. Moreover, according to actual instrumentation and equipment of embodiments of the method and/or apparatus of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or apparatus as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

The present invention describes embodiments of a method of diagnosing a Severe Acute Respiratory Syndrome Coronavirus 2 (SARS-CoV-2) infection in a sample of a subject, the method comprising contacting the sample with a composition comprising an agent that detects 3CL-protease of the SARS-Co-V2 virus, wherein a presence of the 3CL-protease in the sample is indicative of a SARS-Co-V2 infection.

In another embodiment, the method of detecting a SARS-CoV-2 virus in a sample of a subject suspected of having COVID-19 comprises comprising contacting the sample with a composition comprising an agent that monitors the activity of a 3CL protease of the SARS-CoV-2 virus, wherein the activity level of the 3CL protease in the sample is indicative of the presence of SARS-CoV-2 in the sample.

In particular embodiments, the sample is selected from the group consisting of mucus, saliva, throat wash, nasal wash, spinal fluid, sputum, urine, semen, sweat, faeces, plasma, blood, bronchioalveolar fluid, vaginal fluid, tear fluid, tissue biopsy, and nasopharyngeal, oropharyngeal, nasal mid turbinate, anterior nasal and buccal swabs.

In other embodiments, the detectable moiety is a fluorescence moiety. In a particular embodiment, the detectable moiety is a Förster Resonance Energy Transfer (FRET) pair of donor and acceptor moieties, and the cleavage of the substrate peptide generates or modulates a signal from the FRET pair. Specific donor moiety is a quantum dot.

In certain embodiments, the donor and acceptor moiety are attached to the peptide in a configuration that permits energy transfer from the donor to the acceptor to result in quenching of the fluorescence by FRET process. In some other embodiments, the donor and acceptor moiety are separated by no more than 3, 5, 10, 15 or 20 amino acid residues.

In a further embodiment, the acceptor moiety the acceptor moiety is radiative or non-radiative. Specific examples of the acceptors used in the present invention are tetramethyl-6-carboxyrhodamine (TAMRA) and Black Hole Quenchers (BHQs) including Black Hole Quencher-1 (BHQ-1), Black Hole Quencher-2 (BHQ-2), Black Hole Quencher-3 (BHQ-3). Specific FRET pairs are Alexa Fluor® 488 (AF488) (donor)/BHQ1 (acceptor), AF488 (donor)/QSY9 (acceptor), EDANS (donor)/DABCYL (acceptor).

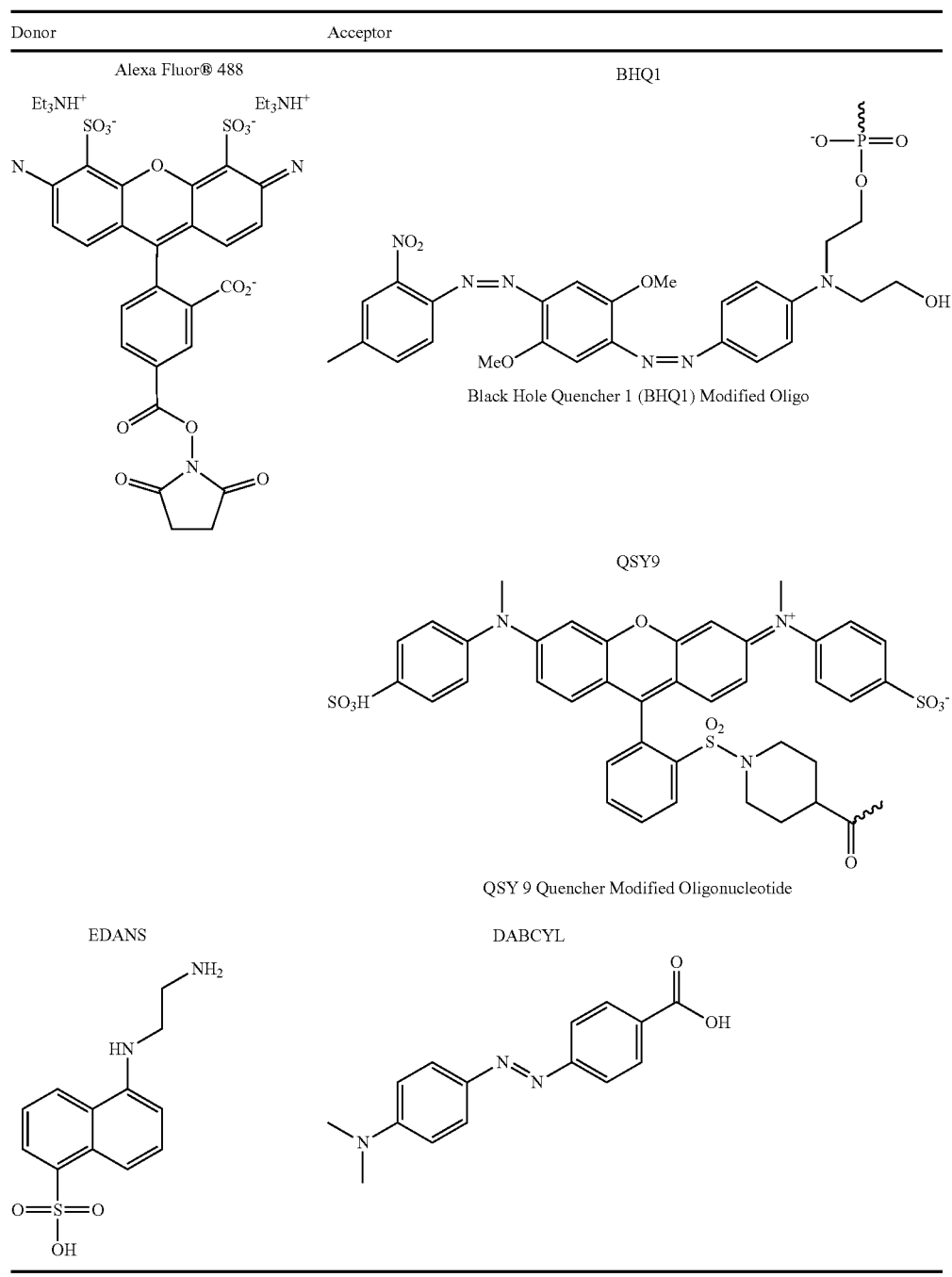

In other embodiments, the C-terminus of the peptide is attached to the acceptor moiety and the N-terminus of the peptide is attached to the donor moiety. In still other embodiments, the C-terminus of the peptide is attached to the acceptor moiety and the donor moiety is attached to no more than three amino acids from the N-terminus. In a particular embodiment, the donor moiety is attached to the separating moiety Z.

In a further embodiment, the detectable moiety is a chemiluminescent signalling moiety attached to one side of the cleavage region of the substrate peptide, and an acceptor moiety is attached at the other side of the cleavage region of the substrate peptide. Non-limiting example of the chemiluminescent signalling moiety is a 1,2-dioxetane compound.

In yet further embodiment, the detectable moiety is a pre-enzyme, which upon substrate peptide cleavage is activated and detected via the detection of a catalytic activity of same. Non-limiting example of the pre-enzyme is pro-Thrombin (factor II) or other enzymes in this cascade.

In some embodiment, the substrate peptide Y comprises a sequence of 8-12 amino acids. In a particular embodiment, this sequence is an amino acid sequence selected from the group consisting of SEQ ID Nos: 13-23, specifically SEQ ID NO: 13, more specifically SEQ ID Nos. 24-33 and SEQ ID Nos: 1-10.

In a certain embodiment, the sample tested in the method of the present invention is a saliva sample, and the composition further comprises a protease inhibitor selected from the group consisting of Antipain, AC-DEVD-CHO, Aprotinin, Eglin C, GW, PMSF and 2,6 PDA. The sample can be a buccal sample, the composition comprises a protease inhibitor selected from the group consisting of PMSF, GW, aprotinin, eglinC and pepstatin.

In another embodiment, the method of the present invention further comprises contacting the sample with at least one substrate of a viral protease of a virus which is not the SARS-CoV-2, wherein absence of cleavage of the at least one substrate is indicative of the absence of the virus from the sample.

In a further embodiment, the device suitable for reading the signal in the method of the present invention is an optical or spectroscopic device. This optical or spectroscopic device can be modular. In yet further embodiment, the optical or spectroscopic device is configured to operate as a portable and highly sensitive fluorescence spectrophotometer (fluorometer), luminometer, fluorescence microscope or combinations thereof for measuring fluorescence, luminescence or phosphorescence. These optical or spectroscopic devices can be conveniently placed at the entrance to public areas, such as theatres, restaurants and places of work. They can be also miniaturised and used for rapid point-of-care diagnostics in public areas, work places and at home.

In yet another embodiment, the assay can be adapted to a fully automated robotic system. The optical or spectroscopic device comprises a fluorescence reading module, a sample handling mechanism and a dispenser/pipette module. The samples are loaded on to the sample handling mechanism, where it is processed and all reagents are added by the dispenser/pipette module. Then the sample is monitored by fluorescence reading and analysed by designated software. This embodiment is intended for rapid laboratory, high-throughput diagnostics for multiple patients.

In yet further embodiment, the optical or spectroscopic device comprises an excitation module, a sample chamber and an acquisition and/or detector module. The sample chamber can be a fluorescence multiplate reader for laboratory high-throughput and rapid, multiplexing analysis of multiple samples for point-of-care diagnostics.

In a particular embodiment, the optical or spectroscopic device further comprises a computing unit. In another particular embodiment, the acquisition and/or detector module and the computing unit are combined in a single unit designed to perform acquisition of the fluorescence emission, to measure its intensity, to process the fluorescent emission data and optionally display it in a readable format and/or output it to an external memory or user's interface.

In still another particular embodiment, the acquisition module is a part of a smartphone or any other mobile device or gadget suitable for performing the desired measurements.

In some embodiments, the detector is an electron-multiplying charge-coupled device (EMCCD) imager, a charge-coupled device (CCD) imager, an avalanche photodiode (APD), a photomultiplier tube (PMT), scientific complementary metal-oxide-semiconductor (sCMOS) imager, or CMOS imager of a smartphone camera, a stand-alone camera, or a camera of any mobile device or gadget, the detector optionally having a focusing apparatus and a computer link.

In a specific embodiment, the detector is a CMOS imager of a smartphone camera.

In some embodiments, the device suitable for reading the signal is a lateral flow device, which can be in a format of a stick or a stack. In a particular embodiment, the lateral flow device is based on a nitrocellulose membrane or a cellulose (paper) membrane. The lateral flow device is suitable for home use or point of care detection of the virus.

The present invention also provides a microfluidic chip or lab-on-a-chip suitable for carrying out the method of any embodiment of the present invention.

Another aspect of the present invention is an isolated peptide comprising an amino acid sequence as set forth in SEQ ID NOs: 25-33, the peptide being no longer than 14 amino acids. The isolated peptide further comprising a detectable moiety. In a particular embodiment, the isolated peptide consists of an amino acid sequence as set forth in any one of SEQ ID Nos: 2-10.

A further aspect of the present invention is an article of manufacture comprising the isolated peptide of the present invention attached to a solid support. The solid support can be a test tube, microtiter plate, microtiter well, bead, dipstick, polymer microparticle, magnetic microparticle, nitrocellulose, cellulose, or a chip array.

Yet further aspect of the present invention is a diagnostic kit for detection of SARS-CoV-2 in a sample. The kit comprises the isolated peptide or the article of manufacture of the present invention and reagents for detecting cleavage of the peptide. The kit further comprises at least one agent which specifically detects the presence of a virus other than the SARS-CoV-2.

According to another aspect of the present invention, there is provided a method of diagnosing a Severe acute respiratory syndrome coronavirus 2 (SARS-CoV-2) infection in a subject comprising contacting a sample of the subject with a composition comprising an agent that detects 3CL-protease of the SARS-Co-V2 virus, wherein a presence of the 3CL-protease in the sample is indicative of a SARS-Co-V2 infection.

According to another aspect of the present invention, there is provided a method of detecting a SARS-CoV-2 virus in a sample of a subject suspected of having COVID, the method comprising contacting the sample with a composition comprising an agent that monitors the activity of a 3CL protease of the SARS-CoV-2 virus, wherein the activity level of the 3CL protease in the sample is indicative of the presence of SARS-CoV-2 in the sample.

According to embodiments of the present invention, the sample is selected from the group consisting of mucus, saliva, throat wash, nasal wash, spinal fluid, sputum, urine, semen, sweat, feces, plasma, blood, broncheoalveolar fluid, vaginal fluid, tear fluid and tissue biopsy.

According to embodiments of the present invention, the sample is a saliva or buccal sample.

According to embodiments of the present invention, the agent monitors the activity of the 3CL protease.

According to embodiments of the present invention, the agent is a substrate peptide for the 3CL protease, the peptide being attached to at least one moiety which generates a detectable signal on cleavage of the peptide by the 3C-L protease of the SARS-CoV-2.

According to embodiments of the present invention, the peptide is between 10-12 amino acids.

According to embodiments of the present invention, the at least one moiety is a FRET pair, and wherein cleavage of the peptide generates a signal from the FRET pair.

According to embodiments of the present invention, the FRET pair is AF488 and BHQ1.

According to embodiments of the present invention, the FRET pair is EDANS and dabcyl.

According to embodiments of the present invention, the substrate peptide further comprises a separating moiety.

According to embodiments of the present invention, the agent is represented by the general formula:

X—Y—Z wherein:
Y comprises a substrate peptide of a 3CL protease of the SARS-CoV-2, cleavage of X—Y—Z by the 3CL protease forming cleavage products X—Y' and Y"—Z wherein Y' is a first cleavage product of Y and Y" is a second cleavage product of Y;
X comprises a detectable moiety; and
Z comprises a separating moiety capable of binding to a separate phase of a two phase separating system;
wherein the X—Y—Z does not form a contiguous portion of a natural substrate of the 3CL protease. According to embodiments of the present invention, the detectable moiety X comprises a labeling agent selected from the group consisting of an enzyme, a fluorophore, a chromophore, a protein, a pre-enzyme, a chemiluminescent substance and a radioisotope.

According to embodiments of the present invention, the separating moiety Z is selected from the group consisting of an immunological binding agent, a magnetic binding moiety, a peptide binding moiety, an affinity binding moiety and a nucleic acid moiety.

According to embodiments of the present invention, the substrate peptide comprises an amino acid sequence selected from the group consisting of SEQ ID Nos: 13-23.

According to embodiments of the present invention, the substrate peptide comprises an amino acid sequence as set forth in SEQ ID NO: 13.

According to embodiments of the present invention, the amino acid sequence of the substrate peptide consists of a sequence selected from the group consisting of SEQ ID Nos. 24-33.

According to embodiments of the present invention, the substrate peptide is as set forth in the sequence selected from the group consisting of SEQ ID Nos: 1-10.

According to embodiments of the present invention, the substrate peptide is as set forth in SEQ ID NO: 8.

According to embodiments of the present invention, the substrate peptide is attached to a fluorescent moiety.

According to embodiments of the present invention, when the sample is a saliva sample, the composition comprises a protease inhibitor selected from the group consisting of Antipain, AC-DEVD-CHO, Aprotinin, Eglin C, GW, PMSF and 2,6 PDA.

According to embodiments of the present invention, the protease inhibitor comprises PMSF and GW.

According to embodiments of the present invention, when the sample is a buccal sample, the composition comprises a protease inhibitor selected from the group consisting of PMSF, GW, aprotinin, eglinC and pepstatin.

According to embodiments of the present invention, the protease inhibitor comprises PMSF, GW, aprotinin and eglinC.

According to embodiments of the present invention, the method further comprises contacting the sample with at least one substrate of a viral protease of a virus which is not the SARS-CoV-2, wherein absence of cleavage of the at least one substrate is indicative of the absence of the virus from the sample.

According to another aspect of the present invention, there is provided an isolated peptide comprising an amino acid sequence as set forth in SEQ ID NOs: 25-34, the peptide being no longer than 14 amino acids.

According to embodiments of the present invention, the isolated peptide further comprises a detectable moiety.

According to embodiments of the present invention, the isolated peptide consists of an amino acid sequence as set forth in any one of SEQ ID Nos: 2-10.

According to another aspect of the present invention, there is provided an article of manufacture comprising the isolated peptide described herein attached to a solid support.

According to embodiments of the present invention, the solid support is a bead.

According to another aspect of the present invention, there is provided a diagnostic kit for detection of SARS-CoV-2 in a sample, the kit comprising the peptide described herein, or the article of manufacture described herein and reagents for detecting cleavage of the peptide.

According to embodiments of the present invention, the diagnostic kit further comprises at least one agent which specifically detects the presence of a virus other than the SARS-CoV-2.

According to another aspect of the present invention, there is provided a method of treating a SARS-CoV-2 infection of a subject in need thereof comprising:
(a) diagnosing a SARS-CoV-2 infection in the subject according to the method of claim 2; and
(b) treating the subject.

Various embodiments may allow various benefits and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE SEVERAL VIEWS OF THE DRAWINGS

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

(6) Blank lane.

(7+8) Non-purified, TEV-cleaved SARS-CoV-2 3CLpro at 4° C. and 30° C. respectively. TEV-protease (28 kDa) is visible.

(9+10) Elution of proteins bound to Histrap column after TEV-cleavage at 4° C. and 30° C. respectively. TEV-protease is visible and a small amount of what is probably uncleaved SARS-CoV-2-3CLpro.

Figure 3B:
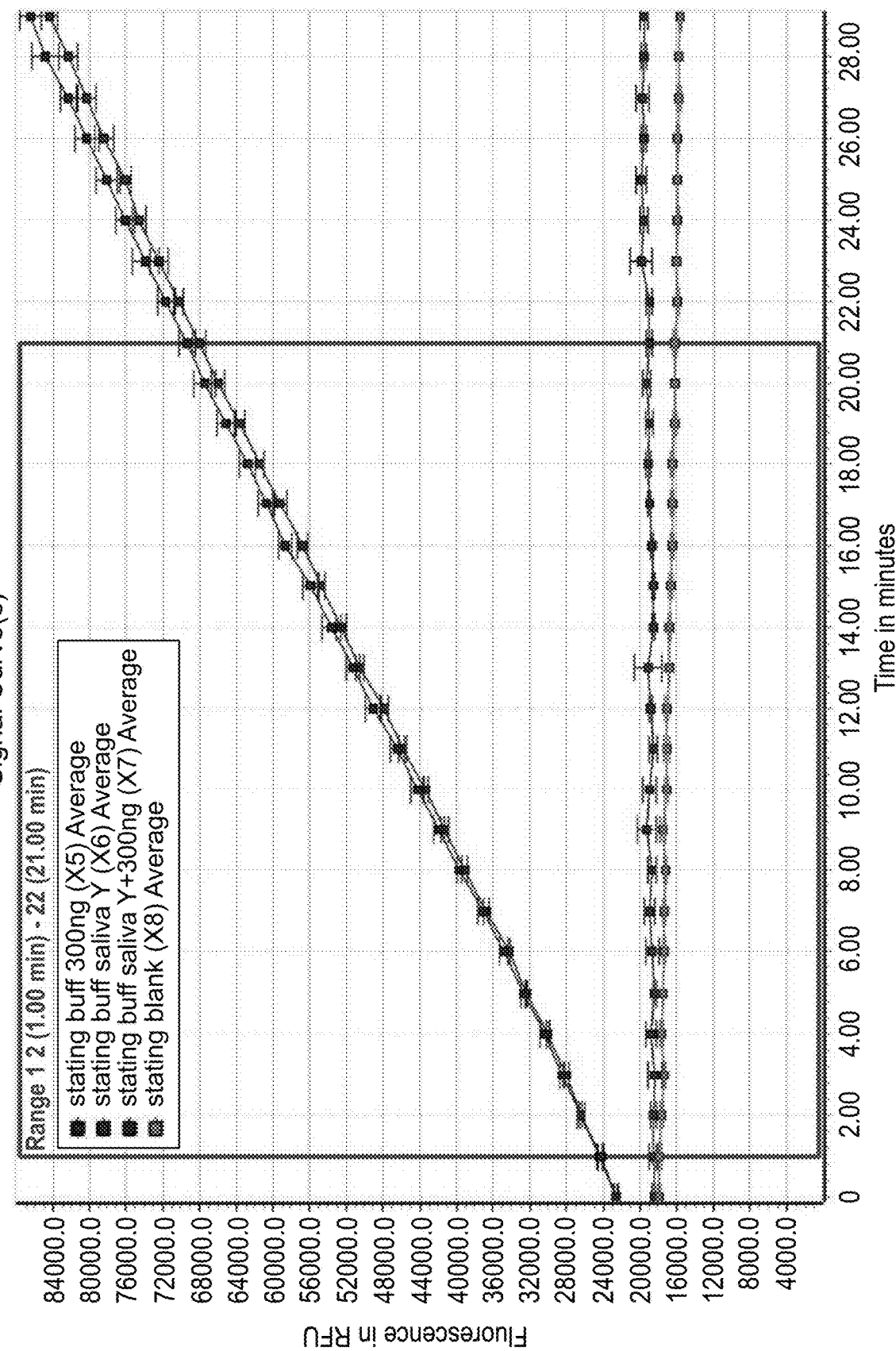

FIGS. 3A-3C show the spike effect in saliva sample Y:
FIG. 3A—commercial buffer.
FIG. 3B—starting buffer.
FIG. 3C—final buffer.

Figure 4:
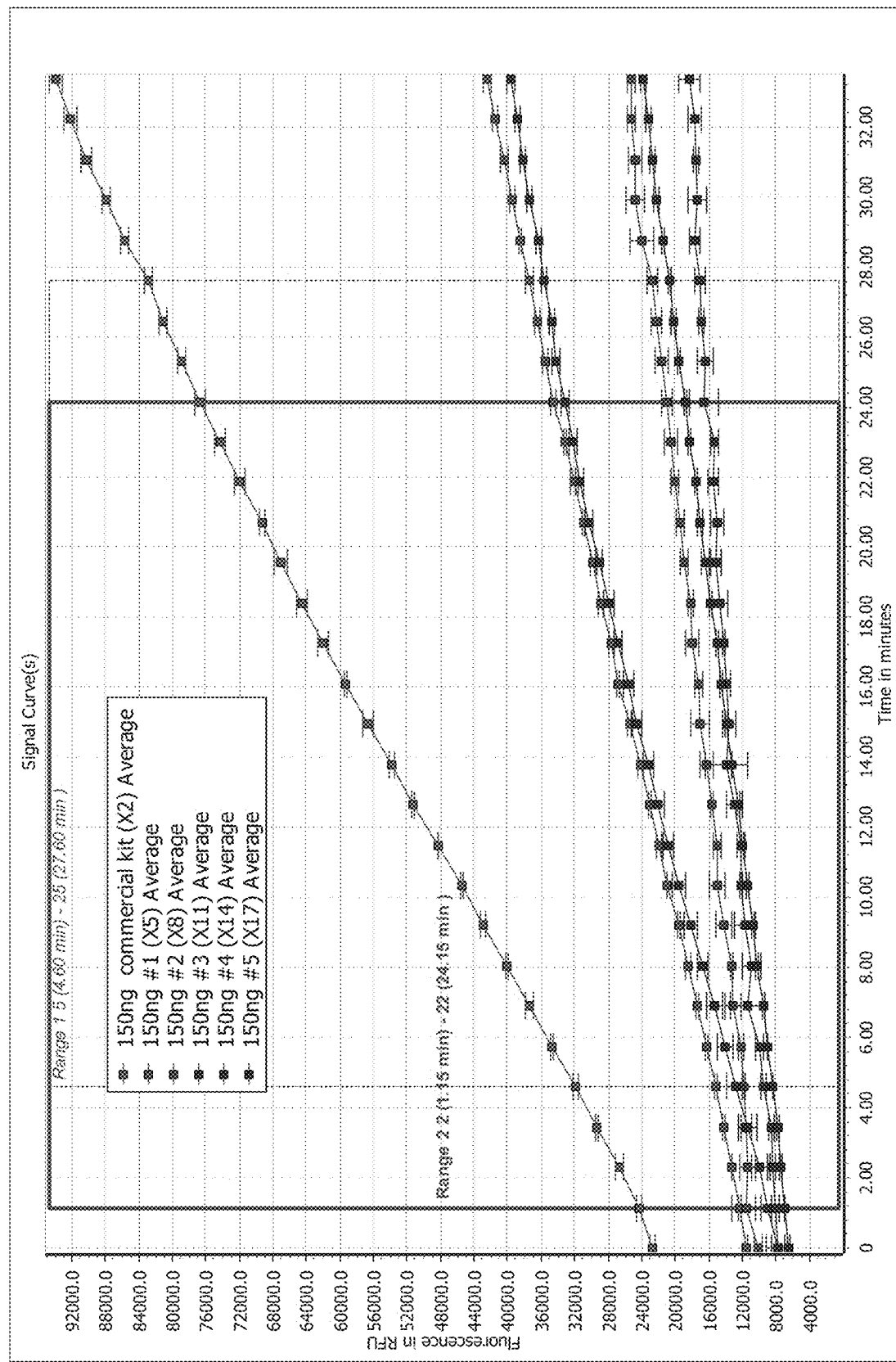
Figure 5B:
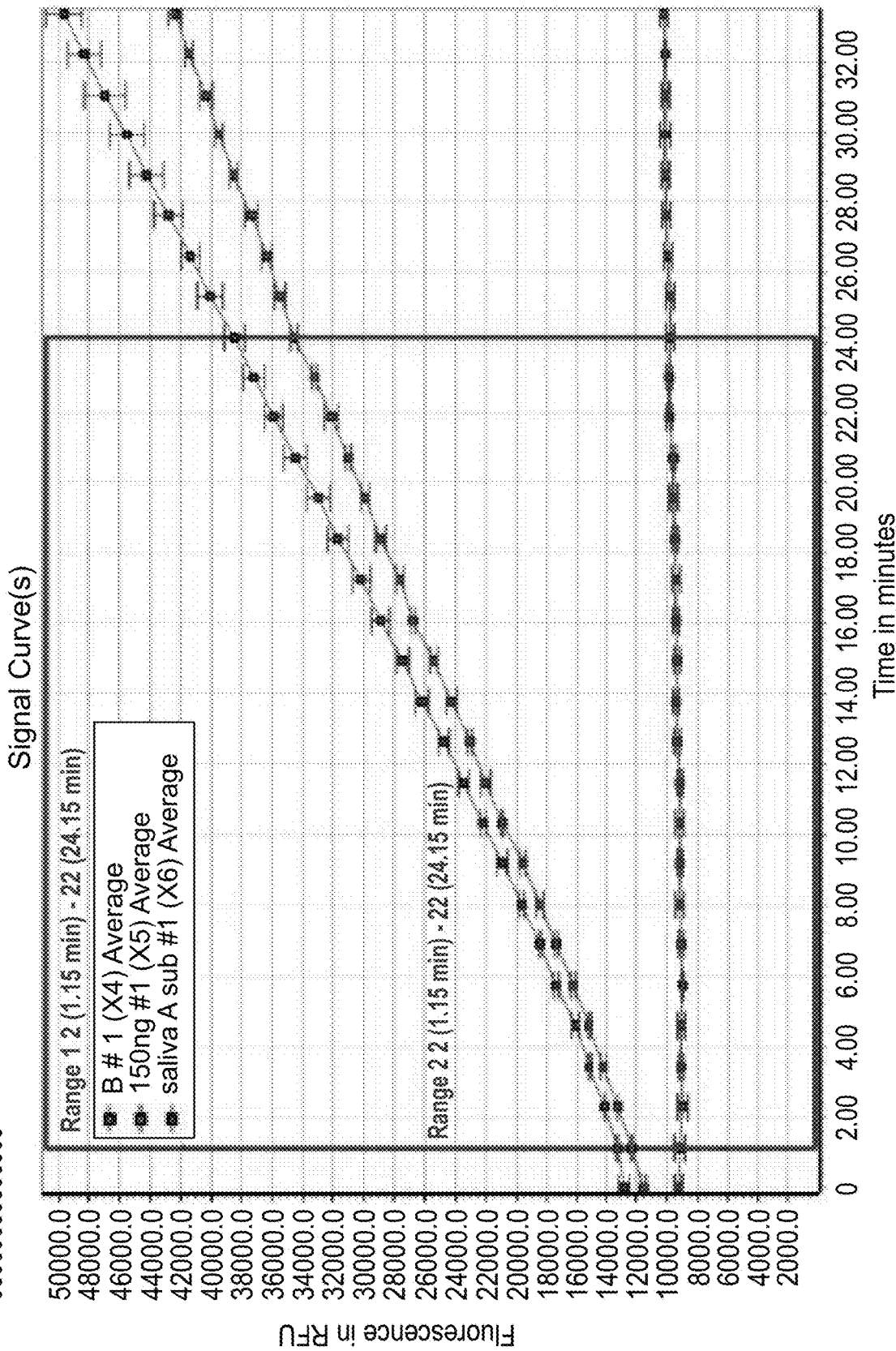

FIG. 4 shows the graph comparing the 3CLPro activity of five different substrates (SEQ ID NOs: 2-6) and a commercially available substrate (SEQ ID NO: 1).

FIGS. 5A-5F show the graphs illustrating 3CLPro and Saliva activity using five different test substrates (SEQ ID NOs: 2-6) and a commercially available substrate (SEQ ID NO: 1).

Figure 6:
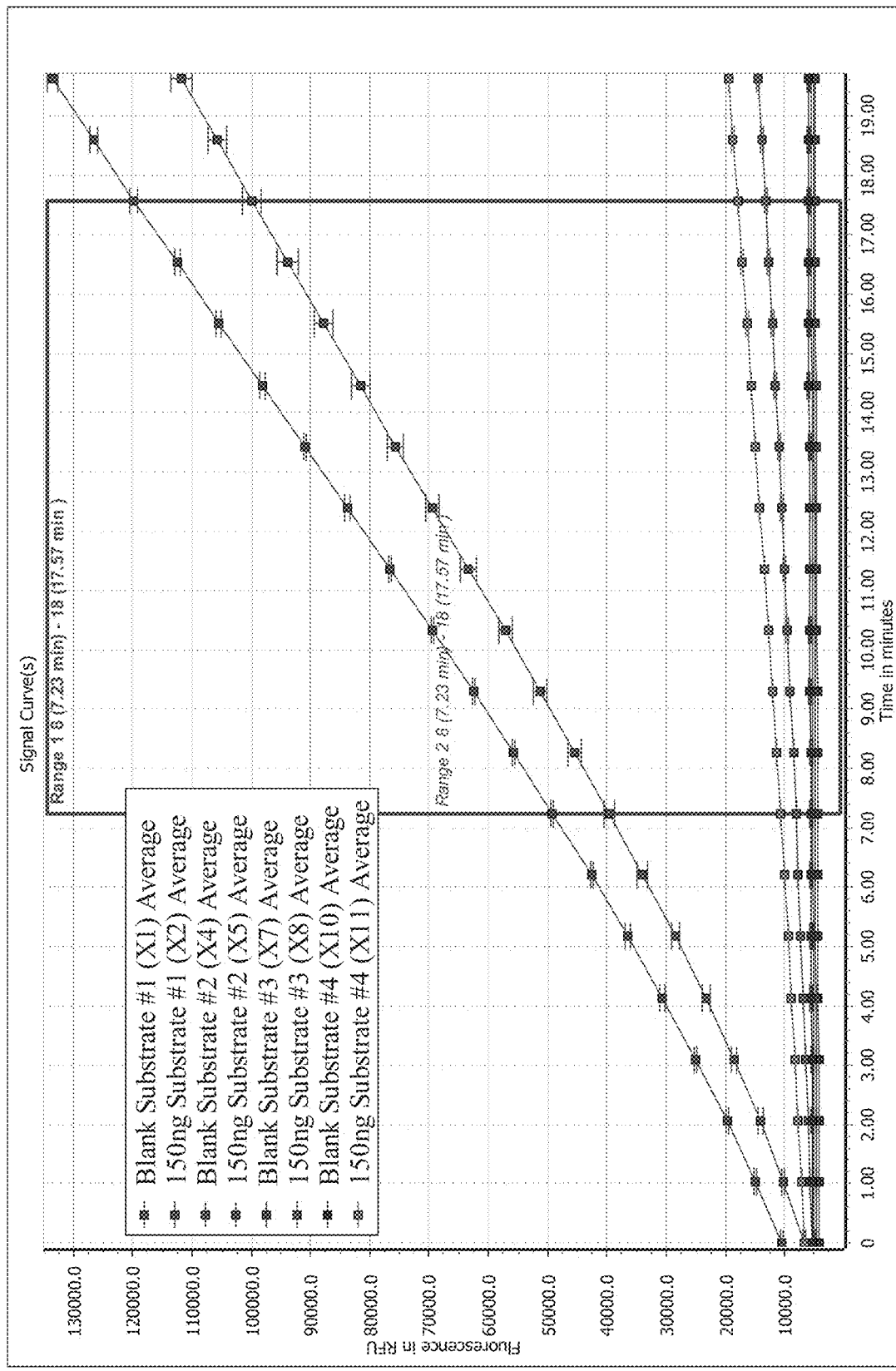
Figure 7B:
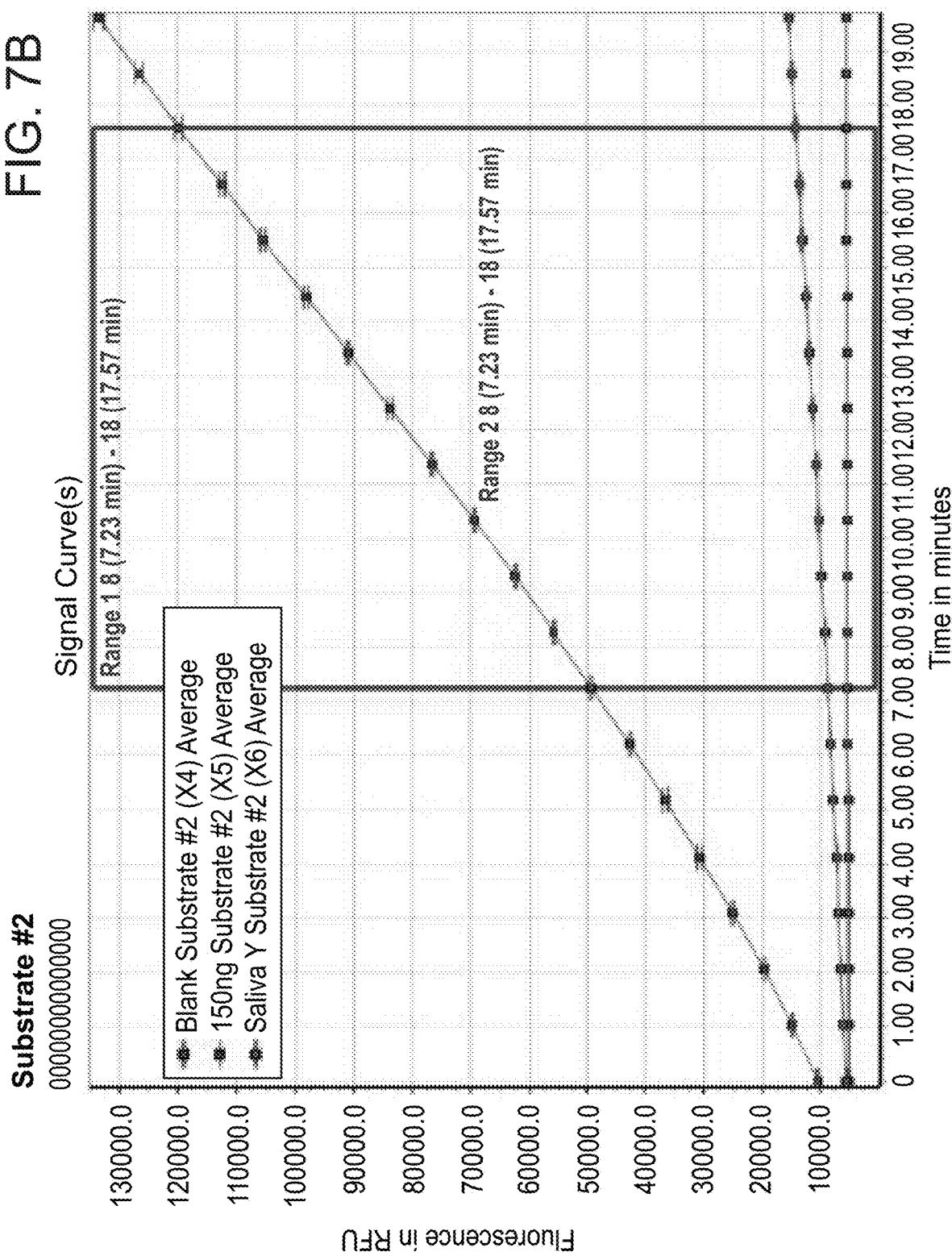

FIG. 6 shows the graph comparing the 3CLPro activity of four different substrates (SEQ ID NOs: 7-10).

FIGS. 7A-7D show the graphs illustrating 3CLPro and Saliva activity using four different substrates (SEQ ID NOs: 7-10).

Figure 8:
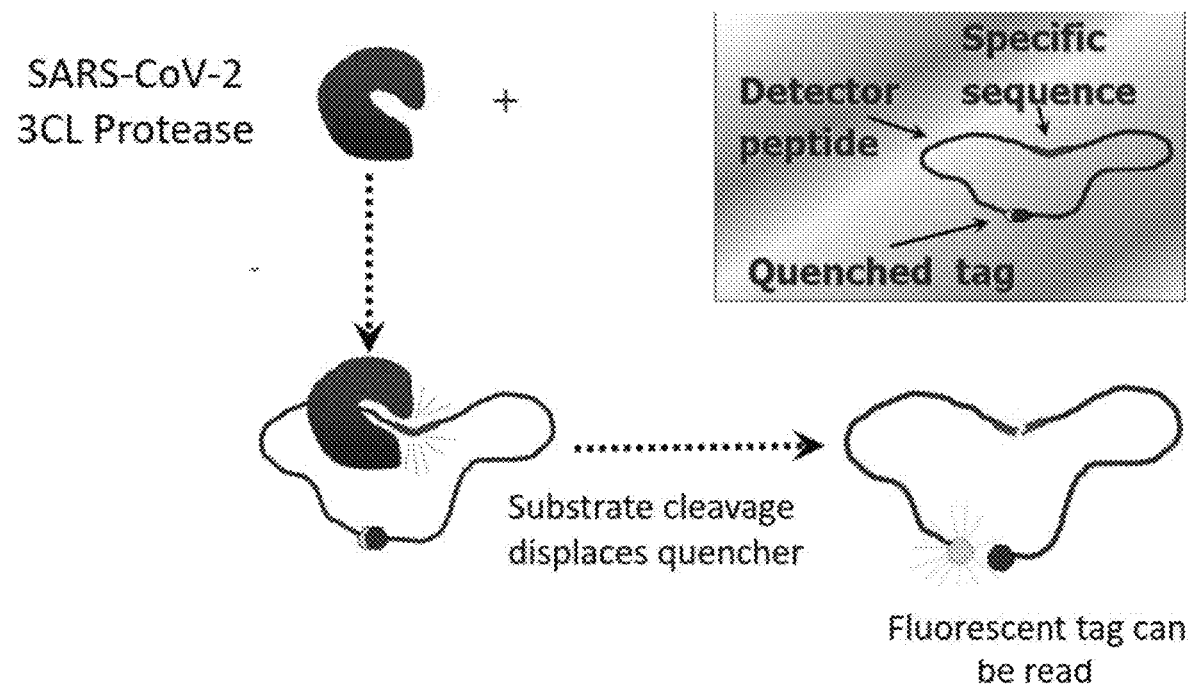

FIG. 8 schematically shows the detection mechanism behind the method of the present invention.

Figure 9:
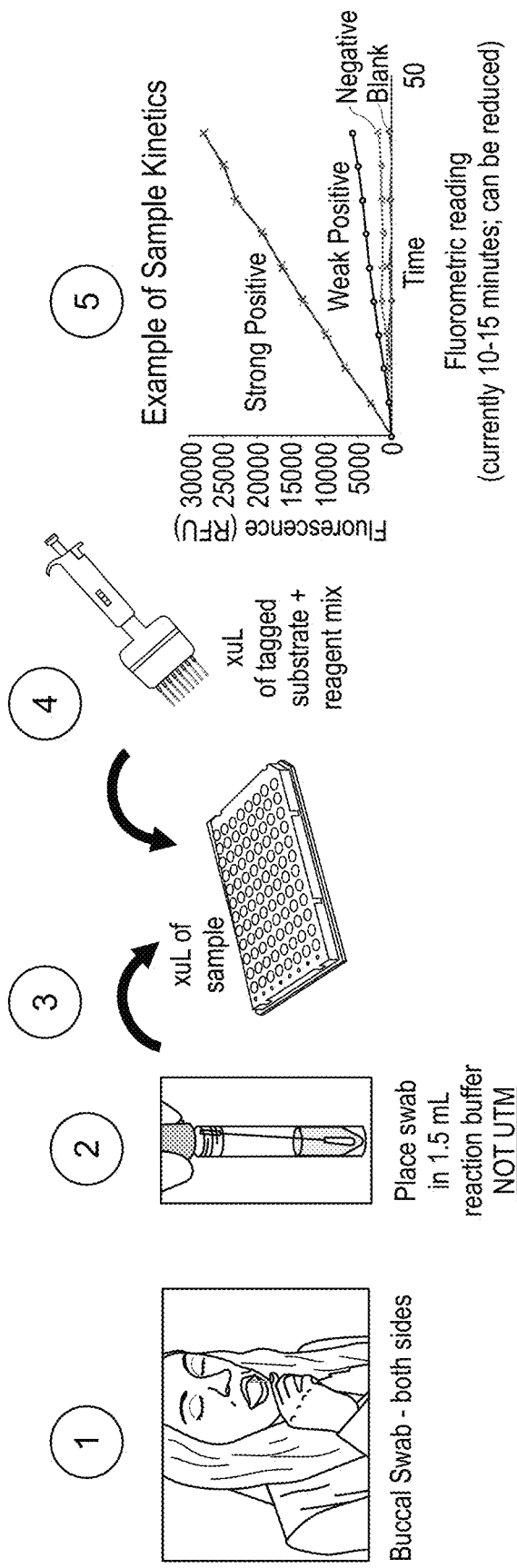

FIG. 9 demonstrates the enzyme activity test for the SARS-CoV-2 detection using the method of the present invention.

Figure 10:
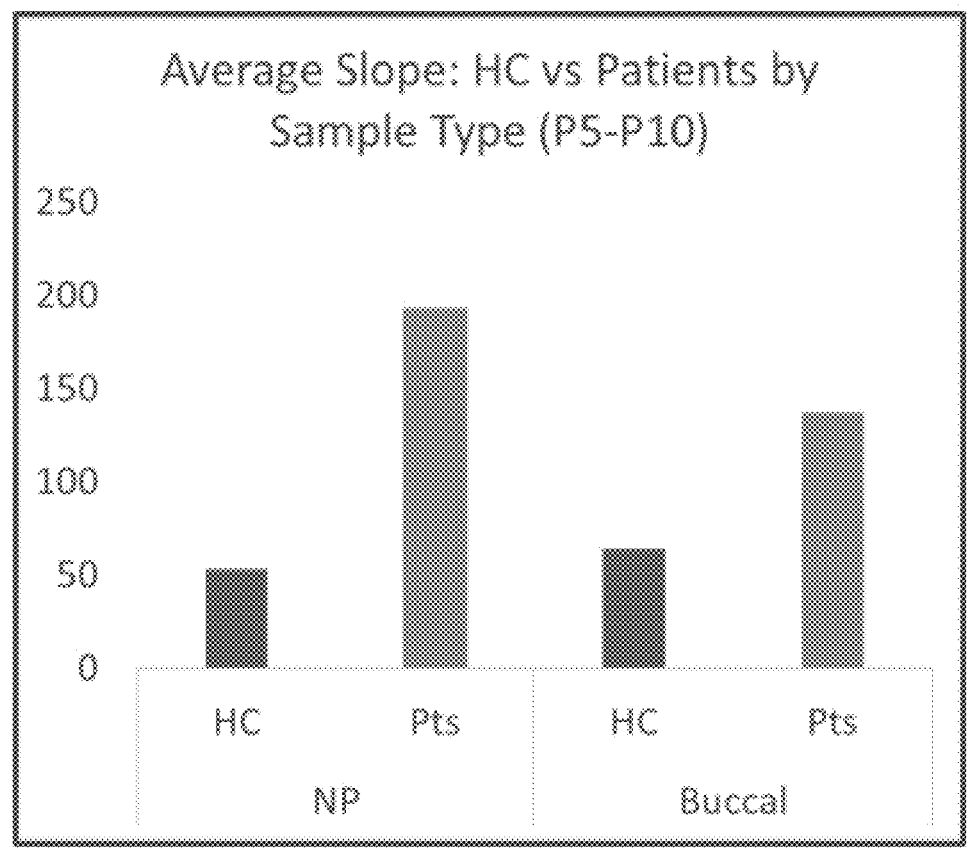

FIG. 10 shows buccal vs nasopharyngeal (NP) samples test results. Bars represent mean slope values for five healthy control (HC) samples vs six patient samples comparing matched nasopharyngeal and buccal samples from each subject.

Figure 11:
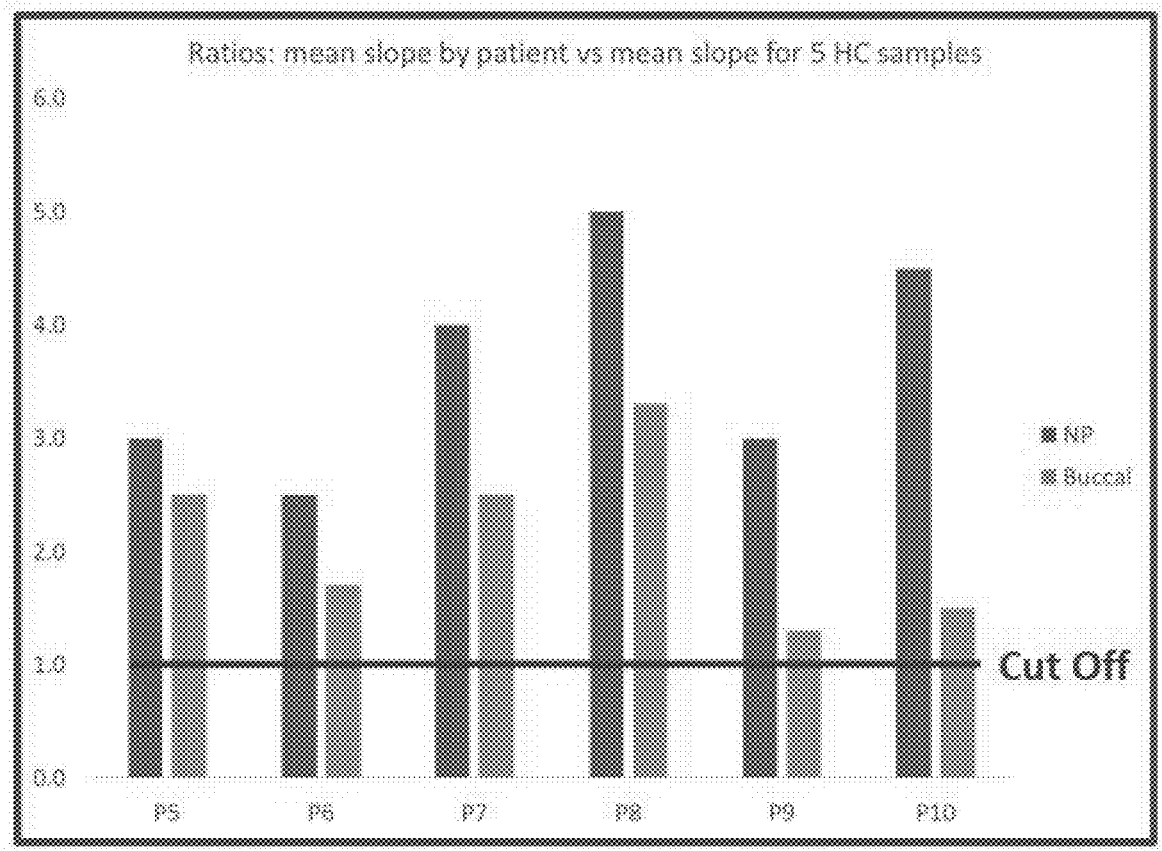

FIG. 11 shows buccal vs nasopharyngeal (NP) samples test results.

Figure 12:
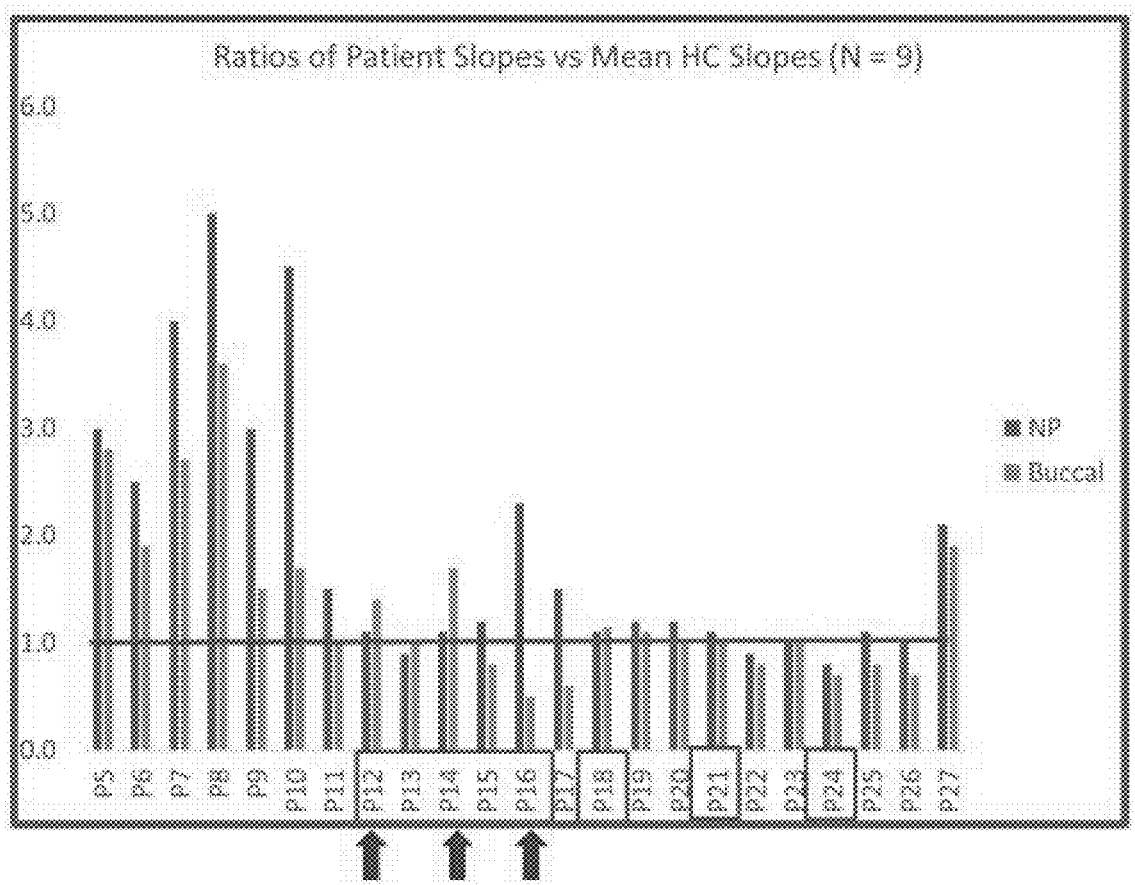

FIG. 12 shows overlaying results with patient discharge. The boxes (P12-P16, P18, P21 and P24) indicate patients who were discharged within 48 hours of the protease assay result. At least three patient samples still showed significant protease activity above controls. These results clearly show that patient discharge on the basis of PCR values or resolution of clinical symptoms should be reconsidered.

Figure 13:
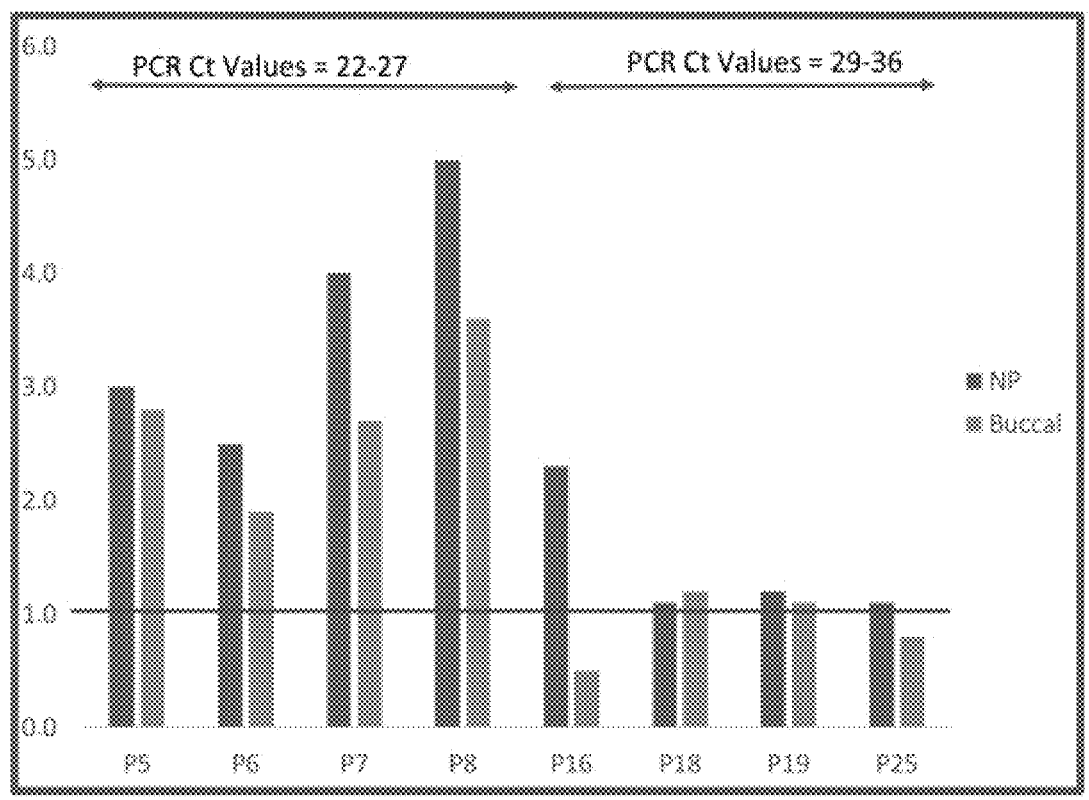

FIG. 13 shows the correlating results with the PCR CT (cycle threshold) values. Bars represent mean slope ratios for seven patient samples from whom matching PCR CT values were determined within 48 hours of sample collection for the 3CL protease assay. The 3CL protease results track with the Ct values, which may act as a surrogate measure of viral load.

Figure 14:
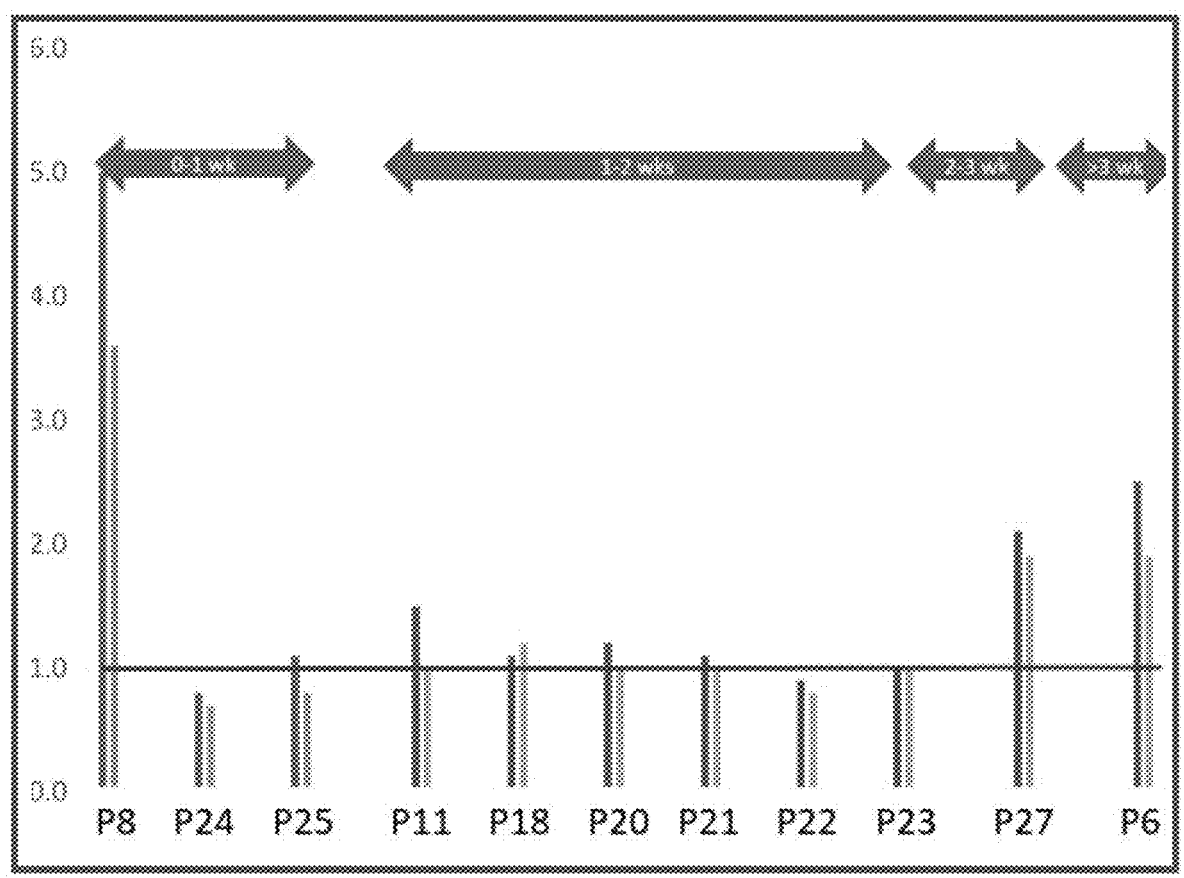

FIG. 14 shows the overlay of the assay results vs days since symptom onset. Evidence of active 3CL protease can still be seen in specimens from individuals whose symptoms first arose more than 3 weeks prior to testing.

Figure 15:
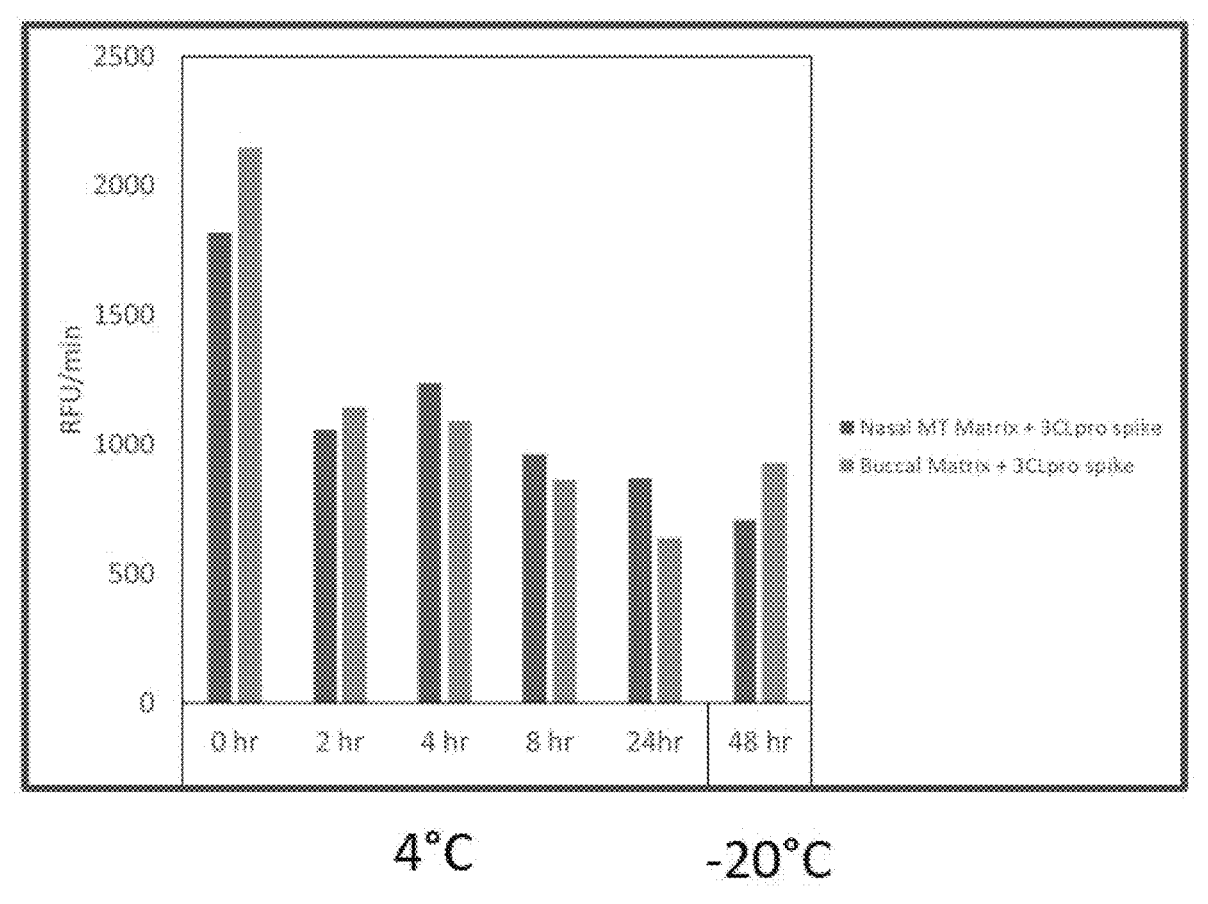

FIG. 15 shows the sample stability profile. Samples held at 4° C. retained ~40-50% of the enzymatic activity above background through 24 h. The most significant reduction occurred between 0-2 hrs. Samples held at −20° C. from time 0 retained activity even at 48 hrs. Buccal and nasal (mid turbinate) matrices yielded comparable results.

Figure 16:
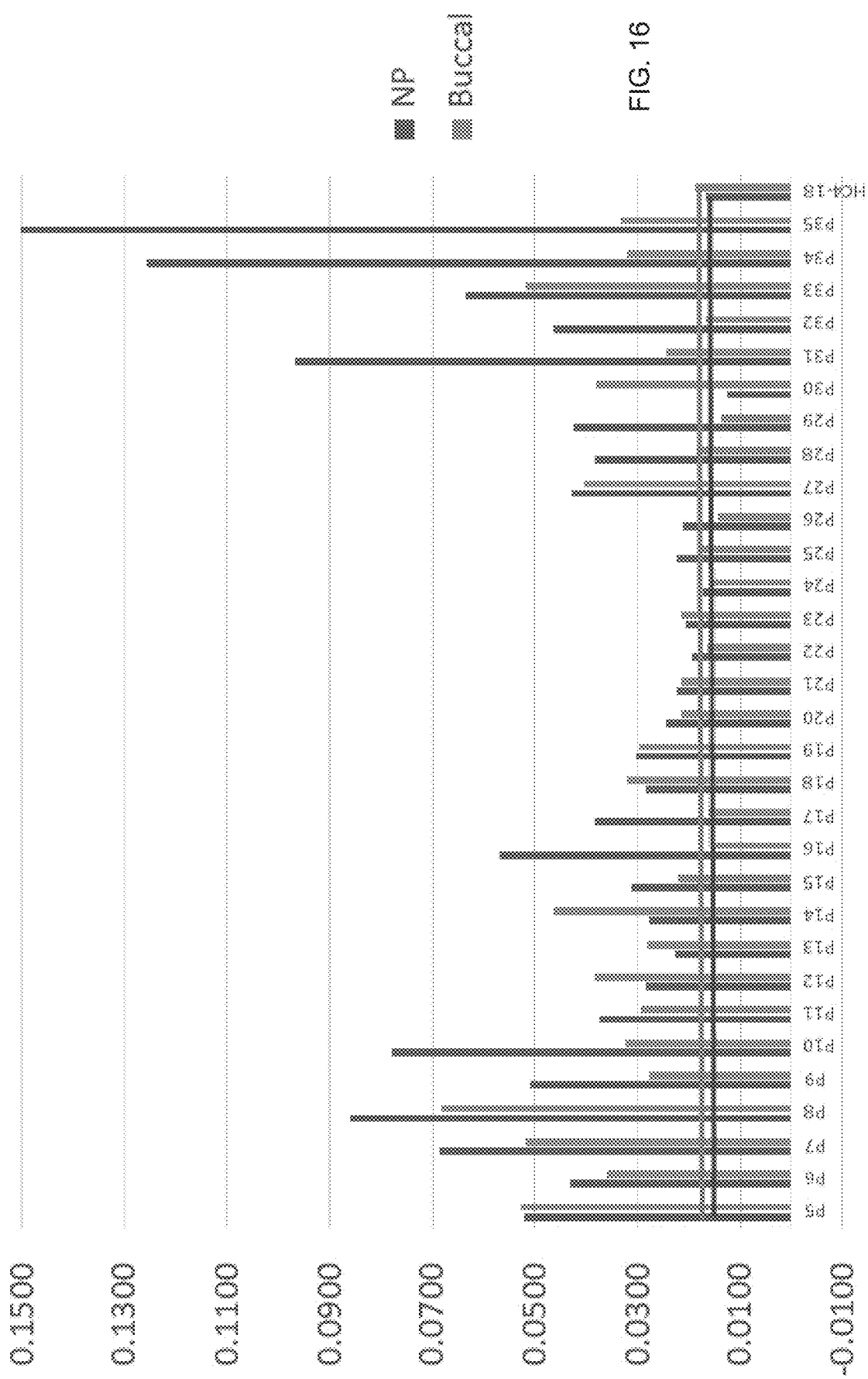

FIG. 16 is a graph showing the ratio of patient sample slopes vs. mean control protease slope within the experimental set of 25 positive Covid-19 patients.

Figure 17A:
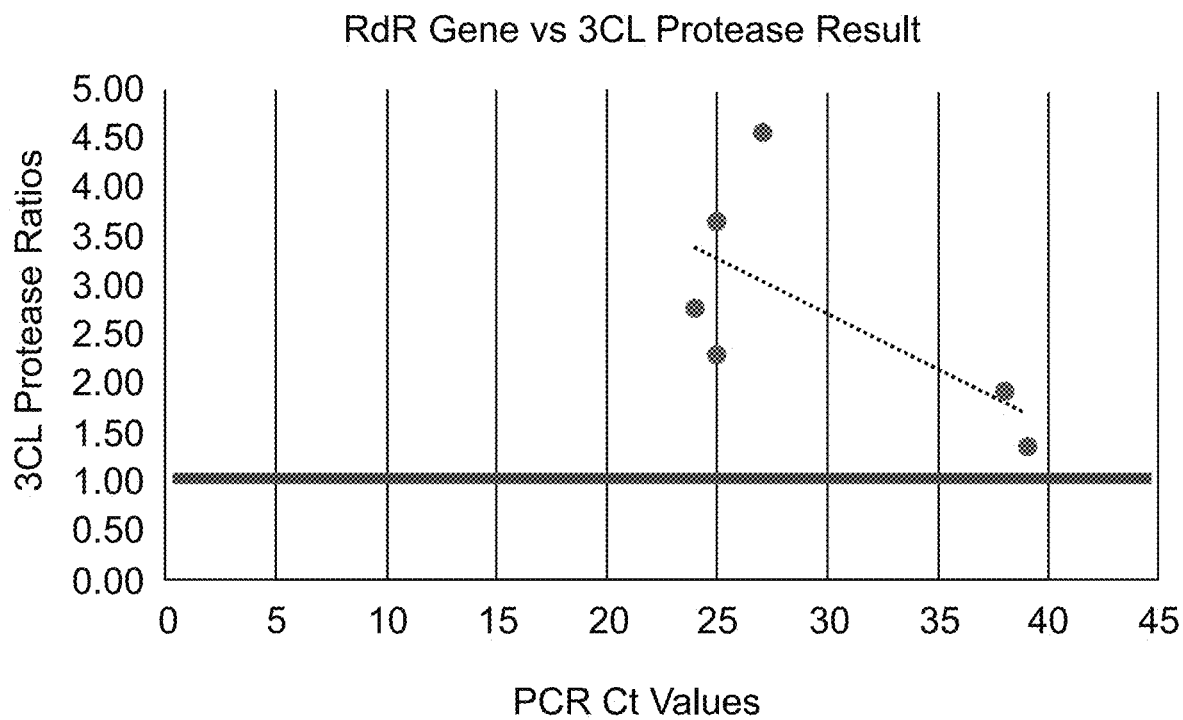
Figure 17B:
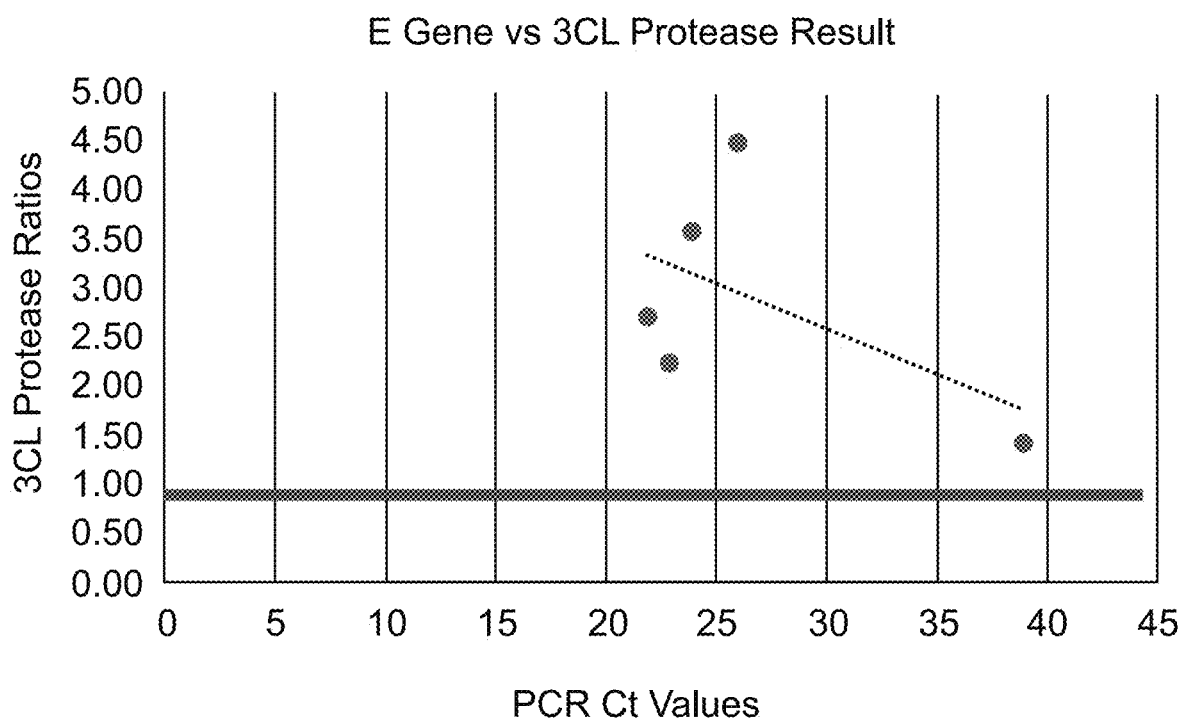
Figure 17C:
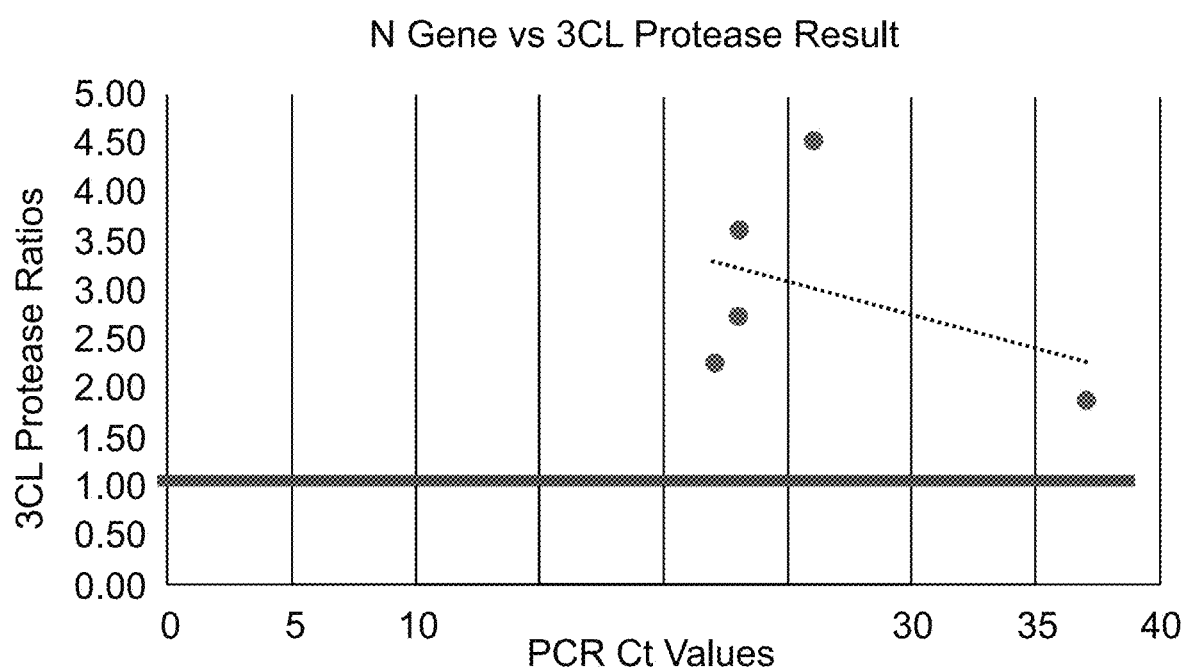

FIGS. 17A-C are graphs illustrating the sensitivity of the assay compared to the sensitivity of a PCR assay for various genes.

DESCRIPTION OF SPECIFIC EMBODIMENTS OF THE INVENTION

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, is "open ended" and means the elements recited, or their equivalent in structure or function, plus any other element or elements which are not recited. It should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a composition comprising x and z" should not be limited to compositions consisting only of components x and z. Also, the scope of the expression "a method comprising the steps x and z" should not be limited to methods consisting only of these steps. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure. Unless specifically stated, as used herein, the term "about" is understood as within a range of normal tolerance in the art, for example within two standard deviations of the mean. In one embodiment, the term "about" means within 10% of the reported numerical value of the number with which it is being used, preferably within 5% of the reported numerical value. For example, the term "about" can be immediately understood as within 10%, 9%, 8%, 7%, 6%, 5%, 4%, 3%, 2%, 1%, 0.5%, 0.1%, 0.05%, or 0.01% of the stated value. In other embodiments, the term "about" can mean a higher tolerance of variation depending on for instance the experimental technique used. Said variations of a specified value are understood by the skilled person and are within the context of the present invention. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges, for example from 1-3, from 2-4, and from 3-5, as well as 1, 2, 3, 4, 5, or 6, individually. This same principle applies to ranges reciting only one numerical value as a minimum or a maximum. Unless otherwise clear from context, all numerical values provided herein are modified by the term "about". Other similar terms, such as "substantially", "generally", "up to" and the like are to be construed as modifying a term or value such that it is not an absolute. Such terms will be defined by the circumstances and the terms that they modify as those terms are understood by those of skilled in the art. This includes, at very least, the degree of expected experimental error, technical error and instrumental error for a given experiment, technique or an instrument used to measure a value. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition. As used herein, the term "diagnosing" refers to determining presence or absence of the virus in the subject, classifying the infection, determining a severity of the infection, monitoring virus progression, forecasting an outcome of a pathology and/or prospects of recovery and/or screening of a subject for the virus.

As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity. As used herein, the singular form "a", "an" and "the" include plural references unless the context clearly dictates otherwise. For example, the term "a compound" or "at least one compound" may include a plurality of compounds, including mixtures thereof.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The present invention provides a method, reagents and a kit for the detection of SARS-CoV-2 in a test sample and involves the detection of the 3C-L protease. The present invention directs at diagnosing COVID-19 using the 3C-L protease assay that selectively detects active forms of a SARS-CoV-2-encoded enzyme that is required for viral replication and transmission, and which may also play a role in cellular apoptosis. Detection of live viruses (as opposed to viral fragments) further allows for the ability to diagnose infectivity status.

Whilst reducing the present invention to practice, the present inventors have shown that the SARS-CoV-2 virus can be identified in upper respiratory and oral samples derived from both asymptomatic and symptomatic patients. The activity assay provides results within <15 minutes (see FIGS. 3A-C, 4, 5A-F, 6 and 7A-D). Furthermore, the present inventors were able to detect persistent, active viral reservoirs in recovering individuals, including early-stage symptomatic and asymptomatic individuals.

Whilst further reducing the present invention to practice, the present inventors demonstrated they could detect 3CL protease activity from additional coronaviruses (Tables 4-6). The ability to deploy a mechanism-based assay that can detect different coronaviruses ensures that the assay performance will not decrease, even as new mutations arise. The assay was shown to be specific for identifying coronaviruses and not picornaviruses (see Tables 4-6).

Both the speed in which the test can be carried out, together with its high accuracy makes the test particularly suitable for point-of-care (POC) rapid diagnostics in highly populated locations (e.g., nursing homes and schools). Since the test reliably identifies asymptomatic individuals, the test is also suitable for use in the travel industry and for healthcare workers. Population monitoring via testing of waste water/pooled samples can also be carried out using the proposed diagnostic test. The assay format may be easily adapted for in-home testing.

Thus, according to a first aspect of the present invention there is provided a method of diagnosing a Severe Acute Respiratory Syndrome Coronavirus 2 (SARS-CoV-2) infection in a sample of a subject, the method comprising contacting the sample with a composition comprising an agent that detects 3CL-protease of the SARS-Co-V2 virus, wherein a presence of said 3CL-protease in the sample is indicative of a SARS-Co-V2 infection.

In another embodiment, the method of detecting a SARS-CoV-2 virus in a sample of a subject suspected of having COVID-19 comprises contacting the sample with a composition comprising an agent that monitors the activity of a 3CL protease of the SARS-CoV-2 virus, wherein the activity level of said 3CL protease in the sample is indicative of the presence of SARS-CoV-2 in the sample. The activity level may also allow quantification of the SARS-CoV-2 virus in the sample.

In some embodiments, the detectable moiety is a fluorescence moiety. In a particular embodiment, the detectable moiety is a Förster Resonance Energy Transfer (FRET) pair of donor and acceptor moieties, and the cleavage of the substrate peptide generates or modulates a signal from said FRET pair. Specific donor moiety is a quantum dot.

In a further aspect, the present invention provides a method of a heterogeneous assay, in which the solid-phase is separated from another assay component during the assay, for biomolecular diagnostics of a SARS-CoV-2 virus in a sample of a subject suspected of having COVID-19, the method comprising:

(A) Contacting the sample with a composition comprising a cleavable agent represented by the general formula:

X—Y—Z, wherein:
i) Y is a substrate peptide capable of being cleaved by the SARS-CoV-2 3CL protease;
ii) cleavage of X—Y—Z by said 3CL protease forms products X—Y' and Y"—Z of the cleavage, wherein Y' and Y" are two cleavage fragments of said substrate peptide Y;

iii) Z is an optional separating moiety capable of binding to a separate phase of a two-phase separating system;

iv) said cleavable agent X—Y—Z does not form a contiguous portion of a natural substrate of said 3CL protease; and v) X is a detectable moiety capable of generating a detectable signal on cleavage of the substrate peptide by said 3CL protease, thereby monitoring activity of the 3CL protease in the sample, wherein the activity level of the 3CL protease that correlates to said detectable signal is i) indicative of the presence of the SARS-CoV-2 virus in the sample, and ii) allows quantification of the SARS-CoV-2 virus in the sample; and (B) Recording or reading said signal with a device suitable for reading this signal.

In some embodiments, the detectable moiety X comprises a labelling agent selected from the group consisting of an enzyme, a fluorophore, a chromophore, a protein, a pre-enzyme, a chemiluminescent substance and a radioisotope. The separating moiety Z is selected from the group consisting of an immunological binding agent, magnetic binding moiety, peptide binding moiety, affinity binding moiety, nucleic acid moiety, biotin/streptavidin moiety, quantum dots, metamaterials, conductive polymeric moiety, dendrimer moiety, crown ether or imprinting polymer moiety, aptamer moiety, electrochemical binding moiety, and metallic nanoparticle moiety.

In particular embodiments, the sample is selected from the group consisting of mucus, saliva, throat wash, nasal wash, spinal fluid, sputum, urine, semen, sweat, faeces, plasma, blood, bronchioalveolar fluid, vaginal fluid, tear fluid, tissue biopsy, and nasopharyngeal, oropharyngeal, nasal mid turbinate, anterior nasal and buccal swabs.

In other embodiments, the detectable moiety X is a fluorescence moiety. In a particular embodiment, the detectable moiety X is a Förster Resonance Energy Transfer (FRET) pair of donor and acceptor moieties, and the cleavage of the substrate peptide generates or modulates a signal from said FRET pair. Specific donor moiety is a quantum dot. FIG. 8 schematically shows the detection mechanism behind this method of the present invention. FIG. 9 demonstrates the enzyme activity test for the SARS-CoV-2 detection using the method of the present invention.

In certain embodiments, the donor and acceptor moiety are attached to the peptide in a configuration that permits energy transfer from the donor to the acceptor to result in quenching of the fluorescence by FRET process. In some other embodiments, the donor and acceptor moiety are separated by no more than 3, 5, 10, 15 or 20 amino acid residues.

Subjects which can be tested according to this aspect of the present invention may be symptomatic or asymptomatic of the infection. They may be contagious or non-contagious with the infection. It will be appreciated that the very high accuracy and sensitivity of the assay allows for the detection of very low levels of the SARS-CoV-2 virus. Thus, the method may be used to detect the virus in samples of subjects very soon after initial infection or even in samples tested to be negative by other means (clinical assessments, molecular-, antigen-, antibody-based tests), but which still contain low levels of active virus. Furthermore, the method may be used to detect the virus in samples of asymptomatic subjects.

In a particular embodiment, the method of the present invention is carried on a sample taken from a subject who does not show symptoms of COVID-19, no more than one day following exposure to a subject known to have COVID.

In another particular embodiment, the method of the present invention is carried on a sample taken from a subject who does not show symptoms of COVID-19, no more than two days following exposure to a subject known to have COVID-19.

In still other particular embodiment, the method of the present invention is carried on a sample taken from a subject who does not show symptoms of COVID-19, no more than three days following exposure to a subject known to have COVID-19.

In a further particular embodiment, the method of the present invention is carried on a sample taken from a subject who does not show symptoms of COVID-19, no more than four days following exposure to a subject known to have COVID-19.

In yet further particular embodiment, the method of the present invention is carried on a sample taken from a subject who does not show symptoms of COVID-19, no more than five days following exposure to a subject known to have COVID-19.

In a particular embodiment, the method of the present invention is carried on a sample taken from a subject who does not show symptoms of COVID-19, no more than six days following exposure to a subject known to have COVID-19.

In another particular embodiment, the method of the present invention is carried on a sample taken from a subject who does not show symptoms of COVID-19, no more than seven days following exposure to a subject known to have COVID-19.

In still another particular embodiment, the method of the present invention is carried on a sample taken from a subject who does not show symptoms of COVID-19, more than seven days following exposure to a subject known to have COVID-19.

In a further particular embodiment, the method of the present invention is carried on a sample taken from a subject having a negative PCR test or a positive PCR test with a cycle threshold CT40 and less.

The 3CL protease of the SARS-CoV-2 virus is a 34 kD trypsin-like cysteine protease. According to a particular embodiment, the 3CL protease comprises an amino acid sequence as set forth in SEQ ID NO: 34.

Exemplary samples in which SARS-CoV-2 can be detected include, but are not limited to saliva, mucous, throat wash, nasal wash, spinal fluid, sputum, urine, semen, sweat, feces, plasma, blood, bronchioalveolar fluid, vaginal fluid, tear fluid and tissue biopsy.

In some embodiments, the sample is a sewage sample.

In other embodiments, the sample comprises saliva.

The sample may be taken from the mouth, back of the throat or from inside the cheek (e.g., using a buccal swab).

Examples of swabs which can be used to obtain the sample include cheek swabs, oropharyngeal and nasal pharyngeal swabs.

In order to determine the activity of the 3CL of the SARS-CoV-2 virus, a peptide may be used which serves as a substrate for the enzyme. The peptide is attached to at least one moiety which generates a detectable signal on cleavage by the 3CL protease.

The peptide is typically between 8-30 amino acids long, more preferably between 10 and 20 amino acids long and even more preferably between 10 and 15 amino acids long. According to a particular embodiment, the peptide is no longer than 14 amino acids long. According to a particular embodiment, the peptide is between 8-12 amino acids long.

The peptides described herein may include natural or non-naturally occurring amino acids.

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables A and B below list naturally occurring amino acids (Table A), and non-conventional or modified amino acids (e.g., synthetic, Table B) which can be used with some embodiments of the invention. It will be appreciated that non-conventional amino acids may be used in order to reduce background noise in the assay.

TABLE A

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE B

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nrnhphe |
| α-naphthylalanine | Anap | N-methyl-α-naphthylalanine | Nmanap |

TABLE B-continued

| Non-conventional amino acid | Code | Non-conventional amino acid | Code |
| --- | --- | --- | --- |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl)-carbamylmethyl-glycine | Nnbhm |
| N-(3,3-diphenylpropyl)glycine | Nbhe | N-(N-(3,3-diphenylpropyl)-carbamylmethyl-glycine | Nnbhe |
| 1-carboxy-1-(2,2-diphenylethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The amino acid sequence of the peptide is selected such that it can be cleaved by the 3CL of SARS-CoV-2. Preferably, the peptide does not serve as a substrate for the 3C of Human Rhinovirus (HRV) under the same assay conditions in human samples. In another embodiment, the peptide is selected such that it can distinguish between the 3CL activity of SARS-CoV-2 and other human pathogens in the Coronavirus family (e.g. CoV-229E) in human samples under identical assay conditions.

According to a particular embodiment, the peptide comprises at least one of the amino acid sequences set forth in SEQ ID NOs: 13-23.

In another embodiment, the peptide comprises an amino at least 90% identical to the sequence as set forth in SEQ ID Nos: 13-23.

According to a particular embodiment, the peptide comprises the amino acid sequence as set forth in SEQ ID NO: 13.

Exemplary peptide sequences which comprise the amino acid sequence as set forth in SEQ ID NO: 13 which have been shown to be effective substrates of the 3CL of SARS-CoV-2 are set forth in SEQ ID NOs: 24-33.

In a particular embodiment, the peptides used in the assay have an amino acid sequence at least 90% identical to the sequences as set forth in SEQ ID Nos: 24-33.

In another embodiment, the peptides used in the assay have an amino acid sequence at least 90% identical to the sequences as set forth in SEQ ID Nos: 1-12.

The amino acids of the peptides of the present invention may be substituted either conservatively or non-conservatively.

According to a particular embodiment the amino acids of the peptides are substituted conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH.sub.2).sub.5-COOH]—CO— for aspartic acid.

According to a particular embodiment, the amino acid sequence of the substrate peptide is selected from the group consisting of SEQ ID NOs: 25-33.

According to a specific embodiment the substrate has the amino acid sequence as set forth in SEQ ID NO: 31, wherein X is cysteine, aspartic acid, glutamic acid, arginine or lysine. According to a particular embodiment, the X is cysteine.

According to a specific embodiment the substrate has the amino acid sequence as set forth in SEQ ID NO: 30, wherein X is cysteine, aspartic acid, glutamic acid, arginine or lysine. According to a particular embodiment, the X is cysteine.

Thus, an exemplary sequence contemplated by the present inventors is one set forth in SEQ ID NO: 38 or 39.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain, either the amino or the carboxyl group of the first amino acid is protected by a suitable protecting group.

The protected or modified amino acid can then either be attached to an inert solid support or utilized in solution by adding the next amino acid in the sequence having the complimentary (amino or carboxyl) group suitably protected, under conditions suitable for forming the amide linkage.

The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505. A preferred method of preparing the peptide compounds of the present invention involves solid-phase peptide synthesis, utilizing a solid support. Large-scale peptide synthesis is described by Andersson Biopolymers 2000, 55(3), 227-50.

As mentioned above, the peptides of this aspect of the present invention are attached to at least one moiety which generates a detectable signal on cleavage of the peptide by the 3CL protease of the SARS-CoV-2.

In some embodiments, the detectable moiety can be chemically conjugated (coupled) to the peptide of the invention, using any conjugation method known to one skilled in the art. For example, a detectable moiety can be conjugated to the substrate peptides disclosed herein, using a 3-(2-pyridyldithio)propionic acid N-hydroxysuccinimide ester (also called N-succinimidyl 3-(2pyridyldithio) propionate) ("SDPD") (Sigma, Cat. No. P-3415; see e.g., Cumber et al. 1985, Methods of Enzymology 112: 207-224), a glutaraldehyde conjugation procedure (see e.g., G. T. Hermanson 1996, "Antibody Modification and Conjugation, in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

Additionally, or alternatively, the detectable moiety is conjugated to the peptide by translationally fusing the polynucleotide encoding the peptide of the invention with the nucleic acid sequence encoding the detectable moiety.

The detectable signal may be directly detectable such as for example a fluorescent signal, a phosphorescent signal, a radioactive signal or a colour signal (such as emitted by a chromophore). Alternatively, the detectable signal may be indirectly detectable, such as for example a pre-enzyme, as further described herein below. Other examples of detectable moieties are described at length in U.S. Pat. Appl. No. 20050048473 which is fully incorporated herein by reference.

Any assay known in the art for monitoring proteolytic substrate cleavage can be used in accordance with this aspect of the present invention.

In one embodiment the assay is a homogeneous assay. As used herein the phrase "homogeneous assay" refers to an assay not requiring separation of signalling moiety from other assay components.

The composition is contacted with the sample being tested for the presence of the SARS-CoV-2 virus. If the virus is present in the sample, the viral 3CL protease is also present. This protease cleaves the substrate and a change in the signal from the signalling moiety can be observed. Such homogenous fluorescent and colorimetric assays are known to those skilled in the art. See, for example: Biochemistry, Allinger, Wang Q. M. et al., "A continuous calorimetric assay for rhinovirus-14 3C protease using peptide p-nitroanilides as substrates" Anal. Biochem. Vol. 252, pp. 238-45 (1997), and Basak S. et al. "In vitro elucidation of substrate specificity and bioassay of proprotein convertase 4 using intramolecularly quenched fluorogenic peptides" Biochem. J. Vol. 380, pp. 505-14 (2004).

In one embodiment, the moiety to which the peptides, which generates a detectable signal on cleavage of the substrate peptide by said 3CL protease, is a Förster Resonance Energy Transfer (FRET) pair, whereby cleavage of the substrate peptide generates a signal from the FRET pair. The FRET pair comprises a donor moiety and an acceptor moiety as further described herein below.

The traditional method to detect interactions of molecules, for example in a biochemical system, is to pull down one of the molecules and look at what comes down in a microscope. This is a direct measurement of a molecular interaction that inferred the interaction by coincidence in space. The problem with a normal wide-field microscope is that the diffraction limits are observable elements. So, a typical volume element that can be resolved with a wide-field microscope is in the order of $10^{-15}$ metres, which corresponds to approximately a micron cubed. However, the biomolecular entities interacting with each other that need to be detected have a way smaller volume in the order of $10^{-22}$ metres. This is several orders of magnitude less than what the conventional wide-filed microscope offers. Although co-localisation can be used in this case in order to infer interaction, the probability that the molecular interaction is observed with the co-localisation is very low. Here comes the FRET that actually allows to significantly decrease the detection volume.

As mentioned above, the FRET is a non-radiative energy transfer, where the term "non-radiative" is of particular importance. The non-radiative energy transfer is essentially based on a dipole-dipole coupling mechanism between the donor and acceptor of the interacting molecular pair in their excited states. It is not a trivial emission of a photon, but a re-absorption by the donor and acceptor.

There are a number of approaches to FRET quantification which can be used in the present invention:

1) Sensitised emission is a direct two-channel imaging technique using an algorithm that corrects for excitation and emission crosstalk;
2) Acceptor photobleaching (sometimes called donor dequenching) is a technique capable of measuring increased donor emission when the acceptor is photobleached;
3) Fluorescence lifetime imaging microscopy FRET (FLIM FRET) is a technique capable of detecting fluorescence lifetime changes of donor; and
4) Fluorophore donor spectral imaging is a technique involving excitation at one or two wavelengths and measuring the spectral profiles of both donor and acceptor.

If the donor of the FRET pair is normally excited, for example with a blue light, it is very quickly relaxed from a high excited state by interconversion or preparative relaxation to the first electron excited state. From there it can go back to the ground state either through the non-radiative decay interconversion, or through the radiative pathway by emitting a photon. In this case, the molecular orbitals of the donor can energetically couple with the orbitals of the acceptor, the dipole-dipole coupling occurs, thereby creating an extra channel for the non-radiative decay with much shorter excited state lifetimes. This results in the donor actually emitting less light, or in other words, quenching the donor when the sensitised emission FRET occurs. At the same time, as the donor radiative emission is quenched, the acceptor gets excited by this process as a result of the same dipole-dipole coupling and starts emitting fluorescence. So, by exciting the donor in this process, the emission is received also partially from the acceptor. The sensitised emission is perhaps the simplest FRET method, because there is a single excitation source, from which the donor fluorophore is excited, and the signal is collected using emission filters chosen for both the donor fluorescence and the acceptor fluorescence. The acceptor fluorescence increases in the presence of donor, whereas the donor fluorescence decreases in the presence of the acceptor. The ratiometric change of fluorescence intensity can then be used to measure the FRET. This is the most straight-forward approach to measuring the process of the FRET. It is inherently based on quenching of the donor molecules during the process, thereby increasing fluorescence intensity of the acceptor. The spectral images recorded in this approach are actually the donor emission upon excitation of the donor (DD) and the acceptor emission upon excitation of the donor (DA). The ratio between their intensities can indicate the FRET efficiency.

However, as mentioned above, the direct measurement of the FRET is not practical because of the donor bleed-through and acceptor direct excitation, as will be explained below. This is essentially a crosstalk between the two fluorophores (donor and acceptor). Thus, it is very difficult to obtain quantitatively accurate FRET data with this approach. Additional control experiments are required in order to establish the presence or absence of the FRET in a sample.

Despite the above limitations, it is possible however to deduce the FRET from the change in the emission of the donor or the acceptor. The major parameter that is used to quantify the FRET is the FRET efficiency E, which is basically the number of excited donors that transfer the energy to the acceptor, divided by the number of photons absorbed by the donor. So, this is basically a fraction of donors that transfer their energy to the acceptor. The FRET efficiency E can also be expressed as the following ratio:

$$E = \frac{R_0^6}{R_0^6 + r^6}$$

where R is the Förster radius (typically in the order of nanometres) that represents the distance between the donor and acceptor at which the FRET efficiency is 50% (when half of the excited donor molecules transfer their energy to the acceptor), and r is the distance between the donor and acceptor. Since it is $r^6$, it makes the dependence very steep. So, measuring the FRET efficiency E allows to assess the distance r between the donor and acceptor.

There are several methods to measure the FRET efficiency. The important point to consider here is the shape of the spectrum. The typical excitation spectra always have a tail toward the blue part of the spectrum and are steep at the red part of the spectrum. The typical emission spectrum looks opposite and symmetrical to the excitation spectra and are very steep at the blue part of the spectrum, but tail towards the red. Therefore, the acceptor can be specifically excited without exciting the donor, but the donor cannot be typically excited without exciting the acceptor. Similarly, the donor emission can be detected without detecting the acceptor, but the acceptor cannot be specifically detected without detecting the donor. Thus, the specific excitation of the acceptor and the specific detection of the donor become very relevant to the FRET measurements with a microscope.

Because of the aforementioned problems of the crosstalk between the donor and acceptor, this approach is only feasible when a donor and acceptor are in the same molecule, for example in the same polypeptide. In this case, the stoichiometry of the donor and acceptor can be kept constant in each pixel. This specifically works, for example, in bioassays and biosensors that can measure a change in a physiological parameter, such as calcium, or measure phosphorylation. Thus, the sensitised emission measurements can be useful for detecting rapid dynamic changes and is especially useful when examining fluorescent proteins where the FRET dynamic range is large, and the stoichiometry of the donor and acceptor is fixed at a 1:1 ratio.

The sensitised emission FRET can be implemented in various types of optical and spectroscopic device, for example, in wide-field imaging with proper filters, and it is very fast, because only two spectral images need to be acquired in this approach. However, this approach is not quantitative, because it allows to measure only differences in excited states, and the stoichiometry of donor and acceptor should be constant, which basically means that in many cases, they have to label different parts of the same molecule. In other words, and particularly in the present invention, the sensitised emission is used as a simple FRET method for acquiring preliminary information about the presence or absence of the object of interest, such as a DNA molecule of a certain pathogen. The answer in this case provides the initial indication for the presence of the molecule in the sample. Based on this initial indication, the system can be calibrated. Furthermore, the algorithm of the present invention will proceed to a further, quantitative sensitive measurement of the sample, which is based on another approach of the FRET measurement. This aspect will be described below.

In some ideal situation, if it is possible to excite the donor specifically without exciting the acceptor and to monitor fluorescence of the acceptor only, one would be able to observe the acceptor emission when there is energy transfer. So, it would be possible to make an image where the donor is excited and only the acceptor is detected. The problem discussed above is that the acceptor is excited directly and the bleed-through of the donor occurs in the acceptor channel. Thus, where the donor is excited, and the recorded acceptor emission does not equate to the sensitised emission, the image is essentially contaminated with the direct excitation and bleed-through. So, it is impossible to measure precisely how much acceptor goes through. However, it is possible to precisely measure the amount of the acceptor when excited directly at its excitation peak. This is possible simply because the donor is typically not excited at the excitation maximum of the acceptor, and the measurement will be very specific.

Since for the same molecule, the molar extinction coefficient (F) is constant, the ratio between the two specific excitations in the same spectrum is constant. Therefore, it is possible to precisely determine the amount of the acceptor at the donor emission maximum by exciting the acceptor at its excitation maximum. Exactly the same situation is with the donor bleed-through. It is impossible to precisely measure the acceptor in a sample containing both the donor and acceptor, because of the overlapping emission spectrum of the donor, but it is possible to measure the donor at that wavelength specifically in the absence of the acceptor.

In practice, the correction factors for the FRET measurements are determined as follows. First, for the sample containing only the donor, the intensity ratio $S_1$ between: (a) the donor emission at the acceptor emission maximum (the wavelength of the donor bleed-through into the acceptor detection channel), and (b) at the donor emission maximum, is determined. Second, for the sample containing only the acceptor, the intensity ratio $S_2$ between: (a) the acceptor excitation at the donor excitation maximum, and (b) the acceptor excitation maximum, is determined. Then, by measuring the sample containing both the donor and acceptor, by exciting only the acceptor in the presence of the donor, it is possible to determine how much acceptor is directly excited.

Thus, in the FRET experiment, after expressing the donor, the bleed-through correction is initially determined. The donor is excited in the sample in the absence of the acceptor, and therefore, the recorded are two spectral images: the donor measured at its emission maximum ($F_D$) and at the emission wavelength of the acceptor ($F_F$). The correction (scalar) factor $S_1$ for the bleed-through is then $S_1 = F_F/F_D$. It is only dependent on the spectrometer settings and the donor used, and it is calibrated only once using a donor-only sample.

Similarly, the correction for the direct excitation is introduced. The acceptor is measured in the sample in the absence of the donor. The recorded are two images: the acceptor excited at the donor excitation maximum ($F_F$) and at the excitation wavelength of the acceptor ($F_A$). The scalar factor $S_2$ for the direct excitation is then: $S_2 = F_F/F_A$. It is only dependent on the microscope settings and the acceptor used, and it is calibrated only once using an acceptor-only sample. So, for the sensitised emission, and assuming that the donor is not excited by the acceptor excitation, three images are taken:

1) the donor excitation/acceptor emission ($F_F$),
2) the donor excitation/donor emission ($F_D$) for determining the bleed-through factor $S_1$, and
3) the acceptor excitation/acceptor emission ($F_A$) for determining the direct excitation scalar factor $S_2$.

The scaled image intensity $F_F$ is then divided by the scaled acceptor intensity $F_A$ to obtain the FRET apparent efficiency that is proportional to the real FRET efficiency and to the fraction of interacting molecules. This scaling is easy to implement in most of the conventional optical instruments, such as a wide-field spectrometer or camera with appropriate filters. The overall measurement is fast because one can switch the filters quickly on a filter wheel or on a confocal microscope. However, this method is still semi-quantitative, because the resulted image obtained after scaling and correction is proportional to the relative concentration of interacting molecules, and it depends on the external calibration described above. The signal-to-noise ratio of this method is also low because of the scaling that requires measuring three separate samples. In addition, the spectra of the molecules should be invariant to the environment, for example it should be the same in a lipid environment and in a cytoplasmic environment. That is the case for many fluorescent proteins, fortunately.

Another approach for the FRET measurements is acceptor photobleaching and it is actually quantitative. Acceptor photobleaching is a method based on the fact that donor fluorescence is quenched during FRET when some of the donor fluorescence energy is transferred to the acceptor. But photobleaching the acceptor fluorophore stops it from fluorescing and thus from using some of the donor's energy, resulting in a total increase of donor fluorescence. This phenomenon can be used in order to calculate the FRET efficiency by subtracting the donor intensity in the presence of the acceptor from its intensity after photobleaching of the acceptor and dividing the result by the donor intensity after bleaching.

The advantage of this approach is that it is very robust and is quantitative. In this approach, the donor is excited and then its emission is recorded. If the FRET occurs, the donor is quenched, and so the emission intensity decreases, because this is actual channel for the non-radiative decay. In this method, the donor intensity should be initially measured in the absence of acceptor, and the FRET efficiency is calculated accordingly. The problem is that this approach assumes that a separate experiment where the donor is measured in the absence of the acceptor should be performed. However, this would be a completely different configuration with the different concentration of molecules, and the separate measurement should therefore be avoided, also because of the quantitation problems discussed above. The solution is specifically exciting the acceptor until it is completely saturated and cannot absorb more photons, and then the donor is re-measured. Bringing said acceptor fluorophore into short-lived and reversible dark states (e.g., a triplet state) during acceptor excitation would also prevent it from absorbing more photons. Such a process is also referred here as "acceptor saturation".

In general, fluorophores can undergo excitation through the absorbance of a photon and a following excitation of an electron from a low energy level (typically, the ground state) into a higher energy level (typically, the first excited state). The electron may lose some energy via phonons, and then spontaneously return to the ground state while emitting a photon (a process known as fluorescence or spontaneous emission). The lifetime for fluorescence emission is typically in nanoseconds. A second relaxation mechanism of the excited electron of a fluorophore (other than fluorescence) is through inter-system crossing into a triplet state. Such a transition is quantum-mechanically forbidden and therefore, it has a relatively low cross-section and a typical lifetime of microseconds, significantly longer than the fluorescence lifetime. Moreover, the electron may subsequently move to other metastable electronic levels, e.g., via encountering other molecules. Notably, these transitions do not involve photon emissions (or are very inefficient in doing so). Thus, these states are effectively considered as dark states. In the present invention, electronic inter-system crossing of the acceptor electron into a triplet state and additional dark states contribute to the FRET frustration, since the acceptor can no longer share the energy with the excited donor. This frustration is useful in the invention provided that the dark states are short-lived (in micro to milliseconds) relative to the modulation time of acceptor excitation, and that the transitions are reversible. Thus, the process of acceptor fluorophore entering a short-lived and reversible dark state (e.g., a triplet state) during acceptor excitation is also included here in the definition of the 'acceptor saturation'.

In this approach, when the acceptor is saturated, the donor becomes unquenched and its emission intensity will go up, which is actually the same situation as in the absence of the acceptor. The FRET apparent efficiency in this method is as follows:

$$E_{app} = 1 - \frac{F_D}{F_D^{\neq}}$$

where $F_D$ is the donor spectral image recorded when the donor quenched by the active acceptor, and $F_D^{\neq}$ is the donor spectral image recorded when the acceptor is photobleached. It will be more precisely defined in the Examples.

Although being semi-quantitative, this approach produces readings which are proportional to the fraction of the complex true efficiency. So, in this sense, it is rather the most quantitative method in terms of the intensity-based methods, and it does not require external calibrations, which is the case for the sensitised emission measurement. The control is actually internal by the bleaching in this method.

Along with the FRET fluorescence technique described above, other advanced spectroscopic techniques, such as proximity ligation (PLA), bimolecular fluorescence complementation (BiFC) and fluorescence cross-correlation spectroscopy (FCS), can be used in the present invention.

The term "donor fluorophore" as used herein refers to a light-sensitive, fluorescence emitting molecule, which initially in its electronic excited state, may transfer energy to "acceptor fluorophore" through non-radiative dipole-dipole coupling. The donor fluorophore must be bright (having high quantum yield and high absorption coefficient), stable (having long-living fluorescent excited state and low photo bleaching), and insensitive to the acceptor fluorophore excitation light.

The term "acceptor fluorophore" as used herein refers to a light-sensitive molecule, which initially in its ground-level electronic state may accept energy from "donor fluorophore" through non-radiative dipole-dipole coupling. The acceptor fluorophore must have a large Förster distance Ro from the donor fluorophore (high spectral overlap of the absorption spectrum of an acceptor fluorophore with the fluorescence emission spectrum of a donor fluorophore), low photobleaching, must be insensitive to the donor fluorophore excitation light, having no crosstalk of its fluorescence emission spectrum with the fluorescence emission spectrum of the donor fluorophore, and must be capable of undergoing reversible saturation of its fluorescence emission under light excitation.

Synthetic fluorophores used in the present invention may include, but are not limited to generic or proprietary fluorophores listed in Table C below:

TABLE C

Generic or proprietary exemplary fluorophores suitable for use in the present invention

| | |
|---|---|
| Type 1 | Fluorescein and derivatives thereof, Rhodamine and derivatives thereof, Alexa Fluor ® dyes, DyLight Fluor ® dyes, Cyanine Cy ™ dyes, ATTO ® dyes, Abberior STAR ® dyes, Dyomics ® dyes, DNA fluorescent stains (for example, DAPI or 4',6-diamidino-2-phenylindole), membrane fluorescent stains (for example, DiI or DilC$_{18}$(3), DiO or DiOC$_{18}$(3), DiD and DiR, which constitute a family of lipophilic fluorescent stains for labelling membranes and other hydrophobic structures). |
| Type 2 | A subset of Type 1 fluorophores, for example, Alexa Fluor ® 488, Alexa Fluor ® 555, Alexa Fluor ® 568, Alexa Fluor ® 647, Alexa Fluor ® 750, Alexa Fluor ® 790, ATTO ® 488, ATTO ® 520, ATTO ® 565, ATTO ® 647, ATTO ® 647N, ATTO ® 655, ATTO ® 680, ATTO ® 740, Cy2, Cy3, Cy3B, Cy3.5, Cy5, Cy5.5, Cy7, DyLight Fluor ® 750, Fluorescein Isothiocyanate (FITC), Dyomics ® 654 and IRDye ® 800CW. These dyes may change their fluorescent properties upon changes in the polarity of their environment. |
| Type 3 | Fluorescent proteins may include, but are not limited to, CFP, CyPET, GFP, YFP, YPET, RFP, and their mutants. |

TABLE C-continued

Generic or proprietary exemplary fluorophores suitable for use in the present invention Type 4  Photoactivatable or photoswitchable fluorescent proteins include, but are not limited to, PAGFP, Dronpa (and mutants such as Dronpa2, Dronpa3, Padron), rsFastLime, PAmCherry (and mutants PAmCherry1, PAmCherry2, or PAmCherry3, reCherry, rsCerryRev), PS-CFP1, PS-CFP2, Dendra1, Dendra2, Kaeda, KikGR, mKikGR, EosFP, mEos2, and KFP1.
Type 5  Quantum dots, quantum rods.
Type 6  Quenchers, for example the DYQ series by Dyomics ®, Black Hole Quencher Dyes by BioSearch Technologies ®, and the QSY series by ThermoFisher Scientific ®.
Type 7  Caged fluorophores that can include, but not limited to, fluorophores that become fluorescent upon illumination with UV light.
Type 8  Bioluminescent fluorophores may include, but are not limited to, Luciferase derived chimeras.
Type 9  Chemiluminescent fluorophores.
Type 10 Phosphorescent fluorophores may include, but are not limited to, lanthanides with or without sensitizers.

Examples of donor fluorophores that can be used with the peptides of the present invention, including but not limited to: CAL Fluor® Gold 540, CAL Fluor® Orange 560, Quasar® 670, Quasar® 705, 5-FAM (also called 5-carboxyfluorescein; also called Spiro(isobenzofuran-1(3H), 9'-(9H)xanthene)-5-carboxylic acid,3',6'-dihydroxy-3-oxo-6-carboxyfluorescein); 5-Hexachloro-Fluorescein ([4,7,2',4', 5',7'-hexachloro-(3',6'-dipivaloyl-fluoresceinyl)-6-carboxylic acid]); 6-Hexachloro-Fluorescein ([4,7,2',4',5',7'-hexachloro-(3',6'-dipivaloylfluoresceinyl)-5-carboxylic acid]); 5-Tetrachloro-Fluorescein ([4,7,2',7'-tetra-chloro-(3', 6'-dipivaloylfluoresceinyl)-5-carboxylic acid]); 6-Tetrachloro-Fluorescein ([4,7,2',7'-tetrachloro-(3',6'-dipivaloylfluoresceinyl)-6-carboxylic acid]); 5-TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3, 6-bis(dimethylamino); EDANS (5-((2-aminoethyl) amino)naphthalene-1-sulfonic acid); 1,5-IAEDANS (5-((((2-iodoacetyl)amino)ethyl) amino)naphthalene-1-sulfonic acid); DABCYL (4-((4-(dimethylamino)phenyl) azo)benzoic acid) Cy5 (Indodicarbocyanine-5) Cy3 (Indo-dicarbocyanine-3); and BODIPY FL (2,6-dibromo-4,4-difluoro-5,7-dimethyl-4-bora-3a,4a-diaza-s-indacene-3-proprionic acid), ROX, as well as suitable derivatives thereof. Additional examples include, but are not limited to fluorescein, fluorescein chlorotriazinyl, rhodamine green, rhodamine red, tetramethylrhodamine, FITC, Oregon green, Alexa Fluor (e.g. AF488), FAM, JOE, HEX, Texas Red, TET, TRITC, cyanine-based dye and thiadicarbocyanine dye. According to a particular embodiment, the fluorophore is AF488 or EDANS.

In one embodiment, the donor moiety is a quantum dot. Quantum dots are coated nanocrystals fabricated from semiconductor materials in which the emission spectrum is controlled by the nanocrystal size. Quantum dots have a wide absorption spectrum, allowing simultaneous emission of fluorescence of various colours with a single excitation source. Quantum dots can be modified with large number of small molecules and linker groups such as conjugation of amino (PEG) or carboxyl quantum dots to streptavidin (Quantum Dot Corporation, Hayward, CA, USA).

In some embodiments of the present invention, the donor and acceptor moieties are attached to the peptide in a configuration that permits energy transfer from the donor to the acceptor to result in quenching of the fluorescence by FRET.

In one embodiment, the donor moiety and acceptor moiety are separated by no more than three or five amino acid residues. In another embodiment, the donor and acceptor are separated by no more than 10 amino acid residues. In yet another embodiment, the donor and acceptor are separated by no more than 15 amino acid residues. In yet another embodiment, the donor and acceptor are separated by no more than 20 amino acid residues.

In some embodiments, the FRET efficiency E described above is not limited, per se, except that a quenching effect should minimally be detectable by whatever detection instrumentation is used. Fluorescence is considered "quenched" when fluorescence emitted by donor in the presence of acceptor is reduced by at least 10%, for example, 15%, 20%, 30%, 40%, 50%, 60%, 70%, 80%, 90%, 95%, 98%, 99%, 99.9% or more. As mentioned above, the acceptor moiety used in the present invention may be radioactive or non-radioactive, dependent on the FRET mechanism and technique used. Some acceptor fluorophores, for example, tetramethyl-6-carboxyrhodamine (TAMRA), can re-emit the energy absorbed from the donor fluorophore at a wavelength or using a signal type that is also detectable but distinguishable from the donor fluorophore emission. Other acceptor moieties, such as the Black Hole Quenchers (BHQs), including Black Hole Quencher-1 (BHQ-1), Black Hole Quencher-2 (BHQ-2), Black Hole Quencher-3 (BHQ-3) have no native fluorescence, thus can virtually eliminate background problems described above and seen with other acceptors. The Black Hole Quenchers, which can be used to quench almost all donor fluorophores, are commercially available, for example, from Biosearch Technologies, Inc. (Novato, CA).

Examples of FRET pairs contemplated by the present invention include fluorescein isothiocyanate/tetramethyl-6-carboxyrhodamine (FITC/TAMRA), fluorescein amidite/TAMRA (FAM/TAMRA), FAM/black hole quencher-1 (FAM/BHQ1), AF488 and BHQ1 (AF488/BHQ1) and EDANS and Dabcyl (EDANS/dabcyl).

In one embodiment, the C-terminus of the peptide is attached to the acceptor moiety and the N-terminus of the peptide is attached to the donor moiety.

In another embodiment, the C-terminus of the peptide is attached to the acceptor moiety and the donor moiety is attached to no more than three amino acids from the N-terminus.

In still another embodiment, the donor moiety is attached to a separating moiety which is not part of the substrate sequence per se (for example to a cysteine).

Contemplated peptides which comprise FRET pairs include those set forth in SEQ ID NOs: 1-10. In one embodiment, the peptides are those set forth in SEQ ID NOs: 2-10. In a particular embodiment, the peptide has the amino acid sequence as set forth in SEQ ID NO: 8.

In another embodiment of the present invention, the signalling moiety is a chemiluminescent signalling moiety. The chemiluminescent signalling moiety is attached to one side of the cleavage region of the substrate and an acceptor moiety is attached at the other side of the cleavage region. U.S. Pat. No. 6,243,980, the contents of which are incorporated by reference, describes such detection system, involving the use of a chemiluminescent 1,2-dioxetane compound as the signalling moiety. If the viral protease is not present in the sample, cleavage of the substrate does not occur. The energy from the 1,2-dioxetane decomposition is transferred to the acceptor moiety and released at a wavelength distinct from the emission spectrum of the 1,2-dioxetane. If the substrate is cleaved, the acceptor moiety is separated from the 1,2-dioxetane and a chemiluminescent emission from the dioxetane compound is observed.

Enzymatic activity of the SARS-CoV-2 3CL protease can be detected using chromogenic substrates as described in: Wang, Q. M. et al. "A continuous colorimetric assay for rhinovirus-14 3C protease using peptide p-nitroanilides as substrates" Anal. Biochem. Vol. 252, pp. 238-45 (1997), the contents of which are incorporated by reference. Tagged substrates are used to determine the ability of the protease to cleave. The first peptide substrate used is tagged using p-nitroaniline. When p-nitroaniline is cleaved from the peptide, a signal is produced. The cleavage causes an aromatic pi-electron system to form, the presence of which absorbs in the 405 nm range of the electromagnetic spectrum. The nanomolar extinction coefficient of the cleaved p-nitroaniline is 104 mole-1 cm31

Alternatively, a substrate is constructed having a florescent tag attached to one end and a quencher attached to the other end. When the peptide is cleaved fluorescence is detected. Other tags use a similar principle using colour reactions.

In another embodiment the assay used for detecting 3CL protease activity is a heterogeneous assay. A "heterogeneous assay" is an assay in which the solid-phase is separated from another assay component during the assay. In this case the substrate is comprised in a composition which may have the following general formula:

wherein:
Y comprises the substrate of the viral protease, cleavage of X—Y—Z by said viral protease forming cleavage products X—Y' and Y"'—Z wherein Y' is a first cleavage product of Y and Y' is a second cleavage product of Y;

X comprises a detectable moiety; and

Z comprises a separating moiety capable of binding to a separate phase of a two-phase separating system;
wherein said X—Y—Z does not form a contiguous portion of a natural substrate said viral protease.

The detectable moiety X may directly or indirectly detect and may comprise a labelling agent such as an enzyme, a fluorophore, a chromophore, a protein (e.g., an epitope tag), a chemiluminescent substance and a radioisotope.

Separating moiety Z is being capable of directly or indirectly bind to a separate phase of a two-phase separating system (e.g., solid phase and liquid phase). Examples for separating moiety Z include an immunological binding agent, a magnetic binding moiety, a peptide binding moiety, an affinity binding moiety, a nucleic acid moiety.

The composition of the present invention may be incubated with the separating system prior to, concomitantly with or following incubation with the sample.

Measures should be taken that the detectable moiety does not bind to the separating moiety.

In one embodiment, a detectable moiety of the present invention is a pre-enzyme. Accordingly, upon substrate cleavage the enzyme can be activated and detected (via the detection of a catalytic activity of same). An example of such a pre-enzyme is pro-Thrombin (factor II) or other enzymes in this cascade.

In any of the embodiments described herein, any of the moieties can be directly linked to the peptide by a covalent bond or indirectly via a spacer molecule having coupling functional groups at each end. Examples of such linkers include an alkyl, a glycol, an ether, a polyether, a polynucleotide and a polypeptide molecule.

Solid-phases suitable for use in the heterogeneous assay include, but are not limited to test tubes, microtiter plates, microtiter wells, beads, dipsticks, polymer microparticles, magnetic microparticles, nitrocellulose, chip arrays and other solid phases familiar to those skilled in the art. The signalling moiety used in the heterogeneous assay may be any label known to those skilled in the art. Such labels include radioactive, calorimetric, fluorescent and luminescent labels.

A heterogeneous chemiluminescent assay for the detection of proteases is described in U.S. Pat. No. 56,243,980, the contents of which are incorporated by reference. In one embodiment, the homogeneous or heterogeneous assay method of the present invention is automated so that a result can be obtained without the need for medical staff to be exposed to a subject thought to be infected by the viral disease under test. For example, the subject can be tested in a clean room (for example, but not limited to P3 type room). The subject can pick up, or get before entering the room, a diagnostic kit, which can include a solid phase coated with a labelled peptide of the type discussed above. For example, the solid phase can be a tissue which was previously immersed with peptide, or a test stick that can be from the type used to test pregnancy. The subject can supply a sample, such as a saliva sample, at a pre-prepared spot on the solid phase.

The solid phase containing the sample is then incubated to allow the enzymatic reaction to occur. In one embodiment, the reaction temperature in controlled at 37° C. to provide optimal conditions for the enzyme reaction. When the incubation is complete, the sample to be tested can be measured on a spectrophotometer, using a remote control, or a mechanical system operated manually from outside the room. The sample can be tested for a qualitative colour or UV detection. After the test the sample can be discarded by an automated system, or a remote operated handle that trashes the sample. In one embodiment, the peptides described herein are attached on one end to a biotin moiety and to an HCG hormone on the other end. The 3CL protease may be detected using a lateral flow device configured for a pregnancy test (or the like).

Methods of analysing or monitoring detectable signals are known in the art. In one embodiment, the assay is carried out on a multi-well plate (e.g., 96 or 384 well plate) and a plate reader (e.g., TMG plate reader) is used for detection of the signal. This may be particularly relevant for rapid detections in public places such as educational locations (e.g., schools and universities) and travel related locations such as airports and hotels.

Many different configurations of optical and spectroscopic devices can be used in the present invention. For example, the optical device of the present invention may be modular and may be configured to operate as a portable and highly sensitive fluorescence spectrophotometer (fluorometer), luminometer, fluorescence microscope or combinations thereof for measuring fluorescence, luminescence or phosphorescence. These optical devices may be conveniently placed at the entrance to public places, such as theatres, restaurants and places of work. Their miniaturised versions can be used for rapid point-of-care diagnostics in public areas, working places and at home.

An excitation module, a sample chamber and an acquisition module of the optical device of the present invention can be configured according to a desired application and adapted for the particular application. For example, the sample chamber may be chosen as a fluorescence multiplate reader for laboratory high-throughput and rapid, multiplexing analysis of multiple samples for point-of-care diagnostics.

In some embodiments, a detector and a computing unit are combined in a single unit designed to perform acquisition of the fluorescence emission, to measure its intensity, to process the fluorescent emission data and optionally display it in a readable format and/or output it to an external memory or user's interface. In another specific embodiment, the acquisition module may be a part of a smartphone or any other mobile device or gadget suitable for performing the desired measurements. In a certain embodiment, the detector is an electron-multiplying charge-coupled device (EMCCD) imager, a charge-coupled device (CCD) imager, an avalanche photodiode (APD), a photomultiplier tube (PMT), scientific complementary metal-oxide-semiconductor (sCMOS) imager, or CMOS imager of a smartphone camera, a stand-alone camera, or a camera of any mobile device or gadget, said detector optionally having a focusing apparatus and a computer link. In a specific embodiment, the detector is a CMOS imager of a smartphone camera. In yet further specific embodiment, the sample chamber combined with the acquisition module constitutes a fluorescence microscope, or said optical device is a combined fluorometer and a fluorescence microscope installed in a single case, or said optical device is incorporated inside a fluorescence microscope. Said microscope is designed to generate raw data from single-molecule localisation as a video or as a series of static images and to further process said raw data generated by the microscope, to integrate said fluorescence emission intensity data and said microscope raw data and to provide information on the molecular interactions and on the nanometre proximity of single molecules in a readable format or to output said information to an external memory or user's interface. In a particular embodiment, said sample chamber is a multiplexing spectrophotometric or imaging device, or part thereof, suitable for multiplexing multiple samples. An example of such multiplexing device is the aforementioned microplate reader.

In case of the fluorometer functionality, the excitation sources may be selected from a wide-spectrum halogen lamp, an arc-lamp or a mercury-vapour lamp, configured to emit said donor fluorophore excitation light and said acceptor fluorophore excitation light in a predetermined wavelength range or near peak wavelength of said donor fluorophore or said acceptor fluorophore, respectively. The excitation monochromators in this case may be photomultiplier tubes (PMTs), and the emission monochromator may be a diffraction grating.

In case of a microscope functionality, the first and second excitation monochromators are first and second excitation filters, respectively, designed to select and transmit a narrow-wavelength beam of the excitation wavelength of light from the corresponding excitation source, while said emission monochromator is the emission filter designed to transmit a narrow-wavelength beam of said donor fluorophore emission.

Another device for analysing detectable signals in the present invention is a lateral flow device, which may be in a format of a stick or a stack. The lateral flow device may be based on a regular nitrocellulose membrane or a cellulose (paper) membrane. This type of device may be useful for home or point of care detection of the virus.

In a specific embodiment, the bioassay of the present invention is incorporated into a microfluidic chip or lab-on-a-chip. The method of the present invention can be adapted to perform on such chip.

The CELLSCAN® (Medis Technologies Ltd., New York, NY) is a cytometer that can be used to monitor protease activity. The heart of the CELLSCAN is a Cell carrier that contains up to 10,000 wells. A description of the CELLSCAN cytometer and its other uses for diagnosis of cancer and autoimmune diseases is available at: www(dot)medisel(dot)com.

A CELLSCAN probe is loaded with a peptide substrate such as those disclosed herein above. The peptide substrate is tagged with a donor group on one side of the cleavage region and an acceptor on the other. The sample under test is loaded on the probe. If active protease exists, the CELLSCAN will detect fluorescence caused by the cleaved peptide. The presence of active protease and its concentration in the sample is an indication of an active virus and serves as an indication for the contagious status of the patient.

In another embodiment, a paper-tissue-based automated system may be used for the detection of SARS-CoV-2. A solution of a colour-tagged peptide substrate (as disclosed herein above) specific for the 3CL protease of SARS-CoV-2 is prepared. A tissue (e.g., wet-wipes tissues) is immersed in the substrate compound solution and is kept moist. The specimen suspected of containing the SARS-CoV-2 viruses is put in contact with the tissue. If the SARS-CoV-2 virus is present, the 3CL protease cleaves the tagged peptide sequence and the reaction mixture develops or changes colour.

Several possibilities exist for detection of the coloured reaction product. For a qualitative analysis, a colour reaction may be detected visually. For a qualitative analysis, the tissue is transferred to spectrophotometric analyser for either fluorescence or colour detection. The process can be automated so as to protect those performing the assay from infection.

According to a particular embodiment, the assay can detect SARS-CoV-2 in less than 30 minutes, preferably in less than 20 minutes.

As mentioned, once SARS-CoV-2 is detected in a sample of the subject, the subject can be diagnosed as having a SARS-CoV-2 infection (i.e., as having COVID-19).

Thus, according to another aspect of the present invention there is provided a method of diagnosing a Severe acute respiratory syndrome coronavirus 2 (SARS-CoV-2) infection in a subject comprising contacting a sample of the subject with a composition comprising an agent that detects 3CL-protease of the SARS-Co-V2 virus, wherein a presence of said 3CL-protease in the sample is indicative of a SARS-Co-V2 infection.

As used herein, the term "diagnosing" refers to determining presence or absence of the virus in the subject, classifying the infection, determining a severity of the infection, monitoring virus progression, forecasting an outcome of a pathology and/or prospects of recovery and/or screening of a subject for the virus.

In one embodiment, the activity of the 3CL-protease is monitored, wherein an activity above a predetermined amount (e.g., the activity present in a negative control sample) is indicative of the subject having COVID-19. Monitoring the activity of 3CL-protease is described herein above.

In another embodiment, the amount of 3CL-protease in the sample is determined, wherein an amount above a predetermined amount (e.g., the amount present in a negative control sample) is indicative of the subject having COVID-19.

Quantifying the amount of 3CL-protease in samples may be approached on the protein or the polynucleotide level as summarized herein below.

Methods of Detecting Expression and/or Activity of 3CL-Protease

The expression level of 3CL-protease can be determined using methods known in the arts. Typically, the methods rely on antibodies which are capable of binding specifically to the 3CL protease. Thus, the invention according to some embodiments thereof also envisages the use of serum immunoglobulins, polyclonal antibodies or fragments thereof, (i.e., immunoreactive derivatives thereof), or monoclonal antibodies or fragments thereof. Monoclonal antibodies or purified fragments of the monoclonal antibodies having at least a portion of an antigen-binding region, including the fragments described hereinbelow, chimeric or humanized antibodies and complementarily determining regions (CDR). An exemplary antibody that can be used to detect 3CL protease is commercially available (Novus Biologicals, Catalogue number NBP1-78110).

Various types of detectable or reporter moieties may be conjugated to the 3CL protease antibody of the invention. These include, but are not limited to, a radioactive isotope (such as [125]iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomography (PET) or Magnetic Resonance Imaging (MRI).

Examples of suitable fluorophores are provided herein above. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabelled antibody binding protein (e.g., protein A labelled with $I^{125}$) immobilized on a precipitable carrier such as agarose beads. The number of counts in the precipitated pellet is proportional to the amount of substrate.

In an alternate version of the RIA, a labelled substrate and an unlabelled antibody binding protein are employed. A sample containing an unknown amount of substrate is added in varying amounts. The decrease in precipitated counts from the labelled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

Once a negative diagnosis of a SARS-CoV-2 infection is made, the present inventors further contemplate a message being generated or a notification being made which notifies the subject of the diagnosis.

Once a positive diagnosis of a SARS-CoV-2 infection is made, the present inventors further contemplate treating and/or managing the infection.

Examples of treatments for COVID include administration of an anti-viral agent, anti-viral regimen, hospital admittance, mechanical ventilation, invasive monitoring, last-resort drug, sedation, intensive care admission, surgical intervention, hospital admittance and isolation.

According to further embodiments, once a positive infection is diagnosed, the method further contemplates providing a recommendation to isolate the subject.

Kits which comprise the peptides of the present invention are also provided. The different kit components may be packaged in separate containers and admixed immediately before use. Such packaging of the components separately may permit long-term storage without losing the active components' functions. Embodiments in which two or more of components are found in the same container are also contemplated. An exemplary kit may comprise one or more of the following reagents: a) wash buffer reagent for use with heterogeneous assays; b) negative control reagent free of a protease capable of cleaving substrate; c) a positive control containing a protease capable of cleaving the substrate; (d) a signal generation reagent for development of a detectable signal from the signalling moiety; and (e) a sample collection means such as a syringe, throat swab, or other sample collection device, with appropriate collection buffer (matched to the specimen type).

In one embodiment, the protease used in the positive control comprises an amino acid sequence as set forth in SEQ ID NO: 34.

In another embodiment, the protease used in the positive control comprises a histidine tag (e.g. as set forth in SEQ ID NO: 35).

In one embodiment, the protease used in the negative control has an amino acid sequence as set forth in SEQ ID NO: 36.

For a multiple virus detection kit, in which one or more viruses are being detected as described herein above, each multi panel detection kit will be preferably designed according to a common theme, such as different viruses that cause the same or similar diseases, viruses that infect the same tissue or organ, viruses of close phylogenetic relationship such as viruses that are classified to the same family, subfamily and the like, viruses that can be detected in the same body fluid such as saliva, nasal secretion, blood, urine, feces etc., viruses that are common and widespread, viruses that spread via the same body fluid and more.

The reagents included in the kits can be supplied in containers of any sort such that the shelf lives of the different components are preserved and are not adsorbed or altered by the materials of the container. For example, sealed glass ampules may contain lyophilized reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kit may also comprise buffers which are suitable for analysing the proteases.

An exemplary buffer for analysing saliva includes 5 mM Bolt (stabilized DTT), 50 mM Tris pH 8.0, 0.75M Na2SO4. Optionally, the buffer may further comprise BSA (e.g. 0.2 mg/mL). The kit may also comprise protease inhibitors which are not active against SARS-CoV2 3CL protease. These include but are not limited to at least one of Antipain, AC-DEVD-CHO, Aprotinin, Eglin C, GW, PMSF and 2,6 PDA. According to a particular embodiment, the protease inhibitors include PMSF and GW.

Kits for buccal samples may also comprise protease inhibitors. Such protease inhibitors are preferably not active against SARS-COV-2 3CL protease. Examples of contemplated protease inhibitors include but are not limited to at least one of PMSF, GW, aprotinin, eglinC and pepstatin. According to a particular embodiment, the protease inhibitors include PMSF, GW, aprotinin and eglinC.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

3CL Protease Cloning and Production

Cloning: The bacterial expression vector pET14b was chosen as a backbone for expression of the various proteases in E. coli. The insert was flanked by XbaI and BamHI restriction sites hence the protease of interest was cloned in using these restriction enzymes.

Two viral proteases were produced and purified: SARS-CoV-2 3CL protease (3CLpro) (reference genome accession number: NC_045512) and Human Coronavirus 229e 3CLpro (reference genome accession number: NC_002645). Each protease was designed to have a N-terminal 6×HIS-tag directly followed by a TEV-protease cleavage site (ENLYFQG) to enable removal of the HIS-tag when desired. The required DNA sequences were ordered as linear double stranded DNA fragments (gBlocks from IDT) containing the XbaI and BamHI restriction sites.

Expression: Rosetta BL21 E. coli were transformed with the pET14b plasmid harboring the ORF for each protease and single colonies were grown in overnight cultures. The next day, 500 mL of LB (with ampicillin) was inoculated and grown until OD600=0.6. IPTG was added to a final concentration of 1 mM and the culture was incubated at 18° C. overnight for protein expression. Protein purification: All steps in the protein purification were performed on ice or at 4° C. Bacterial cells were centrifuged and the pellet was re-suspended in 25 mL of binding buffer. Next, the sample was sonicated for 3 cycles of 30 s with 60 s in between each cycle. Cell debris was removed by centrifugation for 20 min at 12.000 g followed by sterile filtration using a 0.22 m syringe filter. FF Histrap column (Cytiva) was washed with 10 column volumes (CVs) of water followed by 10 CVs of binding buffer. Next, the sample was applied to the column at a speed of 1 mL/min. The column was washed with at least 10 CVs of binding buffer until the absorbance levels of 280 and 230 nm were back to baseline. Elution was performed stepwise by mixing binding buffer with elution buffer to reach the desired imidazole concentration and fractions were collected. Unspecific proteins were eluted at imidazole concentrations of 20 mM, 50 mM, 80 mM and 100 mM imidazole (1 mL for each fraction). Next, the viral protease was eluted with 4 mL buffer containing 250 mM imidazole. After elution, the sample was quantified and the buffer was exchanged to storage buffer using Zeba desalting columns (Thermo-Fisher). Purified protein was stored at −20° C.

Figure 1:
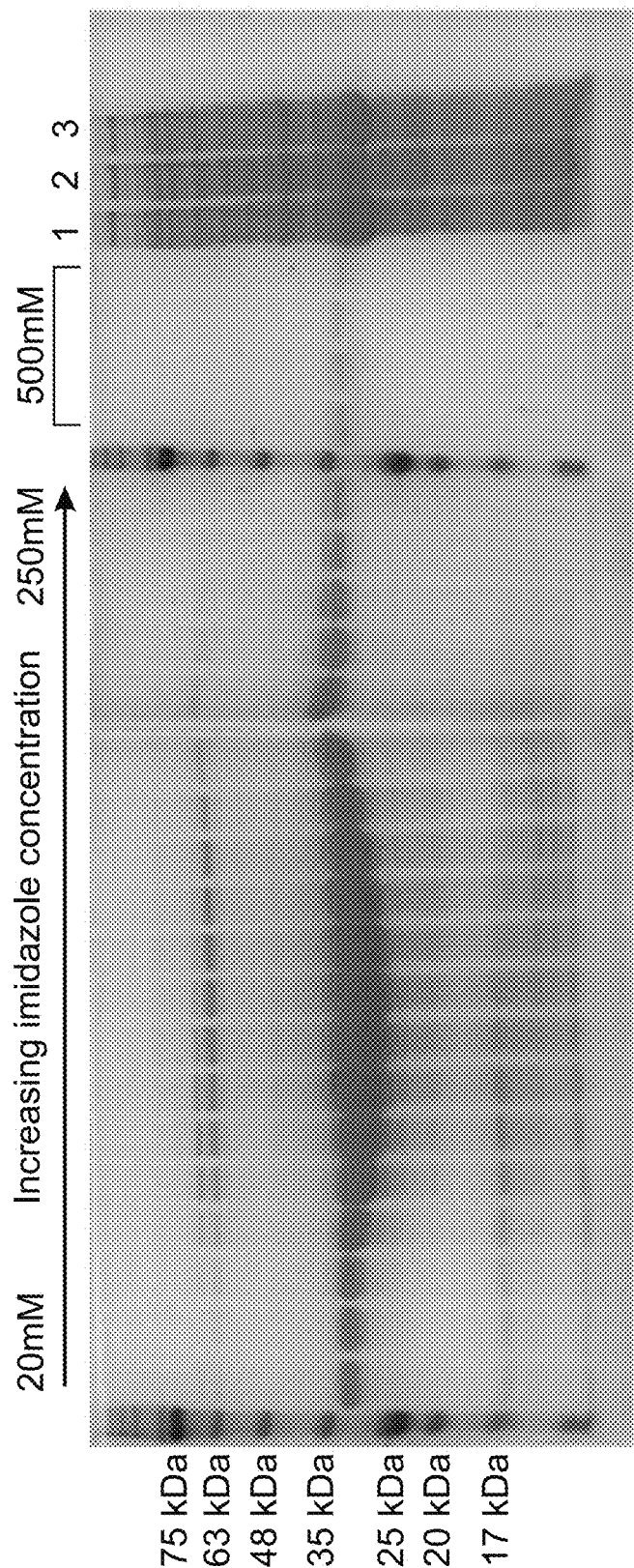
FIG. 1 shows the SDS PAGE gel with different fractions eluted from the Histrap column. Elution performed with a linear gradient starting with 20 mM and ending with 250 mM imidazole in 19 steps. A final elution with 500 mM imidazole was used to ensure that all protein was eluted. (1+2) Total cell lysate from an induced bacterial culture at 18° C. and 30° C. respectively. The 3CLpro is evidently present in the lysate and the 18° C. induction shows a higher abundance of the 3CLpro.
(3) Flowthrough of the 18° C.-induced lysate after binding to the Histrap column.

The protease elution profile from the Histrap column was optimized once for the SARS-CoV-2 protease. During the elution optimization, a linear gradient of imidazole concentration was used and fractions were collected. The imidazole concentration was raised from the initial 20 mM to a final concentration of 250 mM in 19 steps of 1 mL. Next, 3 mL of 500 mM imidazole was used to ensure that all proteins eluted from the column. FIG. 1 shows the elution profile. Based on these results, imidazole concentrations up to 100 mM were chosen to remove impurities followed by a 250 mM imidazole concentration for final elution of the 3CL proteases.

Figure 2:
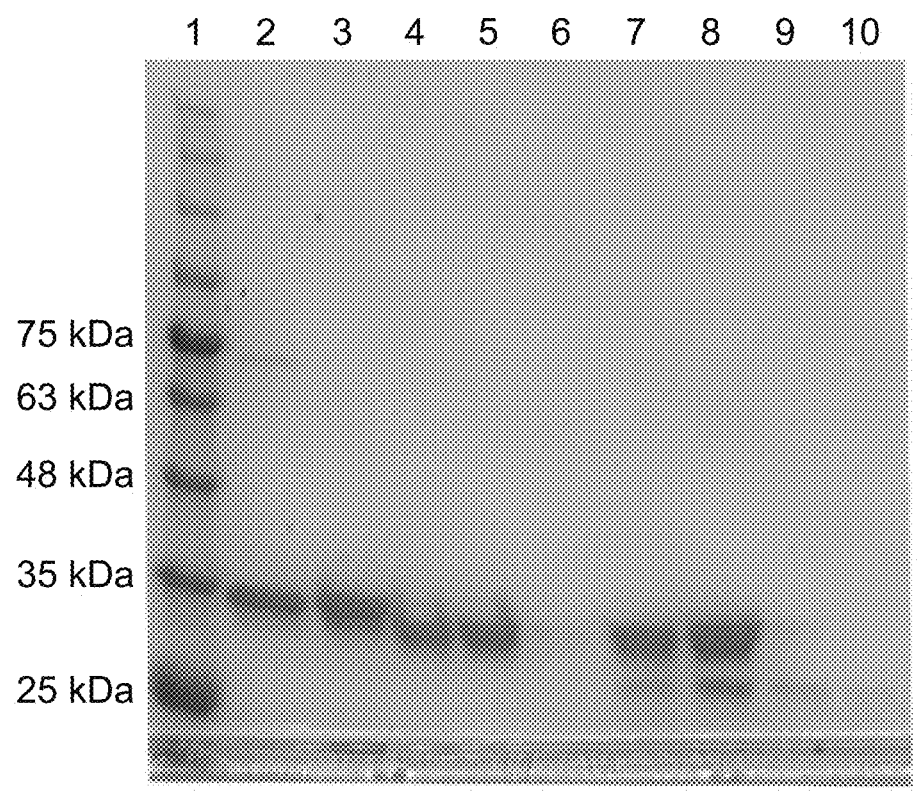
FIG. 2 shows the SDS-PAGE gel assessing 229e-3CLpro purity and TEV-cleavage of the SARS-CoV-2 3CLpro.
(1) Blueye pre-stained protein ladder.
(2) Purified 229e-3CLpro in storage buffer 2.
(3) Uncleaved SARS-CoV-2 3CLpro.
(4+5) TEV-cleaved SARS-CoV-2 3CLpro at 30° C. for 1 hour and at 4° C. overnight respectively. Samples were loaded on a Histrap column and the non-binding flow through was collected. The cleaved version weighs ~1.7 kDa less.

Purity of the protein was analyzed with a coomassie-stained SDS-PAGE gel. As shown in FIG. 2, both the 229e and SARS-CoV-2 3Cpro were obtained at high purity >93% (by densitometry; lane 2 and 3 respectively). Western blot was performed for SARS-CoV-2 3Cpro and the band was specifically detected with the antibody against SARS-CoV-2 3Cpro, see FIGS. 3A-C.

A published study from 2007 demonstrated that addition of a C-terminal or N-terminal HIS-tag to 3CLpro severely affect the enzymatic activity (Grum-Tokars et al., Virus Research, 2007). Therefore, the HIS-tag was added as a cleavable tag (ENLYFQG—SEQ ID NO: 37) that can be cleaved after purification by TEV-protease. The purified SARS-CoV-2 3CLpro was cleaved with TEV protease and its activity was compared to the uncleaved protease. Cleavage was performed at two different conditions: either at 30° C. for 1 hour or at 4° C. for overnight. TEV-protease was ordered from New England Biolabs and includes a HIS-tag. This way, the TEV-protease and potential uncleaved 3CLpro can subsequently be removed from the cleaved 3CLpro by running the reaction mixture on a Histrap column and to collect the flowthrough. Cleavage of the 3CLpro was successful as can be derived from FIG. 2 (molecular weight of the uncleaved=35.6 kDa and of the cleaved=33.9 kDa).

Example 2

Optimal Reaction Conditions for 3CL Activity

In order to find the final and optimal reaction conditions, several parameters were tested:

Reaction stabilizer (BSA): Enzyme that was incubated at RT for 5 hrs with 0.2 mg/mL BSA retained its activity.

Reducing agent: DTT and TCEP were tested at various concentrations to see if enzyme activity was affected. 5 mM DTT was shown to be the most effective at preserving enzyme activity. DTT-Bolt (Invitrogen Cat. B0009) showed an improved effect.

Glycerol, NaCl and Na2SO4: These parameters were tested as potential enzyme mediators. No positive effect on enzyme activity was noted for NaCl and glycerol. Na2SO4 enhanced enzyme activity. A concentration of 0.75 M Na2SO4 was selected. pH-enzyme activity: pH-enzyme activity at a wide pH range was tested (6.5, 7, 7.4, 8, 8.5). The activity was increased with increasing pH up to 8.0 (maximum activity) and decrease in pH 8.5.

The final assay conditions that are recommended: 96 well black non-binding flat bottom (REF 655900 Greiner Bio-one), reaction volume-100 μL (50 μL substrate solution added to 50 μL enzyme/saliva/spike solution), Reaction was monitored on BMG CLARIOstar plus with emission/excitation at 340/510 nm, gain-2000 (sensitivity of plate reader), enzyme concentration-150,300 ng/reaction, substrate concentration-5 uM; Reaction buffer-5 mM Bolt (stabilized DTT), 50 mM Tris pH 8.0, 0.75M Na2SO4 and 0.2 mg/mL BSA.

A summary experiment was performed to validate optimization efforts, final assay conditions and reaction rate improvement. Assay was performed by adding 5 μl saliva to 45 μl reaction buffer with and without 300 ng 3CL spiking. Reaction was initiated by addition of 50 μl of 10 uM kit substrate (5 μM final concentration from commercial kit BPS cat. 79955-1). 3 different saliva samples were tested, represented here by sample Y, FIGS. 3A-C.

As clearly demonstrated by FIGS. 3A-C and Table 1, the optimization procedure resulted with significant improvement in enzyme activity under the final buffer conditions (2986 RFU/min) compared with the commercial buffer (186 RFU/min) and the starting buffer (110 RFU/min). Over an order of magnitude improvement was recorded. This improvement effect was maintained under saliva clinical sample condition and spiking of 3CLpro. Spike effect (Delta) in the final buffer (1586) compared with the delta in the commercial buffer (303 RFU/min) and the starting buffer (82 RFU/min). This translates to ten to fivefold improvement in signal to noise from 0.1 to 0.5-1.

TABLE 1

|  | Commercial buffer | Starting buffer | Final buffer |
| --- | --- | --- | --- |
| Enzyme | 186 +/− 20 | 25 +/− 24 | 2986 +/− 90 |
| Saliva | 2996 +/− 32 | 2215 +/− 33 | 3024 +/− 126 |
| Saliva + enzyme | 3299 +/− 21 | 2297 +/− 38 | 4572 +/− 73 |
| Blank | −15 +/− 5 | −84 +/− 2 | 92 +/− 32 |
| Delta spike | 303 | 82 | 1586 |

Example 3

Effect of Substrate Sequence and FRET Pair on 3CL Specific and Saliva Nonspecific Activities 5 substrates were designed and compared to a known kit substrate (Biosyn).

```
                                    (SEQ ID NO: 1)
Kit substate-Dabcyl-KTSAVLQSGFRKME-EDANS (A4760-1 - SEQ ID NO: 2)
Substrate#1-Dabcyl-TSAVLQSGFRK-EDANS (A4760-2 - SEQ ID NO: 3)
Substrate#2-Dabcyl-TSAVLQSGF-EDANS (A4760-3 - SEQ ID NO: 4)
Substrate#3-Dabcyl-AVLQSGF-EDANS (A4760-4 - SEQ ID NO: 5)
Substrate#4-Dabcyl-AVLQSGFRK-EDANS (A4760-5 - SEQ ID NO: 6)
Substrate#5-Dabcyl-TSAVLQSGFYK-EDANS
```

For these enzymatic reactions 150 ng/well enzyme was used under final and optimized assay conditions, i.e. 5 μM substrate. Experiment were tested with 3 different saliva samples; representative results are shown.

The results are illustrated in FIG. 4 and FIGS. 5A-F and summarized in Table 2.

TABLE 2

|  | Commercial substrate | #1 | #2 | #3 | #4 | #5 |
| --- | --- | --- | --- | --- | --- | --- |
| Enzyme | 2312 +/− 25 | 978 +/− 14 | 449 +/− 36 | 354 +/− 18 | 1077 +/− 35 | 527 +/− 7 |
| Saliva | 2309 +/− 64 | 1123 +/− 35 | 187 +/− 7 | 47 +/− 5 | 1515 +/− 40 | 4688 +/− 53 |
| blank | 94 +/− 16 | 34 +/− 8 | 7 +/− 4 | 15 +/− 2 | 41 +/− 1 | 66 +/− 1 |

In order to improve assay sensitivity, 4 additional substrates were synthesized and tested with BHQ1/AF488 FRET pair (Cambridge research biochemicals):

Substrate #1-[BHQ-1]-TSAVLQSGFRK-[Cys(AF488)]-amide (4168-3)—SEQ ID NO: 7
Substrate #2-[BHQ-1]-TSAVLQSGF-[Cys(AF488)]-RK-amide (41469-2)—SEQ ID NO: 8
Substrate #3-[BHQ-1]-AVLQSGF-[Cys(AF488)]-RK-amide (41470-2)—SEQ ID NO: 9
Substrate #4-[BHQ-1]-AVLQSGFRK-[Cys(AF488)]-amide (A4771-1)—SEQ ID NO: 10.

The following assay conditions were used:
Method: emission/excitation at 488/535 nm, gain—1400.
Buffer-5 mM Bolt (DTT), 50 mM Tris pH 8.0, 0.75M Na2SO4 no BSA (as it has an effect on substrate cleavage).
Substrates concentration—1 uM.

Experiment were tested with 3 other saliva samples; representative results are shown in FIG. 6 and FIGS. 7A-D and summarized in Table 3.

TABLE 3

|  | CBR #1 | CBR #2 | CBR #3 | CBR #4 | Biosyn #1 |
|---|---|---|---|---|---|
| Enzyme | 5508 +/− 86 | 6425 +/− 41 | 461 +/− 18 | 657 +/− 6 | 30 +/− 1.3 |
| Saliva | 1356 +/− 37 | 512 +/− 16 | 154 +/− 6 | 726 +/− 25 |  |
| blank | 38 +/− 3 | 23 +/− 4 | 28 +/− 1 | 41 +/− 1 | 4 +/− 0.2 |

The new substrates resulted in higher assay sensitivity (as compared to the bioSYNTHESIS peptides). For substrate 2 (SEQ ID NO: 8), signal to noise was improved by over two orders of magnitude (from 0.1 to 12.5).

SARS-CoV-2 3CL Pro Specific Enzymatic Activity Evaluation

The specific enzymatic activity of 3CL Pro of SARS-CoV-2 was tested with 4 different substrates (Biosyn #1, 6, 7 and BPS substrate) and compared to the enzymatic activity of Human Rhinovirus (HRV) and the common Human Coronavirus species CoV-229E. Running condition: Substrate concentration-5 uM, enzyme concentration 150 ng/reaction.

```
BPS substrate (cov19) - Dabcyl-KTSAVLQSGFRKME-

EDANS (SEQ ID NO: 1; 79955-1, BPS Bioscience)

Biosyn#1 (cov19)-Dabcyl-TSAVLQSGFRK-EDANS (SEQ ID

NO: 2; A4760-1, bioSYNTHESIS)

Biosyn#6 (229e)-Dabcyl-YGSTLQAGLRK-EDANS (SEQ ID

NO: 11; A4911-1, bioSYNTHESIS)

Biosyn#7 (HRV)-Dabcyl-LEALFQGP[Asp-(EDANS) SQ

[Amide] (SEQ ID NO: 12, A4911-2, bioSYNTHESIS.
```

The results are summarized in Tables 4 and 5 herein below.

TABLE 4

Enzymatic activity (RFU/min) of SARS-CoV-2, HCoV-229E and HRV using 4 substrates

| Substrate | Blank Blank | Blank SD | SARS-CoV-2 Slope | SARS-CoV-2 SD | HCoV-229E Slope | HCoV-229E SD | HRV Slope | HRV SD |
|---|---|---|---|---|---|---|---|---|
| BPS (commercial) | 79 | 8 | 1658 | 21 | 493 | 17 | 87 | 7 |
| Biosyn#1 | −1 | 10 | 913 | 15 | 856 | 51 | −12 | 6 |
| Biosyn#6 | 64 | 24 | 349 | 52 | 213 | 23 | 44 | 13 |
| Biosyn#7 | 44 | 9 | 43 | 13 | 45 | 8 | 1041 | 32 |

TABLE 5

Specific Enzymatic activity of HoCoV-19 compared to HCoV-229E and HRV using 4 substrates

|  | % Enz activity | | |
|---|---|---|---|
| Substrate | SARS-CoV-2 | HCoV-229E | HRV |
| BPS (commercial) | 100 | 26 | 1 |
| Biosyn#1 | 100 | 95 | −1* |
| Biosyn#6 | 190 | 100 | −7* |
| Biosyn#7 | 0 | 0 | 100 |

The specific enzymatic activity of HoCoV-19 can be derived from the results that are presented in Tables 4 and 5. Cross reactivity was detected for Biosyn #1 substrate. The enzymatic activity of HoCoV-19 was similar to that of HCoV-229E for Biosyn #1 substrate. This cross reactivity was expected to some extent due to the high evolutionary conservation of the 3CL protease. However, both BPS and Biosyn #6 substrates had greater activity towards SARS-CoV-2 than HCoV-229E protease. This difference in activity can serve as a differentiating factor between these viruses.

Complete specificity (no cross reactivity) was observed for the most abundant common cold virus, HRV. The Biosyn #7 substrate was specific for HRV.

Enzymatic activity (RFU/min) of SARS-CoV-2, HCoV-229E and HRV 3CL and 3C proteases using peptide (SEQ ID NO: 8) is summarized in Table 6. Substrate concentration-1 µM, enzyme concentration 150 ng/reaction.

TABLE 6

| | Blank | | SARS-CoV-2 | | HCoV-229E | | HRV | |
|---|---|---|---|---|---|---|---|---|
| Substrate | Blank | SD | Slope | SD | Slope | SD | Slope | SD |
| SEQ ID NO: 8 | 23 | 3 | 3536 | 119 | 1116 | 6 | 9 | 7 |

Enzymatic activity (RFU/min) of SARS-CoV-2, HCoV-229E and HRV using 4 substrates

Example 4

Optimizing Inhibitor Cocktail to Maximize Saliva Non-Specific Protease Activity Inhibition The purpose of adding protease inhibitors to the buffer is to reduce nonspecific saliva activity and increase signal to noise ratio. 29 inhibitors were tested using a competitive enzymatic activity assay of 3CL Protease in saliva samples.

Antipain, AC-DEVD-CHO, Aprotinin, Eglin C, GW, PMSF and 2,6 PDA all decreased non-specific protease activity in saliva, with a non significant inhibition of 3CL specific activity.

Various inhibitor cocktails were also tested:
Cocktail 1 (PMSF, GW, Aprotinin, Pepstatin and heparin);
Cocktail 2 (PMSF and GW)
Cocktail 3 (PMSF, GW and Aprotonin).

No significant difference was found between the different inhibitor cocktails.

Example 5

Optimizing Inhibitor Cocktail to Maximize Buccal Sample Non-Specific Protease Activity Inhibition 29 inhibitors were tested using a competitive enzymatic activity assay of 3CL protease in buccal samples.

PMSF, GW, aprotinin, eglinC and pepstatin all decreased non-specific protease activity in saliva, with a non significant inhibition of 3CL specific activity.

The four best inhibitors were Eglin C, GW, PMSF and 2,6 PDA.

Various inhibitor cocktails were also tested:
Cocktail 1 (PMSF, GW);
Cocktail 2 (Eglin C, GW, PMSF and 2,6 PDA)
Cocktail 2 reduced non-specific proteases to a greater degree than cocktail 1.

Example 6

Storage of Samples

Storage of samples (buccal, NMT and spike) at 4° C. resulted with preservation of about 50% of enzymatic activity after 24 h. The most significant reduction occurred between 0-2 hrs. The enzymatic activity of all sample remained stable between 4-8 hrs. Nevertheless, spiking of 3CL recombinant protease into Buccal and NMT swabs can clearly be detected after 24 h at 4° C. and after freeze/thaw cycle, storing samples at −20° C.

Example 7

Comparison of PCR Test with 3CL Activity Assay

The sensitivity of the assay was compared to the sensitivity of a PCR assay for various genes (RdR gene—FIG. 17A, E gene—FIG. 17B and N gene—FIG. 17C). As shown, higher 3CL protease activity ratios correlate with PCR Ct values indicative of higher viral RNA copy number.

As summarized in Table 7, positive results were obtained using the 3CL protease activity assay from samples collected more than one month after symptom onset.

TABLE 7

| Patient | PCR result | Ct value E | Ct value RdR | Ct value N | 3Cl sample: days from symptom onset | 3CL protease Assay Ratios-NP | 3CL protease Ratios-buccal |
|---|---|---|---|---|---|---|---|
| 1 | positive | | No data | | 12 | 1.58 | NT |
| 2 | Low positive | 0 | 38 | 37 | 41 | 1.87 | NT |
| 3 | Low positive | 0 | 39 | 0 | ND | 1.32 | NT |
| 4 | Low positive | 39 | 0 | 0 | 12 | 1.44 | NT |
| 5 | positive | 22 | 24 | 23 | ND | 2.73 | 2.49 |
| 6 | positive | 23 | 25 | 22 | 31 | 2.26 | 1.70 |
| 7 | positive | 24 | 25 | 23 | ND | 3.61 | 2.45 |
| 8 | positive | 26 | 27 | 26 | 17 | 4.52 | 3.23 |

ND = Not determined, no data
NT = Not tested

In addition, any priority document(s) of this application is/are hereby incorporated herein by reference in its/their entirety.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of diagnosing a Severe Acute Respiratory Syndrome Coronavirus 2 (SARS-CoV-2) infection in a sample of a subject, the method comprising contacting the sample with a peptide that detects 3CL-protease of the SARS-Co-V2 virus, said peptide comprising the sequence as set forth in SEQ ID NO: 8, wherein a presence of said 3CL-protease in the sample is indicative of a SARS-Co-V2 infection.

2. A method of detecting a SARS-CoV-2 virus in a sample of a subject suspected of having COVID-19, the method comprising contacting the sample with a peptide that monitors the activity of a 3CL protease of the SARS-CoV-2 virus, said peptide comprising the sequence as set forth in SEQ ID NO: 8, wherein the activity level of said 3CL protease in the sample is indicative of the presence of SARS-CoV-2 in the sample.

3. The method of claim 1, wherein said sample is a saliva, buccal or nasopharyngeal sample.

4. The method of claim 1, further comprising the step of recording or reading said detectable signal with a device suitable for reading the signal.

5. The method of claim 1, wherein when said sample is a saliva sample, and said composition further comprises a protease inhibitor selected from the group consisting of Antipain, AC-DEVD-CHO, Aprotinin, Eglin C, GW, PMSF and 2,6 PDA.

6. The method of claim 1, wherein when said sample is a buccal sample, said composition comprises a protease inhibitor selected from the group consisting of PMSF, GW, aprotinin, eglinC and pepstatin.

7. The method of claim 6, wherein said protease inhibitor comprises PMSF, GW, aprotinin and eglinC.

8. A microfluidic chip or lab-on-a-chip suitable for carrying out the method of claim 1.

9. A method of treating a SARS-CoV-2 infection of a subject in need thereof comprising:
   diagnosing a SARS-CoV-2 infection in the subject according to the method of claim 1; and
   treating the subject.

10. The method of claim 4, wherein the device is a lateral flow device.

* * * * *